US009730926B2

(12) United States Patent
Lin et al.

(10) Patent No.: US 9,730,926 B2
(45) Date of Patent: Aug. 15, 2017

(54) COMBINATION THERAPY USING BISPECIFIC ANTI-C-MET/ANTI-EGFR ANTIBODY AND C-SRC INHIBITOR

(71) Applicant: Samsung Electronics Co., Ltd., Suwon-si, Gyeonggi-do (KR)

(72) Inventors: Powei Lin, Hwaseong-si (KR); Kwang Ho Cheong, Seoul (KR); Young Jun Koh, Yongin-si (KR); Jae-woong Hwang, Seoul (KR); Seung Hyun Lee, Suwon-si (KR); Jung Wook Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/600,986

(22) Filed: Jan. 20, 2015

(65) Prior Publication Data

US 2015/0216972 A1  Aug. 6, 2015

(30) Foreign Application Priority Data

Jan. 20, 2014  (KR) ........................ 10-2014-0006903

(51) Int. Cl.
A61K 31/496 (2006.01)
C07K 16/28 (2006.01)
A61K 45/06 (2006.01)
A61K 31/506 (2006.01)
A61K 31/517 (2006.01)
A61K 39/00 (2006.01)

(52) U.S. Cl.
CPC .......... *A61K 31/496* (2013.01); *A61K 31/506* (2013.01); *A61K 31/517* (2013.01); *A61K 45/06* (2013.01); *C07K 16/2863* (2013.01); A61K 2039/505 (2013.01); C07K 2317/24 (2013.01); C07K 2317/31 (2013.01); C07K 2317/56 (2013.01); C07K 2317/622 (2013.01); C07K 2317/73 (2013.01); C07K 2317/92 (2013.01)

(58) Field of Classification Search
CPC ............ C07K 2317/31; C07K 2317/56; C07K 2317/24; C07K 2317/73; A61K 2039/505
USPC ........................................... 424/135.1, 136.1
See application file for complete search history.

(56) References Cited

U.S. PATENT DOCUMENTS

| 7,125,875 B2 | 10/2006 | Das et al. | |
| 2009/0226443 A1* | 9/2009 | Filvaroff | A61K 31/517 424/138.1 |
| 2009/0226455 A1 | 9/2009 | Filvaroff | |
| 2011/0262436 A1* | 10/2011 | Bender | A61K 39/39558 424/133.1 |
| 2011/0287009 A1* | 11/2011 | Scheer | C07K 16/244 424/136.1 |
| 2014/0079689 A1* | 3/2014 | Elliott | C07K 16/468 424/133.1 |
| 2014/0302029 A1* | 10/2014 | Cho | C07K 16/2863 424/135.1 |
| 2014/0356366 A1* | 12/2014 | Cheong | C07K 16/32 424/136.1 |
| 2015/0030596 A1* | 1/2015 | Cheong | C07K 14/705 424/134.1 |
| 2015/0030599 A1* | 1/2015 | Cho | C07K 16/2863 424/136.1 |
| 2015/0056207 A1* | 2/2015 | Filvaroff | A61K 31/517 424/138.1 |
| 2015/0210766 A1* | 7/2015 | Kim | C07K 16/2863 424/136.1 |
| 2015/0322165 A1* | 11/2015 | Cheong | C07K 16/40 424/136.1 |
| 2016/0030559 A1* | 2/2016 | Lee | A61K 39/3955 424/136.1 |

OTHER PUBLICATIONS

Castoldi et al. Oncogene (2013) 32, 5593-5601.*
Hu et al. Published OnlineFirst Nov. 4, 2014; DOI: 10.1158/0008-5472.CAN-14-1670.*
Jarantow et al. The Journal of Biological Chemistry vol. 290, No. 41, pp. 24689-24704, Oct. 9, 2015.*
Kobold et al. JNCI J Natl Cancer Inst (2015) 107(1): dju364 (pp. 1-8).*
Spiess et al. Nature Biotechnology vol. 31 No. 8 Aug. 2013 (pp. 753-759).*
Zheng et al. MAbs. Jan. 13, 2016:0. [Epub ahead of print] (abstract only).*
MedChem Express (MCE)"AEE788" website product description (pp. 1-2, Jul. 3, 2016.*
R&D Systems (data sheet, catalogue # 358-MT, pp. 1-2, Oct. 12, 2015).*
Voskoglou-Nomikos (Clin. Can. Res. 9:4227-4239 (2003)).*
Cespdes et al. (Clin. Transl. Oncol. 8(5):318-329 (2006)).*
Talmadge et al. (Am. J. Pathol 170(3):793-804 (2007)).*
Dennis (Nature 442:739-741 (2006)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Dulak et al., "HGF-independent Potentiation of EGFR Action by c-Met", *Oncogene*, 30(33):3625-3635 (2011).
Dunn et al., "Dasatinib sensitizes KRAS mutant colorectal tumors to cetuximab", *Ocongene*, 30: 561-574 (2011).

(Continued)

*Primary Examiner* — Lynn Bristol
(74) *Attorney, Agent, or Firm* — Leydig, Voit & Mayer, Ltd.

(57) ABSTRACT

Pharmaceutical composition including a bispecific anti-c-Met/anti-EGFR antibody and a c-Src inhibitor and a method of preventing and/or treating cancer including co-administering a bispecific anti-c-Met/anti-EGFR antibody and a c-Src inhibitor to a subject in need thereof.

10 Claims, 19 Drawing Sheets

(56) References Cited

OTHER PUBLICATIONS

Haura et al., "Phase I/II Study of the Src Inhibitor Dasatinib in Combination With Erlotinib in Advanced Non-Small-Cell Lung Cancer", *Journal of Clinical Oncology*, 28(8): 1387-1394 (2010).

Mueller et al., "Met and c-Src Cooperate to Compensate for Loss of Epidermal Growth Factor Receptor Kinase Activity in Breast Cancer Cells", Cancer Research, 68: 3314-3322 (2008).

Sen et al., "Distinct interactions between c-Src and c-Met in mediating resistance to c-Src inhibition in head and neck cancer", *Clinical Cancer Research*, 17(3): 514-524 (2011).

Stabile et al., "c-Src Activation Mediates Erlotinib Resistance in Head and Neck Cancer by Stimulating c-Met", *Clinical Cancer Research*, 19:380-392 (2013).

Tang et al., "Dual MET-EGFR combinatorial inhibition against T790M-EGFR-mediated erlotinib-resistant lung cancer", *British Journal of Cancer*, 99: 911-922 (2008).

Wick et al., "Pathway inhibition: emerging molecular targets for treating glioblastoma", *Neuro-Oncology*, 13(6): 566-579 (2011).

Walter, Annette O., et al, "Discovery of a mutant-selective covalent inhibitor of EGFR that overcomes T790M-mediated resistance in NSCLC," *Cancer Discov.*, 3(12), 1404-1415 (2013).

Haglund, Caroline, et al, "In vitro evaluation of clinical activity and toxicity of anticancer drugs using tumor cells from patients and cells representing normal tissues," *Cancer Chemother Pharmacol*, 69, 697-707 (2012).

"ATCC Product Sheet LoVo (ATCC CCL-229)", downloaded from https://www.atcc.org/ps/CCL-229.ashx on Sep. 12, 2016.

"ATCC Product Sheet NCI-H820 [H820] (ATCC HTB-181)", download from http://www.atcc.org/ps/HTB-181.ashx on Sep. 12, 2016.

"ATCC Product Sheet HCT 116 (ATCC CCL-247)", download from https://www.atcc.org/ps/CCL-247.ashx on Sep. 12, 2016.

"ATCC Product Sheet NCI-H1975 [H-1975, H1975] (ATCC CRL-5908)", downloaded from https://www.atcc.org/ps/CRL-5908.ashx on Sep. 12, 2016.

* cited by examiner

SEQUENCE LISTING

```
<160> NUMBER OF SEQ ID NOS: 128

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
```

```
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MISC_FEATURE
<222> LOCATION: (1)
<223> OTHER INFORMATION: Xaa is Pro or Ser or absent
<220> FEATURE:
<221> NAME/KEY: MISC_FEATURE
<222> LOCATION: (2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MISC_FEATURE
<222> LOCATION: (3)
<223> OTHER INFORMATION: Xaa is Asn or Lys
<220> FEATURE:
<221> NAME/KEY: MISC_FEATURE
<222> LOCATION: (4)
<223> OTHER INFORMATION: Xaa is Ala or Val
<220> FEATURE:
<221> NAME/KEY: MISC_FEATURE
<222> LOCATION: (7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MISC_FEATURE
<222> LOCATION: (5)
<223> OTHER INFORMATION: X is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
```

```
<220> FEATURE:
<221> NAME/KEY: MISC_FEATURE
<222> LOCATION: (4)
<223> OTHER INFORMATION: Xaa is His, Arg, Gln or Lys
<220> FEATURE:
<221> NAME/KEY: MISC_FEATURE
<222> LOCATION: (9)
<223> OTHER INFORMATION: Xaa is Ser or Trp
<220> FEATURE:
<221> NAME/KEY: MISC_FEATURE
<222> LOCATION: (12)
<223> OTHER INFORMATION: Xaa is His or Gln
<220> FEATURE:
<221> NAME/KEY: MISC_FEATURE
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MISC_FEATURE
<222> LOCATION: (2)
<223> OTHER INFORMATION: Xaa is Ala or Gly
<220> FEATURE:
<221> NAME/KEY: MISC_FEATURE
<222> LOCATION: (4)
<223> OTHER INFORMATION: Xaa is Thr or Lys
<220> FEATURE:
<221> NAME/KEY: MISC_FEATURE
<222> LOCATION: (7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MISC_FEATURE
<222> LOCATION: (1)
<223> OTHER INFORMATION: Xaa is Gly, Ala or Gln
<220> FEATURE:
<221> NAME/KEY: MISC_FEATURE
<222> LOCATION: (6)
<223> OTHER INFORMATION: Xaa is Arg, His, Ser, Ala, Gly or Lys
<220> FEATURE:
<221> NAME/KEY: MISC_FEATURE
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
```

```
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
1               5

<210> SEQ ID NO 16
<211> LENGTH: 9
<212> TYPE: PRT
```

```
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

```
<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
```

```
            1               5                  10                 15
Asp Arg Val Thr Ile Thr Cys Lys Ser Ser Gln Ser Leu Leu Ala Ser
                    20                  25                 30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
50                  55                      60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                    85                  90                  95

Ser Tyr Ser Arg Pro Phe Thr Phe Gly Gln Gly Thr Lys Val Glu Ile
                100                 105                 110

Lys Arg
```

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

```
Pro Glu Tyr Tyr Met Ser
1               5
```

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

```
Pro Asp Tyr Tyr Met Ser
1               5
```

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

```
Ser Asp Tyr Tyr Met Ser
1               5
```

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

```
Arg Asn Asn Ala Asn Gly Asn Thr
1               5
```

<210> SEQ ID NO 26
<211> LENGTH: 8
<212> TYPE: PRT
<213> ORGANISM: Artificial Sequence

```
<220> FEATURE:
<223> OTHER INFORMATION: Synthetic CDR-H2 derived from YC321 clone

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
1               5                   10                  15

Ala
```

```
<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37
```

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic Synthetic nucleotide sequence of
      heavy chain of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc      60
cagtgtgagg tgaagctggt ggagtctgga ggaggcttgg tacagcctgg ggttctctg    120 agactctcct gtgcaacttc tgggttcacc ttcactgatt actacatgag ctgggtccgc    180
cagcctccag aaaggcact tgagtggttg gttttatta aaacaaagc taatggttac      240 acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc aagggactc tggtcactgt ctctgcagct    420
agcaccaagg gcccatcggt cttcccctg gcaccctcct ccaagagcac ctctggggc    480 acagcggccc tgggctgcct ggtcaaggac tacttcccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagcccca tcgagaaaac catctccaaa   1080
gccaaagggc agccccgaga accacaggtg tacaccctgc ccccatcccg ggaggagatg   1140

```
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                               1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain
    of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

```
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                            759
```

<210> SEQ ID NO 40
<211> LENGTH: 447

```
<212> TYPE: PRT
<213> ORGANISM: Artificial Sequence
<220> FEATURE:
<223> OTHER INFORMATION: Synthetic amino acid sequence of H1-heavy

<400> SEQUENCE: 40
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

```
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Arg Asp Asn Trp Phe Ala Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
    210                 215                 220
```

```
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
            435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Ser Tyr Ser Ala Pro Leu Thr Phe Gly Gly Gly Thr Lys Val Glu Ile
        100                 105                 110

Lys Arg Thr Val Ala Ala Pro Ser Val Phe Ile Phe Pro Pro Ser Asp
    115                 120                 125

Glu Gln Leu Lys Ser Gly Thr Ala Ser Val Val Cys Leu Leu Asn Asn
130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
1               5                   10                  15
```

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47

| | | | | | |
|---|---|---|---|---|---|
| gaggtgcagc | tggtggagtc | tgggggaggc | ttggtccagc | ctggagggtc | cctgagactc | 60 |
| tcctgtgcag | cctctggatt | caccttcact | gactactaca | tgagctgggt | ccgccaggct | 120 |
| ccagggaagg | ggctggagtg | gttgggcttt | attagaaaca | aagctaacgg | ttacaccaca | 180 |
| gaatacagtg | cgtctgtgaa | aggcagattc | accatctcaa | gagataattc | aaagaactca | 240 |
| ctgtatctgc | aaatgaacag | cctgaaaacc | gaggacacgg | ccgtgtatta | ctgtgctaga | 300 |
| gataactggt | tgcttactgg | ggtcaagga | accctggtca | ccgtctcctc | ggctagcacc | 360 |
| aagggcccat | cggtcttccc | cctggcaccc | tcctccaaga | gcacctctgg | ggcacagcg | 420 |
| gccctgggct | gcctggtcaa | ggactacttc | cccgaaccgg | tgacggtgtc | gtggaactca | 480 |
| ggcgccctga | ccagcggcgt | gcacaccttc | ccggctgtcc | tacagtcctc | aggactctac | 540 |
| tccctcagca | gcgtggtgac | cgtgccctcc | agcagcttgg | gcacccagac | ctacatctgc | 600 |
| aacgtgaatc | acaagcccag | caacaccaag | gtggacaaga | aagttgagcc | caaatcttgt | 660 |
| gacaaaactc | acacatgccc | accgtgccca | gcacctgaac | tcctgggggg | accgtcagtc | 720 |
| ttcctcttcc | ccccaaaacc | caaggacacc | ctcatgatct | cccggacccc | tgaggtcaca | 780 |
| tgcgtggtgg | tggacgtgag | ccacgaagac | cctgaggtca | agttcaactg | gtacgtggac | 840 |
| ggcgtggagg | tgcataatgc | caagacaaag | ccgcgggagg | agcagtacaa | cagcacgtac | 900 |
| cgtgtggtca | gcgtcctcac | cgtcctgcac | caggactggc | tgaatggcaa | ggagtacaag | 960 |
| tgcaaggtct | ccaacaaagc | cctcccagcc | cccatcgaga | aaaccatctc | caaagccaaa | 1020 |
| gggcagcccc | gagaaccaca | ggtgtacacc | ctgcccccat | cccgggagga | gatgaccaag | 1080 |
| aaccaggtca | gcctgacctg | cctggtcaaa | ggcttctatc | ccagcgacat | cgccgtggag | 1140 |
| tgggagagca | atgggcagcc | ggagaacaac | tacaagacca | cgcctcccgt | gctggactcc | 1200 |
| gacggctcct | tcttcctcta | cagcaagctc | accgtggaca | agagcaggtg | gcagcagggg | 1260 |
| aacgtcttct | catgctccgt | gatgcatgag | gctctgcaca | accactacac | gcagaagagc | 1320 |
| ctctccctgt | ctccgggtaa | atgactcgag | | | | 1350 |

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca aagctaacgg ttacaccaca     180
gaatacagtg cgtctgtgaa aggcagattc accatctcaa gagataattc aaagaactca     240
ctgtatctgc aaatgaacag cctgcgtgct gaggacacgg ccgtgtatta ctgtgctaga     300
gataactggt tgcttactg gggtcaagga accctggtca ccgtctcctc ggctagcacc      360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660 gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260 aacgtcttct catgctccgt gatgcatgag gctctgcaca accactacac gcagaagagc    1320 ctctcccctgt ctccgggtaa atgactcgag                                    1350

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49
gaggttcagc tggtggagtc tggcggtggc ctggtgcagc cagggggctc actccgtttg      60
tcctgtgcag cttctggctt caccttcact gattactaca tgagctgggt gcgtcaggcc     120
ccgggtaagg gcctggaatg gttgggtttt attagaaaca aagctaatgg ttacacaaca     180
gagtacagtg catctgtgaa gggtcgtttc actataagca gagataattc aaaaacaca      240 ctgtacctgc agatgaacag cctgcgtgct gaggacactg ccgtctatta ttgtgctaga     300
gataactggt tgcttactg gggccaaggg actctggtca ccgtctcctc ggctagcacc      360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660 gacaaaactc acacatgccc accgtgccca gcacctgaac tcctgggggg accgtcagtc     720
```

```
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaccatctc caaagccaaa      1020 gggcagcccc gagaaccaca ggtgtacacc ctgcccccat cccgggagga tgaccaag       1080 aaccaggtca gcctgacctg cctggtcaaa ggcttctatc ccagcgacat cgccgtggag      1140
tgggagagca atgggcagcc ggagaacaac tacaagacca cgcctcccgt gctggactcc      1200
gacggctcct tcttcctcta cagcaagctc accgtggaca agagcaggtg gcagcagggg      1260
aacgtcttct catgctccgt gatgcatgag gctctgcaca accactacac gcagaagagc      1320
ctctccctgt ctccgggtaa atgactcgag                                       1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

```
gacatcgtga tgacccagtc tccagactcc ctggctgtgt ctctgggcga gagggccacc       60
atcaactgca gtccagcca gagtctttta gctagcggca accaaaataa ctacttagct       120
tggcaccagc agaaaccagg acagcctcct aagatgctca ttatttgggc atctacccgg      180
gtatccgggg tccctgaccg attcagtggc agcgggtctg ggacagattt cactctcacc      240
atcagcagcc tgcaggctga agatgtggca gtttattact gtcagcaatc ctatagtgct      300
cctctcacgt tcggaggcgg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaaagca gactacgaga aacacaaagt ctacgcctgc      600
gaagtcaccc atcagggcct gagctcgccc gtcacaaaga gcttcaacag gggagagtgt      660
tgactcgag                                                              669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51

```
gatattgtga tgacccagac tccactctcc ctgcccgtca cccctggaga gccggcctcc       60
atctcctgca gtccagtca gagtctttta gctagtggca accaaaataa ctacttggcc       120
tggcacctgc agaagccagg gcagtctcca cagatgctga tcatttgggc atccactagg      180
gtatctggag tcccagacag gttcagtggc agtgggtcag gcactgattt cacactgaaa      240
atcagcaggg tggaggctga ggatgttgga gtttattact gccagcagtc ctacagcgct      300
ccgctcacgt tcggacaggg taccaagctg gagctcaaac gtacggtggc tgcaccatct      360
```

```
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc      600 gaagtcaccc atcagggcct gagctcgccc gtcacaaaga gcttcaacag gggagagtgt      660
tgactcgag                                                              669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

```
gacatcgtga tgacccagtc tccagactcc ctggctgtgt ctctgggcga gagggccacc       60
atcaactgca agtccagcca gagtctttta gctagcggca ccaaaataa ctacttagct      120 tggtaccagc agaaaccagg acagcctcct aagctgctca ttatttgggc atctacccgg      180
gtatccgggg tccctgaccg attcagtggc agcgggtctg ggacagattt cactctcacc      240
atcagcagcc tgcaggctga agatgtggca gtttattact gtcagcaatc ctatagtgct      300
cctctcacgt tcggaggcgg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc      600 gaagtcaccc atcagggcct gagctcgccc gtcacaaaga gcttcaacag gggagagtgt      660
tgactcgag                                                              669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

```
gatatccaga tgacccagtc cccgagctcc ctgtccgcct ctgtgggcga tagggtcacc       60
atcacctgca agtccagtca gagtctttta gctagtggca accaaaataa ctacttggcc      120
tggcaccaac agaaaccagg aaaagctccg aaaatgctga ttatttgggc atccactagg      180
gtatctggag tcccttctcg cttctctgga tccgggtctg ggacggattt cactctgacc      240
atcagcagtc tgcagccgga agacttcgca acttattact gtcagcagtc ctacagcgct      300
ccgctcacgt tcggacaggg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc      600 gaagtcaccc atcagggcct gagctcgccc gtcacaaaga gcttcaacag gggagagtgt      660
tgactcgag                                                              669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55
gctagcgttt tagcagaagt tcaattggtt gaatctggtg gtggtttggt tcaaccaggt        60
ggttctttga gattgtcttg tgctgcttct ggttttactt tcaccgatta ttacatgtcc       120
tgggttagac aagctccagg taaaggtttg aatggttgg gtttcattag aaacaaggct        180
aacggttaca ctaccgaata ttctgcttct gttaaggta gattcaccat ttctagagac        240
aactctaaga cacccttgta cttgcaaatg aactccttga gagctgaaga tactgctgtt       300
tattactgcg ctagagataa ttggtttgct tattggggtc aaggtacttt ggttactgtt       360
tcttctggcc tcgggggcct cggaggagga ggtagtggcg gaggaggctc cggtggatcc       420
agcggtgtgg gttccgatat tcaaatgacc caatctccat cttctttgtc tgcttcagtt       480
ggtgatagag ttaccattac ttgtaagtcc tcccaatctt tgttggcttc tggtaatcag       540
aacaattact ggcttggca tcaacaaaaa ccaggtaaag ctccaaagat gttgattatt        600
tgggcttcta ccagagtttc tggtgttcca tctagatttt ctggttctgg ttccggtact       660 gatttttactt tgaccatttc atccttgcaa ccagaagatt tcgctactta ctactgtcaa      720
caatcttact ctgctccatt gactttttggt caaggtacaa aggtcgaaat caagagagaa      780
ttcggtaagc ctatccctaa ccctctcctc ggtctcgatt ctacgggtgg tggtggatct       840
ggtggtggtg ttctggtgg tggtggttct caggaactga caactatatg cgagcaaatc       900
ccctcaccaa ctttagaatc gacgccgtac tctttgtcaa cgactactat tttggccaac      960
gggaaggcaa tgcaaggagt ttttgaatat tacaaatcag taacgtttgt cagtaattgc      1020
ggttctcacc cctcaacaac tagcaaaggc agccccataa acacacagta tgtttttga      1080 gtttaaac                                                              1088

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:

```
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt    60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagtttttt agccttattt ctggggtaat taatcagcga agcgatgatt tttgatctat   300
taacagatat ataaatgcaa aaactgcata accactttaa ctaatacttt caacattttc   360
ggtttgtatt acttcttatt caaatgtaat aaaagtatca acaaaaaatt gttaatatac   420
ctctatactt taacgtcaag gagaaaaaac cccggatcgg actactagca gctgtaatac   480
gactcactat agggaatatt aagctaattc tacttcatac attttcaatt aagatgcagt   540
tacttcgctg ttttcaata ttttctgtta ttgctagcgt tttagcagaa gttcaattgg   600
ttgaatctgg tggtggtttg gttcaaccag gtggttcttt gagattgtct tgtgctgctt   660
ctggttttac tttcaccgat tattacatgt cctgggttag acaagctcca ggtaaaggtt   720
tggaatggtt gggtttcatt agaaacaagg ctaacggtta cactaccgaa tattctgctt   780
ctgttaaggg tagattcacc atttctagag acaactctaa gaacaccttg tacttgcaaa   840
tgaactcctt gagagctgaa gatactgctg tttattactg cgctagagat aattggtttg   900
cttattgggg tcaaggtact ttggttactg tttcttctgg cctcgggggc ctcggaggag   960
gaggtagtgg cggaggaggc tccggtggat ccagcgtgt gggttccgat attcaaatga   1020
cccaatctcc atcttctttg tctgcttcag ttggtgatag agttaccatt acttgtaagt   1080
cctcccaatc tttgttggct tctggtaatc agaacaatta cttggcttgg catcaacaaa   1140
aaccaggtaa agctccaaag atgttgatta tttgggcttc taccagagtt tctggtgttc   1200
catctagatt ttctggttct ggttccggta ctgattttac tttgaccatt tcatccttgc   1260
```

```
aaccagaaga tttcgctact tactactgtc aacaatctta ctctgctcca ttgactttig   1320
gtcaaggtac aaaggtcgaa atcaagagag aattcggtaa gcctatccct aaccctctcc   1380
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga gttttttgaat  1560
attacaaatc agtaacgttt gtcagtaatt gcggttctca ccctcaaca actagcaaag    1620
gcagccccat aaacacacag tatgtttttt gagtttaaac ccgctgatct gataacaaca   1680
gtgtagatgt aacaaaatcg actttgttcc cactgtactt ttagctcgta caaaatacaa   1740
tatactttc  atttctccgt aaacaacatg ttttcccatg taatatcctt ttctattttt   1800
cgttccgtta ccaactttac acatacttta tatagctatt cacttctata cactaaaaaa   1860
ctaagacaat tttaattttg ctgcctgcca tatttcaatt tgttataaat tcctataatt   1920
tatcctatta gtagctaaaa aaagatgaat gtgaatcgaa tcctaagaga attgggcaag   1980
tgcacaaaca atacttaaat aaatactact cagtaataac ctatttctta gcattttiga   2040
cgaaatttgc tattttgtta gagtctttta caccatttgt ctccacacct ccgcttacat    2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaaagttca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa aacatcctcc ttaggttgat   2460
tacgaaacac gccaaccaag tatttcggag tgcctgaact atttttatat gcttttacaa   2520
gacttgaaat tttccttgca ataaccgggt caattgttct ctttctattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctccttt  cttttttcga ccgaatttct tgaagacgaa agggcctcgt   2820
gatacgccta tttttatagg ttaatgtcat gataataatg gtttcttagg acggatcgct   2880
tgcctgtaac ttacacgcgc ctcgtatctt ttaatgatgg aataatttgg gaatttactc   2940
tgtgtttatt tattttatg  ttttgtattt ggattttaga agtaaataa  agaaggtaga   3000
agagttacgg aatgaagaaa aaaaaataaa caaggtttta aaaatttca  acaaaaagcg   3060
tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaaggt agtatttgtt   3240
ggcgatcccc ctagagtctt ttacatcttc ggaaaacaaa aactattttt tctttaattt   3300
cttttttttac tttctatttt taatttatat atttatatta aaaatttaa  attataatta   3360
ttttttatagc acgtgatgaa aaggaccag  gtggcactt  tcggggaaat gtgcgcggaa   3420
cccctatttg tttatttttc taaatacatt caaatatgta tccgctcatg agacaataac   3480
cctgataaat gcttcaataa tattgaaaaa ggaagagtat gagtattcaa catttccgtg   3540
tcgcccttat tccctttttt gcggcatttt gccttcctgt ttttgctcac ccagaaacgc   3600
```

| tggtgaaagt aaaagatgct gaagatcagt gggtgcacg agtgggttac atcgaactgg | 3660 |
| atctcaacag cggtaagatc cttgagagtt tcgccccga agaacgtttt ccaatgatga | 3720 |
| gcacttttaa agttctgcta tgtggcgcgg tattatcccg tgttgacgcc gggcaagagc | 3780 |
| aactcggtcg ccgcatacac tattctcaga atgacttggt tgagtactca ccagtcacag | 3840 |
| aaaagcatct tacggatggc atgacagtaa gagaattatg cagtgctgcc ataaccatga | 3900 |
| gtgataacac tgcggccaac ttacttctga acgatcgg aggaccgaag gagctaaccg | 3960 |
| cttttttgca caacatgggg gatcatgtaa ctcgccttga tcgttgggaa ccggagctga | 4020 |
| atgaagccat accaaacgac gagcgtgaca ccacgatgcc tgtagcaatg gcaacaacgt | 4080 |
| tgcgcaaact attaactggc gaactactta ctctagcttc ccggcaacaa ttaatagact | 4140 |
| ggatggaggc ggataaagtt gcaggaccac ttctgcgctc ggcccttccg gctggctggt | 4200 |
| ttattgctga taaatctgga gccggtgagc gtgggtctcg cggtatcatt gcagcactgg | 4260 |
| ggccagatgg taagccctcc cgtatcgtag ttatctacac gacgggcagt caggcaacta | 4320 |
| tggatgaacg aaatagacag atcgctgaga taggtgcctc actgattaag cattggtaac | 4380 |
| tgtcagacca agtttactca tatatacttt agattgattt aaaacttcat ttttaattta | 4440 |
| aaaggatcta ggtgaagatc cttttgata atctcatgac caaaatccct taacgtgagt | 4500 |
| tttcgttcca ctgagcgtca gaccccgtag aaaagatcaa aggatcttct tgagatcctt | 4560 |
| tttttctgcg cgtaatctgc tgcttgcaaa caaaaaaacc accgctacca gcggtggttt | 4620 |
| gtttgccgga tcaagagcta ccaactcttt ttccgaaggt aactggcttc agcagagcgc | 4680 |
| agataccaaa tactgtcctt ctagtgtagc cgtagttagg ccaccacttc aagaactctg | 4740 |
| tagcaccgcc tacatacctc gctctgctaa tcctgttacc agtggctgct gccagtggcg | 4800 |
| ataagtcgtg tcttaccggg ttggactcaa gacgatagtt accggataag cgcagcggt | 4860 |
| cgggctgaac ggggggttcg tgcacacagc ccagcttgga gcgaacgacc tacaccgaac | 4920 |
| tgagatacct acagcgtgag cattgagaaa gcgccacgct tcccgaaggg agaaaggcgg | 4980 |
| acaggtatcc ggtaagcggc agggtcggaa caggagagcg cacgagggag cttccagggg | 5040 |
| ggaacgcctg gtatctttat agtcctgtcg ggtttcgcca cctctgactt gagcgtcgat | 5100 |
| ttttgtgatg ctcgtcaggg gggccgagcc tatggaaaaa cgccagcaac gcggcctttt | 5160 |
| tacggttcct ggccttttgc tggccttttg ctcacatgtt ctttcctgcg ttatcccctg | 5220 |
| attctgtgga taaccgtatt accgcctttg agtgagctga taccgctcgc cgcagccgaa | 5280 |
| cgaccgagcg cagcgagtca gtgagcgagg aagcggaaga gcgcccaata cgcaaaccgc | 5340 |
| ctctccccgc gcgttggccg attcattaat gcagctggca cgacaggttt cccgactgga | 5400 |
| aagcgggcag tgagcgcaac gcaattaatg tgagttacct cactcattag gcaccccagg | 5460 |
| ctttacactt tatgcttccg gctcctatgt tgtgtggaat tgtgagcgga taacaatttc | 5520 |
| acacaggaaa cagctatgac catgattacg ccaagctcgg aattaaccct cactaaaggg | 5580 |
| aacaaaagct ggctagt | 5597 |

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58

```
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtcagcagtc ctacagccgc ccgtacacgt tcggacaggg taccaaggtg   420
gagatcaaac gtacg                                                    435
```

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59

```
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg gacggattt cactctgacc atcagcagtc tgcagccgga agacttcgca   360
acttattact gtgggcagtc ctacagccgt ccgctcacgt tcggacaggg taccaaggtg   420
gagatcaaac gtacg                                                    435
```

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60

```
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg gacggattt cactctgacc atcagcagtc tgcagccgga agacttcgca   360
```

```
acttattact gtgcacagtc ctacagccat ccgttctctt tcggacaggg taccaaggtg    420
gagatcaaac gtacg                                                    435

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtctttta     180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggatttt cactctgacc atcagcagtc tgcagccgga agacttcgca    360
acttattact gtcagcagtc ctacagccgc ccgtttacgt tcggacaggg taccaaggtg    420
gagatcaaac gtacg                                                    435

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, U6-HC7 hinge and constant region of human IgG1

<400> SEQUENCE: 62

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
```

|     |     |     |     | 195 |     |     |     | 200 |     |     |     | 205 |     |     |
|-----|-----|-----|-----|-----|-----|-----|-----|-----|-----|-----|-----|-----|-----|-----|
| Ser | Leu | Gly | Thr | Gln | Thr | Tyr | Ile | Cys | Asn | Val | Asn | His | Lys | Pro | Ser
210

Asn Thr Lys Val Asp Lys Val Glu Pro Lys Ser Cys Asp Cys His
225                     230                     235                     240

Cys Pro Pro Cys Pro Ala Pro Glu Leu Leu Gly Gly Pro Ser Val Phe
                245                     250                     255

Leu Phe Pro Pro Lys Pro Lys Asp Thr Leu Met Ile Ser Arg Thr Pro
                260                     265                     270

Glu Val Thr Cys Val Val Val Asp Val Ser His Glu Asp Pro Glu Val
                275                     280                     285

Lys Phe Asn Trp Tyr Val Asp Gly Val Glu Val His Asn Ala Lys Thr
                290                     295                     300

Lys Pro Arg Glu Glu Gln Tyr Asn Ser Thr Tyr Arg Val Val Ser Val
305                     310                     315                     320

Leu Thr Val Leu His Gln Asp Trp Leu Asn Gly Lys Glu Tyr Lys Cys
                325                     330                     335

Lys Val Ser Asn Lys Ala Leu Pro Ala Pro Ile Glu Lys Thr Ile Ser
                340                     345                     350

Lys Ala Lys Gly Gln Pro Arg Glu Pro Gln Val Tyr Thr Leu Pro Pro
                355                     360                     365

Ser Arg Glu Glu Met Thr Lys Asn Gln Val Ser Leu Thr Cys Leu Val
370                     375                     380

Lys Gly Phe Tyr Pro Ser Asp Ile Ala Val Glu Trp Glu Ser Asn Gly
385                     390                     395                     400

Gln Pro Glu Asn Asn Tyr Lys Thr Thr Pro Pro Val Leu Asp Ser Asp
                405                     410                     415

Gly Ser Phe Phe Leu Tyr Ser Lys Leu Thr Val Asp Lys Ser Arg Trp
                420                     425                     430

Gln Gln Gly Asn Val Phe Ser Cys Ser Val Met His Glu Ala Leu His
                435                     440                     445

Asn His Tyr Thr Gln Lys Ser Leu Ser Leu Ser Pro Gly Lys
450                     455                     460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7
      hinge and constant region of human IgG1

<400> SEQUENCE: 63
gaattcgccg ccaccatgga atggagctgg gttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta taagcagaga taattccaaa   300
aacacactgt acctgcagat gaacagcctg cgtgctgagg acactgccgt ctattattgt   360
gctagagata actggtttgc ttactggggc caagggactc tggtcaccgt ctcctcggct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540

```
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga tgaccaag    1140 aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg   1320 aacgtcttct catgctccgt gatgcatgag gctctgcaca accactacac gcagaagagc   1380
ctctccctgt ctccgggtaa atgactcgag                                    1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of human
      IgG1

<400> SEQUENCE: 64

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
                20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190
```

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
            210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
            450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2
      hinge and constant region of human IgG1

<400> SEQUENCE: 65
gaattcgccg ccaccatgga atggagctgg gttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480

```
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgccccc ctgcccagca cctgaactcc tgggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc tcccgtgct ggactccgac    1260
ggctccttct tcctctacag caagctcacc gtggacaaga gcaggtggca gcagggaac    1320
gtcttctcat gctccgtgat gcatgaggct ctgcacaacc actacacgca gaagagcctc    1380
tccctgtctc cgggtaaatg actcgag                                       1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
of huAbF46-H4-A1, human IgG2 hinge and constant region of human
IgG2

<400> SEQUENCE: 66

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

```
Ser Ser Gly Leu Tyr Ser Leu Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
            245                 250                 255

Pro Pro Lys Pro Lys Asp Thr Leu Met Ile Ser Arg Thr Pro Glu Val
        260                 265                 270

Thr Cys Val Val Val Asp Val Ser His Glu Asp Pro Glu Val Gln Phe
    275                 280                 285

Asn Trp Tyr Val Asp Gly Val Glu Val His Asn Ala Lys Thr Lys Pro
290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
            325                 330                 335

Ser Asn Lys Gly Leu Pro Ala Pro Ile Glu Lys Thr Ile Ser Lys Thr
        340                 345                 350

Lys Gly Gln Pro Arg Glu Pro Gln Val Tyr Thr Leu Pro Pro Ser Arg
    355                 360                 365

Glu Glu Met Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
            405                 410                 415

Phe Phe Leu Tyr Ser Lys Leu Thr Val Asp Lys Ser Arg Trp Gln Gln
        420                 425                 430

Gly Asn Val Phe Ser Cys Ser Val Met His Glu Ala Leu His Asn His
    435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2
      hinge and constant region of human IgG2

<400> SEQUENCE: 67
gaattcgccg ccaccatgga atggagctgg gtttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta agcagaga taattccaaa      300 aacacactgt acctgcagat gaacagcctg cgtgctgagg acactgccgt ctattattgt     360
gctagagata actggtttgc ttactggggc caagggactc tggtcaccgt ctcctcggct     420
agcaccaagg gcccatcggt cttccccctg gcgccctgct ccaggagcac ctccgagagc     480
```

```
acagcggccc tgggctgcct ggtcaaggac tacttcccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caagggcag   1080 ccccgagaac acaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                         1404

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1(H36Y) and human kappa constant region

<400> SEQUENCE: 68

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp Tyr Gln Gln
        50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190
```

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and
      human kappa constant region

<400> SEQUENCE: 69
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtctttag     180 ctagtggcaa ccaaaataac tacttggcct ggtaccaaca gaaaccagga aaagctccga     240
aaatgctgat tatttgggca tccactaggg tatctggagt cccttctcgc ttctctggat     300
ccgggtctgg gacggatttc actctgacca tcagcagtct gcagccggaa gacttcgcaa     360
cttattactg tcagcagtcc tacagccgcc gtacacgttc ggacagggt accaaggtgg     420 agatcaaacg tacggtggct gcaccatctg tcttcatctt cccgccatct gatgagcagt     480
tgaaatctgg aactgcctct gttgtgtgcc tgctgaataa cttctatccc agagaggcca     540
aagtacagtg gaaggtggat aacgccctcc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                            758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1 and human kappa constant region

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

```
Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)

<400> SEQUENCE: 74

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
```

<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76

```
gaattcgccg ccaccatgga atggagctgg gttttctctcg taacactttt aaatggtatc    60
cagtgtgagg tgaagctggt ggagtctgga ggaggcttgg tacagcctgg gggttctctg   120
agactctcct gtgcaacttc tgggttcacc ttcactgatt actacatgag ctgggtccgc   180
cagcctccag aaaggcact tgagtggttg ggttttatta gaaacaaagc taatggttac   240
acaacagagt acagtgcatc tgtgaagggt cggttcacca tctccagaga taattcccaa   300
agcatcctct atcttcaaat ggacaccctg agagctgagg acagtgccac ttattactgt   360
gcaagagata actggtttgc ttactggggc caagggactc tggtcactgt ctctgcagct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttcccccc aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagccgc gggaggagca gtacaacagc   960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggaggagatg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga ctcgag                             1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)

<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atgattcac aggcccaggt cctcatgttg      60
ctgctgctat cggtatctgg tacctgtgga gacattttga tgacccagtc tccatcctcc    120
ctgactgtgt cagcaggaga aggtcact  atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt cggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                          759
```

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

```
atgaaggccc ccgctgtgct tgcacctggc atcctcgtgc tcctgtttac cttggtgcag    60
aggagcaatg gggagtgtaa agaggcacta gcaaagtccg agatgaatgt gaatatgaag   120
tatcagcttc ccaacttcac cgcggaaaca cccatccaga atgtcattct acatgagcat   180
cacattttcc ttggtgccac taactacatt tatgttttaa atgaggaaga ccttcagaag   240
gttgctgagt acaagactgg gcctgtgctg gaacacccag attgtttccc atgtcaggac   300
tgcagcagca agccaatttt atcaggaggt gtttggaaag ataacatcaa catggctcta   360
gttgtcgaca cctactatga tgatcaactc attagctgtg gcagcgtcaa cagagggacc   420
tgccagcgac atgtctttcc ccacaatcat actgctgaca tacagtcgga ggttcactgc   480
atattctccc cacagataga agagcccagc cagtgtcctg actgtgtggt gagcgccctg   540
ggagccaaag tccttttcatc tgtaaaggac cggttcatca acttctttgt aggcaatacc   600
```

```
ataaattctt cttatttccc agatcatcca ttgcattcga tatcagtgag aaggctaaag    660
gaaacgaaag atggttttat gttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaagag atccacaaag aaggaagtgt taatatact tcaggctgcg    960 tatgtcagca agcctgggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcattttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtggctggga ctttggattt cggaggaata taaatttga tttaaagaaa   1800 actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg aaaaacatg tactttaaaa   2100 agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg gaaaaaacct gaattcagtt agtgtcccga gaatggtcat aaatgtgcat   2340
gaagcaggaa ggaactttac agtggcatgt caacatcgct ctaattcaga gataatctgt   2400
tgtaccactc cttcccctgca acagctgaat ctgcaactcc ccctgaaaac caaagccttt   2460
ttcatgttag atgggatcct ttccaaatac tttgatctca tttatgtaca taatcctgtg   2520
tttaagcctt ttgaaaagcc agtgatgatc tcaatgggca atgaaaatgt actgaaaatt   2580
aagggaaatg atattgaccc tgaagcagtt aaaggtgaag tgttaaaagt tggaaataag   2640
agctgtgaga atatacactt acattctgaa gccgttttat gcacggtccc caatgacctg   2700
ctgaaattga acagcgagct aaatatagag tggaagcaag caatttcttc aaccgtcctt   2760
ggaaaagtaa tagttcaacc agatcagaat ttcacaggat tgattgctgg tgttgtctca   2820
atatcaacag cactgttatt actacttggg ttttttcctgt ggctgaaaaa gagaaagcaa   2880
attaaagatc tgggcagtga attagttcgc tacgatgcaa gagtacacac tcctcatttg   2940
```

```
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata acgctgatga tgaggtggac    4140
acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Val Gly Asn Thr
    130                 135                 140
```

-continued

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
                20                  25                  30

Pro Pro Phe Val Gln Cys Gly Trp Cys His Asp Lys Cys Val Arg Ser
            35                  40                  45

Glu Glu Cys Leu Ser Gly Thr Trp Thr Gln Gln Ile Cys Leu Pro Ala
        50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
            85                  90                  95

Asp Leu Lys Lys Thr Arg Val Leu Leu Gly Asn Glu Ser Cys Thr Leu
        100                 105                 110

Thr Leu Ser Glu Ser Thr Met Asn Thr Leu Lys Cys Thr Val Gly Pro
    115                 120                 125

Ala Met Asn Lys His Phe Asn Met Ser Ile Ile Ile Ser Asn Gly His
130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450

<210> SEQ ID NO 81
<211> LENGTH: 313
<212> TYPE: PRT

<213> ORGANISM: Artificial Sequence
<220> FEATURE:
<223> OTHER INFORMATION: Synthetic TyrKc domain of c-Met

<400> SEQUENCE: 81

```
Val His Phe Asn Glu Val Ile Gly Arg Gly His Phe Gly Cys Val Tyr
 1               5                  10                  15

His Gly Thr Leu Leu Asp Asn Asp Gly Lys Lys Ile His Cys Ala Val
             20                  25                  30

Lys Ser Leu Asn Arg Ile Thr Asp Ile Gly Glu Val Ser Gln Phe Leu
         35                  40                  45

Thr Glu Gly Ile Ile Met Lys Asp Phe Ser His Pro Asn Val Leu Ser
 50                  55                  60

Leu Leu Gly Ile Cys Leu Arg Ser Glu Gly Ser Pro Leu Val Val Leu
 65                  70                  75                  80

Pro Tyr Met Lys His Gly Asp Leu Arg Asn Phe Ile Arg Asn Glu Thr
                 85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain of c-Met

<400> SEQUENCE: 82

```
ctacatgagc atcacatttt ccttggtgcc actaactaca tttatgtttt aaatgaggaa    60
```

| | | | | |
|---|---|---|---|---|
| gaccttcaga | aggttgctga | gtacaagact | gggcctgtgc | tggaacaccc agattgtttc | 120 |
| ccatgtcagg | actgcagcag | caaagccaat | ttatcaggag | gtgtttggaa agataacatc | 180 |
| aacatggctc | tagttgtcga | cacctactat | gatgatcaac | tcattagctg tggcagcgtc | 240 |
| aacagaggga | cctgccagcg | acatgtcttt | ccccacaatc | atactgctga catacagtcg | 300 |
| gaggttcact | gcatattctc | cccacagata | gaagagccca | gccagtgtcc tgactgtgtg | 360 |
| gtgagcgccc | tgggagccaa | agtcctttca | tctgtaaagg | accggttcat caacttcttt | 420 |
| gtaggcaata | ccataaattc | ttcttatttc | ccagatcatc | cattgcattc gatatcagtg | 480 |
| agaaggctaa | aggaaacgaa | agatggtttt | atgtttttga | cggaccagtc ctacattgat | 540 |
| gttttacctg | agttcagaga | ttcttacccc | attaagtatg | tccatgcctt tgaaagcaac | 600 |
| aattttattt | acttcttgac | ggtccaaagg | gaaactctag | atgctcagac ttttcacaca | 660 |
| agaataatca | ggttctgttc | cataaactct | ggattgcatt | cctacatgga aatgcctctg | 720 |
| gagtgtattc | tcacagaaaa | gagaaaaaag | agatccacaa | agaaggaagt gtttaatata | 780 |
| cttcaggctg | cgtatgtcag | caagcctggg | gcccagcttg | ctagacaaat aggagccagc | 840 |
| ctgaatgatg | acattctttt | cggggtgttc | gcacaaagca | agccagattc tgccgaacca | 900 |
| atggatcgat | ctgccatgtg | tgcattccct | atcaaatatg | tcaacgactt cttcaacaag | 960 |
| atcgtcaaca | aaacaatgt | gagatgtctc | cagcattttt | acggacccaa tcatgagcac | 1020 |
| tgctttaata | ggacacttct | gagaaattca | tcaggctgtg | aagcgcgccg tgatgaatat | 1080 |
| cgaacagagt | ttaccacagc | tttgcagcgc | gttgacttat | tcatgggtca attcagcgaa | 1140 |
| gtcctcttaa | catctatatc | caccttcatt | aaaggagacc | tcaccatagc taatcttggg | 1200 |
| acatcagagg | gtcgcttcat | gcaggttgtg | gtttctcgat | caggaccatc aacccctcat | 1260 |
| gtgaatttc | tcctggactc | ccatccagtg | tctccagaag | tgattgtgga gcatacatta | 1320 |
| aaccaaaatg | gc | | | | 1332 |

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
      domain of c-Met

<400> SEQUENCE: 83

| | | | | |
|---|---|---|---|---|
| tacacactgg | ttatcactgg | gaagaagatc | acgaagatcc | cattgaatgg cttgggctgc | 60 |
| agacatttcc | agtcctgcag | tcaatgcctc | tctgccccac | cctttgttca gtgtggctgg | 120 |
| tgccacgaca | aatgtgtgcg | atcggaggaa | tgcctgagcg | ggacatggac tcaacagatc | 180 |
| tgtctgcctg | caatctacaa | ggttttccca | aatagtgcac | cccttgaagg agggacaagg | 240 |
| ctgaccatat | gtggctggga | ctttggattt | cggaggaata | taaatttga tttaaagaaa | 300 |
| actagagttc | tccttggaaa | tgagagctgc | accttgactt | taagtgagag cacgatgaat | 360 |
| acattgaaat | gcacagttgg | tcctgccatg | aataagcatt | tcaatatgtc cataattatt | 420 |
| tcaaatggcc | acgggacaac | acaatacagt | acattctcct | atgtggatcc tgtaataaca | 480 |
| agtatttcgc | cgaaatacgg | tcctatggct | ggtggcactt | tacttacttt aactggaaat | 540 |
| tacctaaaca | gtgggaattc | tagacacatt | tcaattggtg | gaaaaacatg tactttaaaa | 600 |
| agtgtgtcaa | acagtattct | tgaatgttat | accccagccc | aaaccatttc aactgagttt | 660 |
| gctgttaaat | tgaaaattga | cttagccaac | cgagagacaa | gcatcttcag ttaccgtgaa | 720 |

```
gatcccattg tctatgaaat tcatccaacc aaatctttta ttagtggtgg gagcacaata      780
acaggtgttg ggaaaaacct gaattcagtt agtgtcccga gaatggtcat aaatgtgcat      840
gaagcaggaa ggaactttac agtggcatgt caacatcgct ctaattcaga gataatctgt      900
tgtaccactc cttccctgca acagctgaat ctgcaactcc ccctgaaaac caaagccttt      960
ttcatgttag atgggatcct ttccaaatac tttgatctca tttatgtaca taatcctgtg     1020
tttaagcctt ttgaaaagcc agtgatgatc tcaatgggca atgaaaatgt actggaaatt     1080
aagggaaatg atattgaccc tgaagcagtt aaaggtgaag tgttaaaagt tggaaataag     1140
agctgtgaga atatacactt acattctgaa gccgttttat gcacggtccc caatgacctg     1200
ctgaaattga acagcgagct aaatatagag tggaagcaag caatttcttc aaccgtcctt     1260
ggaaaagtaa tagttcaacc agatcagaat ttcacagga                            1299
```

```
<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain
      of c-Met

<400> SEQUENCE: 84
```

```
gtgcatttca atgaagtcat aggaagaggg cattttggtt gtgtatatca tgggactttg       60
ttggacaatg atggcaagaa aattcactgt gctgtgaaat ccttgaacag atcactgac       120 ataggagaag tttcccaatt tctgaccgag ggaatcatca tgaaagattt tagtcatccc      180
aatgtcctct cgctcctggg aatctgcctg cgaagtgaag ggtctccgct ggtggtccta      240
ccatacatga acatggaga tcttcgaaat tcattcgaa atgagactca taatccaact       300
gtaaaagatc ttattggctt tggtcttcaa gtagccaaag catgaaata tcttgcaagc      360 aaaaagtttg tccacagaga cttggctgca agaaactgta tgctggatga aaaattcaca      420
gtcaaggttg ctgattttgg tcttgccaga gacatgtatg ataaagaata ctatagtgta      480
cacaacaaaa caggtgcaaa gctgccagtg aagtggatgg cttttgaaag tctgcaaact      540
caaaagttta ccaccaagtc agatgtgtgg tcctttggcg tgctcctctg ggagctgatg      600
acaagaggag cccccaccta tcctgacgta aacacctttg atataactgt ttacttgttg      660
caagggagaa gactcctaca acccgaatac tgcccagacc ccttatatga agtaatgcta      720
aaatgctggc accctaaagc cgaaatgcgc ccatcctttt ctgaactggt gtcccggata      780
tcagcgatct tctctacttt cattggggag cactatgtcc atgtgaacgc tacttatgtg      840
aacgtaaaat gtgtcgctcc gtatccttct ctgttgtcat cagaagataa cgctgatgat      900
gaggtggaca cacgaccagc ctccttctgg gagacatca                              939
```

```
<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met
      antibody

<400> SEQUENCE: 85

Asp Asn Trp Phe Ala Tyr Trp Gly Gln Gly Thr Leu Val
1               5                   10

<210> SEQ ID NO 86
```

```
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110
```

-continued

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
1               5                   10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT

<213> ORGANISM: Artificial Sequence
<220> FEATURE:
<223> OTHER INFORMATION: Synthetic heavy chain variable region of AT-VH5

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
            115
```

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg
```

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

```
Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30
```

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

```
Ser Tyr Ser Ala Pro Leu Thr Phe Gly Gln Gly Thr Lys Leu Glu Ile
            100                 105                 110
Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
1               5                   10

<210> SEQ ID NO 103
```

```
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
1               5                   10                  15
Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
```

```
                85                  90                  95

Ser Tyr Ser Arg Pro Tyr Thr Phe Gly Gln Gly Thr Lys Val Glu Ile
                100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
                20                  25                  30

Gly Asn Gln Asn Asn Tyr Leu Ala Trp Tyr Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 109
<211> LENGTH: 120
<212> TYPE: PRT
<213> ORGANISM: Artificial Sequence
<220> FEATURE:
<223> OTHER INFORMATION: Synthetic heavy-chain variable region of
      anti-EGFR antibody

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
                20                  25                  30

Lys Ile His Trp Val Arg Gln Ala Pro Gly Gln Gly Leu Glu Trp Met
        35                  40                  45
```

```
Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
                100                 105                 110

Gly Thr Thr Val Thr Val Ser Ser
                115                 120

<210> SEQ ID NO 110
<211> LENGTH: 360
<212> TYPE: DNA
<213> ORGANISM: Artificial Sequence
<220> FEATURE:
<223> OTHER INFORMATION: Synthetic DNA encoding heavy-chain variable
      region of anti-EGFR antibody

<400> SEQUENCE: 110
caggtgcagc tggtgcagtc tggggctgag gtgaagaagc ctgggtcctc ggtgaaggtc      60
tcctgcaagg cctctggttt cacattcact gactacaaga tacactgggt gcgacaggcc     120
cctggacaag gctcgagtg atgggatat ttcaaccctaa acagcggtta tagtacctac      180
gcacagaagt tccagggcag ggtcaccatt accgcggaca aatccacgag cacagcctac     240
atggagctga gcagcctgag atctgaggac acggccgtgt attactgtgc gagactatcc     300
ccaggcggtt actatgttat ggatgcctgg ggccaaggga ccaccgtgac cgtctcctca     360

<210> SEQ ID NO 111
<211> LENGTH: 108
<212> TYPE: PRT
<213> ORGANISM: Artificial Sequence
<220> FEATURE:
<223> OTHER INFORMATION: Synthetic light-chain variable region of
      anti-EGFR antibody

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
                20                  25                  30

Leu Asn Trp Tyr Gln Gln Lys Pro Gly Lys Ala Pro Lys Arg Leu Ile
            35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr
                100                 105

<210> SEQ ID NO 112
<211> LENGTH: 324
<212> TYPE: DNA
<213> ORGANISM: Artificial Sequence
<220> FEATURE:
<223> OTHER INFORMATION: Synthetic DNA encoding light-chain variable
      region of anti-EGFR antibody
```

<400> SEQUENCE: 112

```
gatatccaga tgacccagtc tccatcctcc ctgtctgcat ctgtcggaga ccgggtcacc      60
atcacctgcc gggcaagtca gggcattaac aattacttaa attggtacca gcagaagcca     120
gggaaagccc ctaagcgcct gatctataat accaacaact tgcagacagg cgtcccatca     180
aggttcagcg gcagtggatc cgggacagaa ttcactctca ccatcagcag cctgcagcct     240
gaagattttg ccacctatta ctgcttgcag cataatagtt ttcccacgtt tggccagggc     300
accaagctcg agatcaagcg tacg                                            324
```

<210> SEQ ID NO 113
<211> LENGTH: 120
<212> TYPE: PRT
<213> ORGANISM: Artificial Sequence
<220> FEATURE:
<223> OTHER INFORMATION: Synthetic modified heavy-chain variable region of anti-EGFR antibody

<400> SEQUENCE: 113

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Cys Leu Glu Trp Met
        35                  40                  45

Gly Tyr Ile Asn Pro Asn Ser Gly Tyr Ser Thr Tyr Ala Ser Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120
```

<210> SEQ ID NO 114
<211> LENGTH: 108
<212> TYPE: PRT
<213> ORGANISM: Artificial Sequence
<220> FEATURE:
<223> OTHER INFORMATION: Synthetic modified light-chain variable region of anti-EGFR antibody

<400> SEQUENCE: 114

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Glu Ala Thr Tyr Tyr Cys Leu Gln His Asn Ser Phe Pro Thr
                85                  90                  95
```

Phe Gly Gln Cys Thr Lys Leu Glu Ile Lys Arg Thr
            100                 105

<210> SEQ ID NO 115
<211> LENGTH: 5
<212> TYPE: PRT
<213> ORGANISM: Artificial Sequence
<220> FEATURE:
<223> OTHER INFORMATION: Synthetic CDR-H1 of anti-EGFR scFv

<400> SEQUENCE: 115

Asn Tyr Asp Met Ser
1               5

<210> SEQ ID NO 116
<211> LENGTH: 17
<212> TYPE: PRT
<213> ORGANISM: Artificial Sequence
<220> FEATURE:
<223> OTHER INFORMATION: Synthetic CDR-H2 of anti-EGFR scFv

<400> SEQUENCE: 116

Gly Ile Ser His Ser Ser Gly Ser Lys Tyr Tyr Ala Asp Ser Val Lys
1               5                   10                  15

Gly

<210> SEQ ID NO 117
<211> LENGTH: 13
<212> TYPE: PRT
<213> ORGANISM: Artificial Sequence
<220> FEATURE:
<223> OTHER INFORMATION: Synthetic CDR-H3 of anti-EGFR scFv

<400> SEQUENCE: 117

Lys Asp Ala Thr Pro Arg Pro Leu Lys Pro Phe Asp Tyr
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Synthetic CDR-L1 of anti-EGFR scFv

<400> SEQUENCE: 118

Thr Gly Ser Ser Ser Asn Ile Gly Asn Asn Asp Val Ser
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Synthetic CDR-L2 of anti-EGFR scFv

<400> SEQUENCE: 119

Asp Asp Asn Lys Arg Pro Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic CDR-L3 of anti-EGFR scFv

<400> SEQUENCE: 120

```
Gly Ser Trp Asp Ala Ser Leu Asn Ala
1               5

<210> SEQ ID NO 121
<211> LENGTH: 121
<212> TYPE: PRT
<213> ORGANISM: Artificial Sequence
<220> FEATURE:
<223> OTHER INFORMATION: Synthetic Heavy chain variable region of
      anti-EGFR scFv

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Gly Ile Ser His Ser Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Thr Pro Arg Pro Leu Lys Pro Phe Asp Tyr Trp Gly
            100                 105                 110

Gln Gly Thr Leu Val Thr Val Ser Ser
        115                 120

<210> SEQ ID NO 122
<211> LENGTH: 121
<212> TYPE: PRT
<213> ORGANISM: Artificial Sequence
<220> FEATURE:
<223> OTHER INFORMATION: Synthetic Heavy chain variable region of
      anti-EGFR scFv (modified)

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Cys Leu Glu Trp Val
        35                  40                  45

Ser Gly Ile Ser His Ser Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Thr Pro Arg Pro Leu Lys Pro Phe Asp Tyr Trp Gly
            100                 105                 110

Gln Gly Thr Leu Val Thr Val Ser Ser
        115                 120

<210> SEQ ID NO 123
<211> LENGTH: 111
<212> TYPE: PRT
<213> ORGANISM: Artificial Sequence
```

<220> FEATURE:
<223> OTHER INFORMATION: Synthetic Light chain variable region of
      anti-EGFR scFv

<400> SEQUENCE: 123

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Gly Gly Thr Lys Leu Thr Val Leu Gly
            100                 105                 110

<210> SEQ ID NO 124
<211> LENGTH: 111
<212> TYPE: PRT
<213> ORGANISM: Artificial Sequence
<220> FEATURE:
<223> OTHER INFORMATION: Synthetic Light chain variable region of
      anti-EGFR scFv (modified)

<400> SEQUENCE: 124

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Cys Gly Thr Lys Leu Thr Val Leu Gly
            100                 105                 110

<210> SEQ ID NO 125
<211> LENGTH: 153
<212> TYPE: PRT
<213> ORGANISM: Artificial Sequence
<220> FEATURE:
<223> OTHER INFORMATION: Synthetic anti-EGFR DARPin-01

<400> SEQUENCE: 125

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Thr Trp Gly Trp Thr Pro Leu His Leu Ala Ala Tyr Gln Gly His Leu
        35                  40                  45

Glu Ile Val Glu Val Leu Leu Lys Asn Gly Ala Asp Val Asn Ala Tyr

```
                    50                  55                  60
Asp Tyr Ile Gly Trp Thr Pro Leu His Leu Ala Ala Asp Gly His Leu
 65                  70                  75                  80

Glu Ile Val Glu Val Leu Leu Lys Asn Gly Ala Asp Val Asn Ala Ser
                 85                  90                  95

Asp Tyr Ile Gly Asp Thr Pro Leu His Leu Ala Ala His Asn Gly His
                100                 105                 110

Leu Glu Ile Val Glu Val Leu Leu Lys His Gly Ala Asp Val Asn Ala
                115                 120                 125

Gln Asp Lys Phe Gly Lys Thr Ala Phe Asp Ile Ser Ile Asp Asn Gly
                130                 135                 140

Asn Glu Asp Leu Ala Glu Ile Leu Gln
145                 150

<210> SEQ ID NO 126
<211> LENGTH: 154
<212> TYPE: PRT
<213> ORGANISM: Artificial Sequence
<220> FEATURE:
<223> OTHER INFORMATION: Synthetic Anti-EGFR DARPin-67

<400> SEQUENCE: 126

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Thr Asp
                 20                  25                  30

Asn Asp Gly Asn Thr Pro Leu His Leu Ser Ala Trp Ile Gly His Leu
                 35                  40                  45

Glu Ile Val Glu Val Leu Leu Lys His Gly Ala Asp Val Asn Ala Asp
 50                  55                  60

Asp Leu Leu Gly Met Thr Pro Leu His Leu Ala Ala Asp Thr Gly His
 65                  70                  75                  80

Leu Glu Ile Val Glu Val Leu Leu Lys Tyr Gly Ala Asp Val Asn Ala
                 85                  90                  95

Arg Asp Thr Arg Gly Lys Thr Pro Leu His Leu Ala Ala Arg Asp Gly
                100                 105                 110

His Leu Glu Ile Val Glu Val Leu Leu Lys His Asp Ala Asp Val Asn
                115                 120                 125

Ala Gln Asp Lys Phe Gly Lys Thr Ala Phe Asp Ile Ser Ile Asp Asn
                130                 135                 140

Gly Asn Glu Asp Leu Ala Glu Ile Leu Gln
145                 150

<210> SEQ ID NO 127
<211> LENGTH: 154
<212> TYPE: PRT
<213> ORGANISM: Artificial Sequence
<220> FEATURE:
<223> OTHER INFORMATION: Synthetic Anti-EGFR DARPin-68

<400> SEQUENCE: 127

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Asp Val Asn Ala Phe Asp
                 20                  25                  30

Tyr Trp Gly Met Thr Pro Leu His Leu Ala Ala Asp Asn Gly His Leu
                 35                  40                  45
```

```
Glu Ile Val Glu Val Leu Leu Lys His Gly Ala Asp Val Asn Ala Ser
 50                  55                  60
Asp Asn Phe Gly Phe Thr Pro Leu His Leu Ala Ala Phe Tyr Gly His
 65                  70                  75                  80
Leu Glu Ile Val Glu Val Leu Leu Lys His Gly Ala Asp Val Asn Ala
                 85                  90                  95
Phe Asp Met Trp Gly Asn Thr Pro Leu His Leu Ala Ala Gln Asn Gly
                100                 105                 110
His Leu Glu Ile Val Glu Val Leu Leu Lys Asn Gly Ala Asp Val Asn
                115                 120                 125
Ala Gln Asp Lys Phe Gly Lys Thr Ala Phe Asp Ile Ser Ile Asp Asn
    130                 135                 140
Gly Asn Glu Asp Leu Ala Glu Ile Leu Gln
145                 150

<210> SEQ ID NO 128
<211> LENGTH: 187
<212> TYPE: PRT
<213> ORGANISM: Artificial Sequence
<220> FEATURE:
<223> OTHER INFORMATION: Synthetic Anti-EGFR DARPin-69

<400> SEQUENCE: 128

Asp Leu Gly Lys Lys Leu Leu Glu Ala Ala Arg Ala Gly Gln Asp Asp
1               5                   10                  15
Glu Val Arg Ile Leu Met Ala Asn Gly Ala Asp Val Asn Ala Asp Asp
                 20                  25                  30
Asn Ala Gly Arg Thr Pro Leu His Leu Ala Ala Asn Phe Gly His Leu
                 35                  40                  45
Glu Ile Val Glu Val Leu Leu Lys Asn Gly Ala Asp Val Asn Ala Lys
 50                  55                  60
Gly His His Cys Asn Thr Pro Leu His Leu Ala Ala Trp Ala Gly His
 65                  70                  75                  80
Leu Glu Ile Val Glu Val Leu Leu Lys Tyr Gly Ala Asp Val Asn Ala
                 85                  90                  95
Asp Asp Asp Glu Gly Tyr Thr Pro Leu His Leu Ala Ala Asp Ile Gly
                100                 105                 110
Asp Leu Glu Ile Val Glu Val Leu Leu Lys Tyr Gly Ala Asp Val Asn
                115                 120                 125
Ala Trp Asp Met Tyr Gly Arg Thr Pro Leu His Leu Ala Ala Ser Ala
    130                 135                 140
Gly His Leu Glu Ile Val Glu Val Leu Leu Lys Tyr Gly Ala Asp Val
145                 150                 155                 160
Asn Ala Gln Asp Lys Phe Gly Lys Thr Ala Phe Asp Ile Ser Ile Asp
                165                 170                 175
Asn Gly Asn Glu Asp Leu Ala Glu Ile Leu Gln
                180                 185
```

COMBINATION THERAPY USING BISPECIFIC ANTI-C-MET/ANTI-EGFR ANTIBODY AND C-SRC INHIBITOR

CROSS-REFERENCE TO RELATED APPLICATIONS

This application claims the benefit of Korean Patent Application No. 10-2014-0006903 filed on Jan. 20, 2014 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 151,302 Byte ASCII (Text) file named "719212.ST25.TXT -Revised-3," created on Apr. 18, 2017.

BACKGROUND OF THE INVENTION

1. Field

Provided is a pharmaceutical composition including a bispecific anti-c-Met/anti-EGFR antibody and a c-Src inhibitor and a method of preventing and/or treating cancer including co-administering a bispecific anti-c-Met/anti-EGFR antibody and a c-Src inhibitor to a subject in need thereof.

2. Description of the Related Art c-Met is a membrane receptor which regulates embryonic development and wound healing, and its abnormal activation causes the tumor growth. EGFR is a membrane receptor involved in several cell functions such as cell growth and migration, and the overexpression or mutation of EGFR results into tumor formation. c-Src is a downstream mediator of several cell signaling pathways including the EGFR and c-Met pathways.

Various drugs capable of targeting the proteins above have been developed. For example, the EGFR monoclonal antibody (mAb) erbitux is used for colorectal tumor treatment; the c-Met small molecule (SM) inhibitor crizotinib is used for treatment of ALK-driven lung cancer; the c-Src SM inhibitor dasatinib is used for treatment of Chronic Phase Philadelphia chromosome positive Chronic Myelogenous Leukemia (CP-CML), each of which has been approved by the FDA.

However, cancer therapies that use such drugs exhibit anticancer effects only on specific types of cancers, and thus have limitations in their indications and/or have no sufficient therapeutic effect on various cancers or mutant cancers.

Thus, more effective treatments for cancer are needed in view of the limitations of current cancer therapies targeting EGFR, c-Met, and c-Src, such as a multiple combination therapy that targets 2 or more of the aforementioned biomolecules.

BRIEF SUMMARY OF THE INVENTION

Provided is a triple-targeting combination therapy which targets c-Met, EGFR, and c-Src.

An embodiment provides a pharmaceutical composition including a bispecific anti-c-Met/anti-EGFR antibody and a c-Src inhibitor. The pharmaceutical composition may be used as a pharmaceutical composition for combined therapy for prevention and/or treatment of a cancer.

Another embodiment provides a kit for prevention and/or treatment of a cancer, including a first pharmaceutical composition (e.g., in a first container) including a bispecific anti-c-Met/anti-EGFR antibody as an active ingredient, a second pharmaceutical composition (e.g., in a second container) comprising a c-Src inhibitor as an active ingredient, and a package or container including, enveloping, binding, or otherwise packaging or associating the two compositions together.

Another embodiment provides a method of prevention and/or treatment of a cancer including co-administering a bispecific anti-c-Met/anti-EGFR antibody and a c-Src inhibitor to a subject in need of prevention and/or treatment of the cancer.

DETAILED DESCRIPTION OF THE INVENTION

Figure 1:
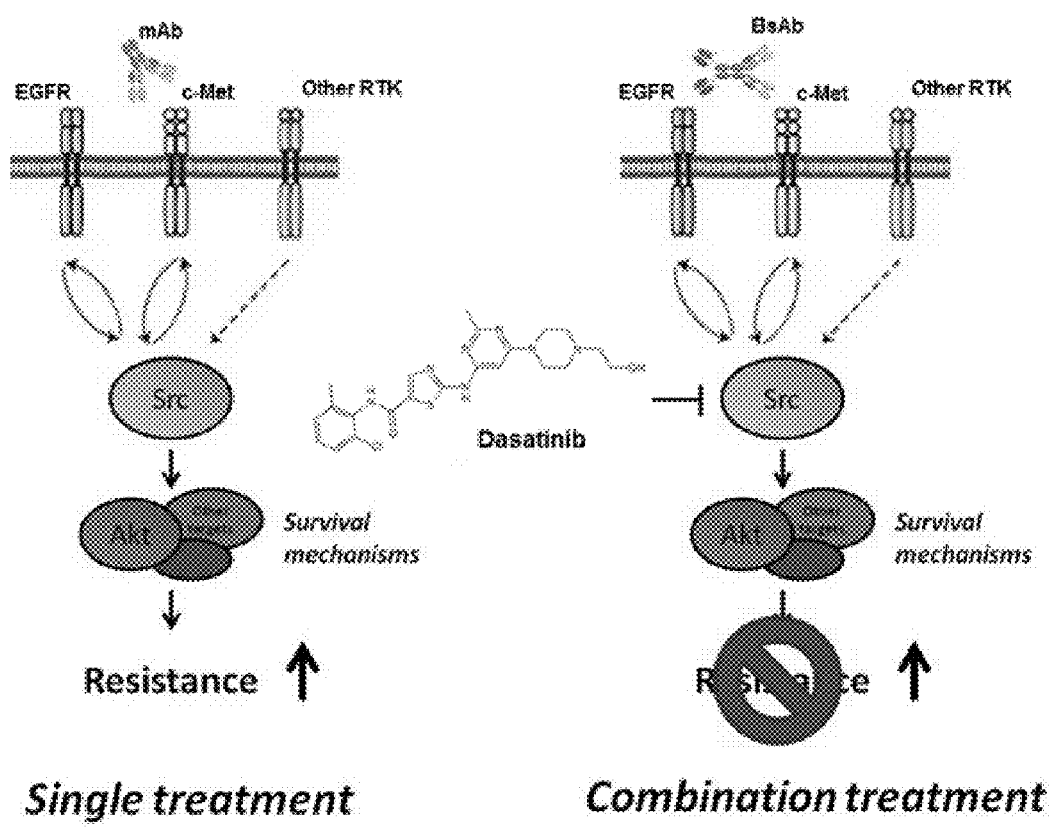
FIG. 1 is a schematic diagram showing the strategy and potential mechanisms when therapies targeting c-Met, EGFR, and c-Src, respectively, are applied individually or together.

A bispecific antibody, as the term is used herein, refers to an antibody-like polypeptide that comprises antigen-binding regions that are specific to two different antigens. The antigen binding regions can be, or instance, fragments of two monoclonal antibodies specific for different antigens, or other antigen-binding motifs and specifically binds to two different antigens. It is confirmed that the use of a bispecific anti-c-Met/anti-EGFR antibody can lead to decrease of drug resistance caused by confusion between c-Met and EGFR pathways. In addition, the use of the bispecific antibody has an advantage that it exhibits lower toxicity to host cells compared to the combination of two single-targeting antibodies. However, existing bispecific anti-c-Met/anti-EGFR antibodies tend not to have effect on several mutated tumor cells such as K-Ras mutated- or T790M mutated tumor cell line. These problems can be overcome by administering a bispecific antibody together with a c-Src inhibitor.

A triple targeting combination therapy, which targets c-Met, EGFR, and c-Src, is provided. The therapy employs a bispecific anti-c-Met/anti-EGFR antibody and a c-Src inhibitor.

In preferred embodiments, the therapeutic regimen suggested herein may be characterized by (1) inhibiting resistance-inducing factors to prevent acquisition of resistance by a targeting drug such as an antibody, thereby maximizing the effect (e.g., anticancer effect) of the targeting drug; (2) expanding the indications for the use of the targeting drug even to the cases on which the targeting drug has no therapeutic effect due to acquisition of resistance thereto or mutation (e.g., K-Ras or T790M mutated cell line, etc.); (3) reducing the dosage of the targeting drug due to its increased effect; and thus, (4) minimizing the toxicities to living body to reduce side effects.

The combination therapy provided herein comprises co-administering a bispecific anti-c-Met/anti-EGFR antibody, and another anti-cancer effective drug. Such combination therapy can achieve not only synergistic effect by co-administration but also increased efficacy of a bispecific anti-c-Met/anti-EGFR antibody, which can allow for the reduction of the dosage of the bispecific anti-c-Met/anti-EGFR antibody, thereby minimizing side effects and maximizing the anticancer effect thereof. In addition, such combination therapy can exhibit anticancer effect even on a cancer against which an anti-c-Met antibody, an anti-EGFR antibody, or bispecific anti-c-Met/anti-EGFR antibody exhibits no effect or only minimal anticancer effect when administered alone, and/or on a cancer induced by, associated with, or characterized by a mutation (e.g., K-Ras or EGFR T790M mutation). The combination therapy can, thus, make it possible to overcome resistance to other anti-cancer agents, particularly a tyrosine kinase inhibitor (TKI) such as an anti-c-Met antibody, an anti-EGFR antibody, or a bispecific anti-c-Met/anti-EGFR antibody. The cancer, against which an anti-c-Met antibody, an anti-EGFR antibody, or bispecific anti-c-Met/anti-EGFR antibody exhibits little or no anticancer effect when administered alone, may be have innate resistance to a tyrosine kinase inhibitor, which can be effectively overcome by the combination therapy provided herein.

One embodiment discloses a combination therapy of a bispecific anti-c-Met/anti-EGFR antibody and a c-Src inhibitor. The combination therapy can simultaneously inhibit HGF/c-Met interaction, which is known as an important growth factor of cancer cells, and the function of a receptor tyrosine kinase, epidermal growth factor receptor (EGFR), thereby blocking the downstream signal transduction pathway thereof. As a result, the combination therapy can exhibit increased anticancer effects, which can allow one skilled in the art to reduce the effective dosage of each drug, and have anticancer effect even on cancers with mutation and/or resistance to a tyrosine kinase inhibitor. That is, by inhibiting three targets, c-Met, EGFR, and c-Src, at once, the effects, such as, increased anticancer effect, reduced effective dosages, decreased side effects, overcoming resistance to tyrosine kinase inhibitor, anticancer effect on cancers induced by mutation (e.g., K-Ras or EGFR T790M mutation), and expansion of application and scope of existing c-Met, EGFR, and c-Src treatments, can be obtained.

Without wishing to be bound by any particular theory or mechanism of action, FIG. 1 is a schematic diagram exemplarily illustrating a possible reaction mechanism that occurs when drugs targeting c-Met, EGFR, or c-Src, are used individually or in combination. The left side of FIG. 1 schematically demonstrates a possible reaction mechanism when the targeting drugs, each of which targets c-Met, EGFR, or c-Src, are administered individually (single treatment), showing that the survival mechanism of cancer cells is not blocked by such single treatment, and resistance to the used drug can be obtained by such failure to block the survival mechanism. The right side of FIG. 1 schematically demonstrates a reaction mechanism when the targeting drugs are co-administered (combination treatment), showing that the survival mechanism of cancer cells is effectively blocked by such combination treatment thereby inhibiting growth of tumor cells.

In addition, the triple targeting may be carried out by using a bispecific anti-c-Met/anti-EGFR antibody simultaneously targeting c-Met and EGFR. Such triple targeting using a bispecific anti-c-Met/anti-EGFR antibody can be solve the problems in safety which can be caused by the simple co-administration of inhibitors targeting c-Met, EGFR, and c-Src, respectively, and achieve an increased therapeutic effect compared thereto.

One embodiment provides a pharmaceutical composition comprising a bispecific anti-c-Met/anti-EGFR antibody and a c-Src inhibitor, as active ingredient, along with a carrier. The pharmaceutical composition is useful for combination therapy in preventing and/or treating cancer, which comprises a bispecific anti-c-Met/anti-EGFR antibody and a c-Src inhibitor, as active ingredient.

In one embodiment, the pharmaceutical composition for combination therapy may be a mixed formulation (e.g., a single composition comprising two or more active ingredients) of a bispecific anti-c-Met/anti-EGFR antibody and a c-Src inhibitor. The bispecific anti-c-Met/anti-EGFR antibody and c-Src inhibitor can be present in any amount that is pharmaceutically effective when used together, which amount may be determined by a skilled medical practitioner or medical researcher. The composition thus formulated can be used for simultaneous administration of the two active ingredients.

Alternatively, the bispecific anti-c-Met/anti-EGFR antibody and the anti-c-Met antibody or antigen-binding fragment thereof can each be formulated in a separate composition, and the separate compositions comprising the two active ingredients can be separately administered simultaneously or sequentially in any order. For instance, a first pharmaceutical composition comprising a pharmaceutically effective amount of a bispecific anti-c-Met/anti-EGFR antibody as an active ingredient and a second pharmaceutical composition comprising a pharmaceutically effective amount of an anti-c-Met antibody or antigen-binding fragment thereof as an active ingredient can be administered simultaneously or sequentially. In the case of the sequential administration, any order of administration may be used.

In another embodiment, a kit for prevention and/or treatment of a cancer is provided, wherein the kit may comprise (a) a first pharmaceutical composition containing a bispecific anti-c-Met/anti-EGFR antibody as an active ingredient, (b) a second pharmaceutical composition containing a c-Src inhibitor as an active ingredient, and (c) a package container. The bispecific anti-c-Met/anti-EGFR antibody and the anti-c-Met antibody or an antigen-binding fragment thereof may be used in amounts that are pharmaceutically effective when combined, which amount may be determined by a skilled medical practitioner or medical researcher. The package container can be any container that holds or otherwise links the two compositions in individual containers together in a single unit (e.g., a box that holds both containers, or plastic wrap that binds both containers together), or the package container may be a single, divided container having at least two chambers that each hold one of the two compositions.

The combination therapy of a bispecific anti-c-Met/anti-EGFR antibody and a c-Src inhibitor can achieve excellent synergistic results and also decreased dosage when compared to single administration of each drug. In addition, the combined therapy can maintain an excellent anticancer effect, even when the administration interval is lengthened and/or the administration dosage is reduced, when compared to single administration of each drug. Furthermore, the combination therapy can exhibit excellent anticancer effects on a cancer on which each inhibitor targeting c-Met, EGFR, or c-Src has no effect (e.g., a cancer having mutation (e.g., K-Ras or EGFR T790M mutation), and/or a cancer having resistance to a tyrosine kinase inhibitor.

c-Src (Proto-oncogene tyrosine-protein kinase Src; proto-oncogene c-Src), which is one of targets of the combination therapy, is a member of non-receptor protein tyrosine kinases, and has an activity that phosphorylates a specific tyrosine residue in a target protein. Activation of c-Src relates to cancer incidence and cancer progress caused by stimulation of cell signaling. The c-Src may be originated any species of animals (e.g., mammals), and for example may be at least one selected from the group consisting of primate c-Src including human c-Src (e.g., Accession No. NP_005408), monkey c-Src (e.g., Accession No. XP_002830325), and the like, and rodent c-Src including mouse c-Src (e.g., Accession No. NP_001020566), rat c-Src (e.g., Accession No. NP_114183), and the like, but not be limited thereto.

"c-Met" or "c-Met protein," which is another target of the combination therapy, refers to a receptor tyrosine kinase (RTK) which binds hepatocyte growth factor (HGF). c-Met may be derived from any species, particularly a mammal, for instance, primates such as human c-Met (e.g., Accession No. NP_000236), monkey c-Met (e.g., *Macaca mulatta*, Accession No. NP_001162100), or rodents such as mouse c-Met (e.g., Accession No. NP_032617.2), rat c-Met (e.g., Accession No. NP_113705.1), and the like. The c-Met protein may include a polypeptide encoded by the nucleotide sequence identified as GenBank Accession Number NM_000245, a polypeptide including the amino acid sequence identified as GenBank Accession Number NP_000236 or extracellular domains thereof. The receptor tyrosine kinase c-Met participates in various mechanisms, such as cancer incidence, metastasis, migration of cancer cell, invasion of cancer cell, angiogenesis, and the like.

The "epidermal growth factor receptor (EGFR)," which is another target of the combination therapy, refers to a member of the receptor tyrosine kinases of HER family. The binding of a ligand to the extracellular domain of EGFR induces receptor homo- or hetero dimerization with other ErbB receptors, which in turn results in intracellular self-phosphorylation of specific tyrosine residues. EGFR self-phosphorylation leads to downstream signal transduction networks including MAPK and PI3K/Akt activation which affects cell proliferation, angiogenesis and metastasis. Overexpression, gene amplification, mutation, or rearrangement of EGFR are frequently observed in several human malignant tumors and are related to poor prognosis of cancer treatment and bad clinical outcomes. For such reasons, the EGFR becomes an important target in anticancer therapy. The EGFR may be derived from mammals, for example, primates such as humans and monkeys, or rodents such as rats and mice. For instance, the EGFR may a polypeptide encoded by one selected from the group consisting of the nucleotide sequences (mRNA) deposited under GenBank Accession Nos. JQ739160, JQ739161, JQ739162, JQ739163, JQ739164, JQ739165, JQ739166, JQ739167, NM_005228.3, NM_201284.1, NM_201282.1, or NM_201283.1.

The c-Src inhibitor, which is an active ingredient of the combination therapy, may be at least one selected from the group consisting of dasatinib, saracatinib, bosutinib, 1-Naphthyl PP1 (CAS 221243-82-9; 1-(1,1-Dimethylethyl)-3-(1-naphthalenyl)-1H-pyrazolo[3,4-d]pyrimidin-4-amine), A 419259 trihydrochloride (CAS 364042-47-7; 7-[trans-4-(4-Methyl-1-piperazinyl)cyclohexyl]-5-(4-phenoxyphenyl)-7H-Pyrrolo[2,3-d]pyrimidin-4-amine trihydrochloride), AG 538 (CAS 133550-18-2; α-Cyano-(3,4-dihydroxy)cinnamoyl-(3',4'-dihydroxyphenyl)ketone), AGL 2263 ((E)-2-(3,4-dihydroxybenzoyl)-3-(2-oxo-3H-1,3-benzoxazol-5-yl)prop-2-enenitrile), Bcr-abl Inhibitor II (CAS 607702-99-8; 4-fluoro-N-{5-[(4-fluorobenzyl)sulfanyl]-1,3,4-thiadiazol-2-yl}benzamide), Bosutinib (CAS 380843-75-4; 4-[(2,4-Dichloro-5-methoxyphenyl)amino]-6-methoxy-7-[3-(4-methyl-1-piperazinyl)propoxy]-3-quinolinecarbonitrile), Altenusin (CAS 31186-12-6), Herbimycin A (CAS 70563-58-5; (15R)-17-demethoxy-15-methoxy-11-O-methyl-geldanamycin), PD 166285 (CAS 212391-63-4; 6-(2,6-Dichlorophenyl)-2-[[4-[2-(diethylamino)ethoxy]phenyl]amino]-8-methylpyrido[2,3-d]pyrimidin-7(8H)-one), PKC-412 (CAS 120685-11-2; [9S-(9α,10β,11β,13α]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methylbenzamide), PDGFR Tyrosine Kinase Inhibitor IV (CAS 627518-40-5; 3-Fluoro-N-(6,7-dimethoxy-2,4-dihydroindeno[1,2-c]pyrazol-3-yl)phenylamine), Calphostin C (CAS 121263-19-2; (1R)-2-[12-[(2R)-2-(Benzoyloxy)propyl]-3,10-dihydro-4,9-dihydroxy-2,6,7,11-tetramethoxy-3,10-dioxo-1-perylenyl]-1-methylethylcarbonic acid 4-hydroxyphenyl ester), PP 1 (CAS 172889-26-8; 1-tert-butyl-3-(4-methylphenyl) pyrazolo[3,4-d]pyrimidin-4-amine), PP 2 (CAS 172889-27-9; 4-Amino-5-(4-chlorophenyl)-7-(t-butyl)pyrazolo[3,4-d]pyrimidine), Src Kinase Inhibitor I (CAS 179248-59-0; 4-(4'-Phenoxyanilino)-6,7-dimethoxyquinazoline), EGF/FGF/PDGF Receptor Tyrosine Kinase Inhibitor (CAS 1135256-66-4; 1-(2-Amino-6-(2,6-dichlorophenyl)pyrido[2,3-d]pyrimidin-7-yl)-3-tert-butyl urea), Staurosporine (CAS 62996-74-1; [9S-(9α,10β,11β,13α]-2,3,10,11,12,13-Hexahydro-10-methoxy-9-methyl-11-(methylamino)-9,13-epoxy-1H,9H-diindolo[1,2,3-gh:3',2',1'-lm]pyrrolo[3,4-j][1,7]benzodiazonin-1-one), Lavendustin A (CAS 125697-92-9; 5-[[[(2,5-Dihydroxyphenyl)methyl][(2-hydroxyphenyl)methyl]amino]-2-hydroxybenzoic acid), Indirubin-3'-(2,3-dihydroxypropyl)oximether, Luteolin (CAS 491-70-3; 2-(3,4-Dihydroxyphenyl)-5,7-dihydroxy-4H-1-benzopyran-4-one), SU6656 (CAS 330161-87-0; (3Z)-N,N-Dimethyl-2-oxo-3-(4,5,6,7-tetrahydro-1H-indol-2-ylmethylidene)-2,3-dihydro-1H-indole-5-sulfonamide), TX-1918 (CAS 503473-32-3; 2-((3,5-dimethyl-4-hydroxyphenyl)-methylene)-4-cyclopentene-1,3-dione), Geldanamycin (CAS 30562-34-6; 2-azabicyclo[16.3.1]docasa-4,6,10, 18,21-pentaene-3,20,22-trione, 9,13-dihydroxy-8,14,19-trimethoxy-4,10,12,16-tetramethyl-9-carbamate), MNS (CAS 1485-00-3; 3,4-Methylenedioxy-nitrostyrene), TX-1123 (CAS 157397-06-3; 2-((3,5-di-tert-Butyl-4-hydroxyphenyl)-methylene)-4-cyclopentene-1,3-dione), GW5074 (CAS 220904-83-6; 3-(3,5-Dibromo-4-hydroxy-benzylidene)-5-iodo-1,3-dihydro-indol-2-one), Erlotinib HCl (CAS 183319-69-9; N-(3-ethynylphenyl)-6,7-bis(2-methoxyethoxy)quinazolin-4-amine hydrochloride), NVP-BHG712 (CAS 940310-85-0; 4-methyl-3-(1-methyl-6-(pyridin-3-yl)-1H-pyrazolo[3,4-d]pyrimidin-4-ylamino)-N-(3-(trifluoromethyl)phenyl)benzamide), GW2580 (CAS 870483-87-7; 5-[[3-methoxy-4-[(4-methoxyphenyl)methoxy]phenyl]methyl]-2,4-Pyrimidinediamine), AEE788 (CAS 497839-62-0; (R)-6-(4-((4-ethylpiperazin-1-yl)methyl)phenyl)-N-(1-phenylethyl)-7H-pyrrolo[2,3-d]pyrimidin-4-amine), TAK-901 (CAS 934541-31-8; 5-(3-(ethylsulfonyl)phenyl)-3,8-dimethyl-N-(1-methylpiperidin-4-yl)-9H-pyrido[2,3-b]indole-7-carboxamide), Midostaurin (CAS 120685-11-2; N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methylbenzamide), and PD173074 (CAS 219580-11-7; 1-tert-butyl-3-(2-(4-(diethylamino)butylamino)-6-(3,5-dimethoxyphenyl)pyrido[2,3-d]pyrimidin-7-yl)urea), or any combination thereof, but not be limited thereto.

In one embodiment, the c-Src inhibitor may be at least one selected from the group consisting of dasatinib, saracatinib, and bosutinib, or any combination thereof.

Dasatinib, which is also called as N-(2-chloro-6-methylphenyl)-2-[[6-[4-(2-hydroxyethyl)-1-piperazinyl]-2-methyl-4-pyrimidinyl]amino]-5-thiazole carboxamide monohydrate, has the following structure:

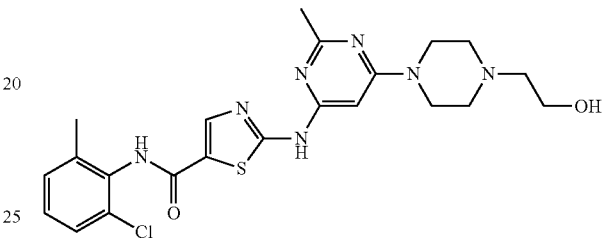

saracatinib, which is also called as AZD0530 (4-Quinazolinamine, N-(5-Chloro-1,3-benzodioxol-4-yl)-7-[2-(4-methyl-1-piperazinyl)ethoxy]-5-[(tetrahydro-2H-pyran-4-yl)oxy]-4-quinazolinamine), has the following structure:

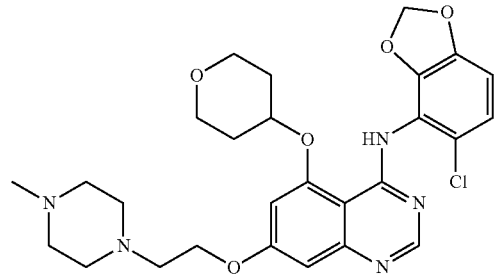 [SMILES: CN1CCN(CCOc2cc(OC3CCOCC3)c3c(Nc4c(Cl)ccc5c4OCO5)ncnc3c2)CC1]

Bosutinib, which is also called as 4-[(2,4-dichloro-5-methoxyphenyl)amino]-6-methoxy-7-[3-(4-methylpiperazin-1-yl)propoxy]quinoline-3-carbonitrile, has the following structure:

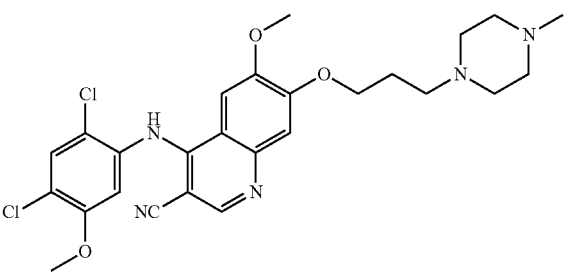 [SMILES: COc1cc(Nc2c(C#N)cnc3cc(OCCCN4CCN(C)CC4)c(OC)cc23)c(Cl)cc1Cl]

The bispecific anti-c-Met/anti-EGFR antibody refers to any antibody which targets c-Met and EGFR at once and inhibits the activities of both of c-Met and EGFR.

The bispecific anti-c-Met/anti-EGFR antibody may comprise (1) an anti-c-Met antibody or antigen-binding fragment thereof, and (2) an anti-EGFR antibody or antigen-binding fragment thereof. The antigen-binding fragment may be selected from the group consisting of scFv, (scFv)2, scFv-Fc, Fab, Fab' and F(ab')2 of an antibody.

In one embodiment, the bispecific anti-c-Met/anti-EGFR antibody may be a bispecific antibody (e.g., dimeric structure) in an N-terminal/C-terminal asymmetric form wherein the upper part (N-terminal part) and the bottom part (C-terminal part) are originated from different antibodies or in different antibody forms from each other. For example N-terminal/C-terminal asymmetric bispecific antibody may comprise (1) an anti-c-Met antibody or antigen-binding fragment thereof, and (2) an EGFR-binding region which is linked to C-terminus or N-terminus, for example C-terminus, of the anti-c-Met antibody or antigen-binding fragment thereof. The EGFR-binding region may be an anti-EGFR antibody or antigen-binding fragment thereof, or an anti-EGFR DARPin (or EGFR-binding DARPin) specifically binding EGFR.

In another embodiment, the bispecific anti-c-Met/anti-EGFR antibody may be a bispecific antibody (dimeric structure) in a left-right asymmetric form wherein two strains (for example, scFv, scFv-Fc, etc.) of the dimeric structure are originated from different antibodies from each other. For example, the left-right asymmetric bispecific antibody may have a dimeric structure comprising a single stranded antigen-binding fragment (e.g., scFv, scFv-Fc, etc.) of an anti-c-Met antibody and a single stranded antigen-binding fragment (e.g., scFv, scFv-Fc, etc.) of the anti-EGFR antibody.

In the N-terminal/C-terminal asymmetric bispecific anti-c-Met/anti-EGFR antibody, the part of an anti-c-Met antibody plays a role of intermediating intracellular internalization and degradation of c-Met protein, and thus, in order to successfully play such role, the part of an anti-c-Met antibody may be in a complete antibody form (e.g., IgG type antibody) of an anti-c-Met antibody. The part of EGFR-binding region is important in specifically recognizing and specifically binding to EGFR, and thus, the part of EGFR-binding region may be in a form of an antigen-binding fragment or an anti-EGFR DARPin, as well as a complete antibody form of an anti-EGFR antibody. Therefore, in an embodiment, the bispecific anti-c-Met/anti-EGFR antibody may comprise an anti-c-Met antibody in a complete antibody form (e.g., IgG type antibody) and an antigen-binding fragment of an anti-EGFR antibody or an anti-EGFR DARPin linked to C-terminus of the anti-c-Met antibody.

In the bispecific anti-c-Met/anti-EGFR antibody, the anti-c-Met antibody or antigen-binding fragment thereof and an anti-EGFR antibody or antigen-binding fragment thereof or anti-EGFR DARPin may be coupled to each other. They may be coupled to each other through a linker, for example, a peptide linker, or through no linker. In addition, in the antigen-binding fragment of the anti-c-Met antibody or the anti-EGFR antibody, a heavy chain region and a light chain region, for example, a heavy chain variable region and a light chain variable region of a scFv fragment, may be linked to each other directly or through a peptide linker. The peptide linker linking the anti-c-Met antibody or antigen-binding fragment thereof and the anti-EGFR antibody or antigen-binding fragment thereof or anti-EGFR DARPin, and the peptide linker linking a heavy chain region and a light chain region in an antigen-binding fragment, may be the same to or different from each other. The peptide linker may be a polypeptide, for example, consisting of about 1 to about 100 or about 2 to about 50 amino acids, and the amino acids may be any amino acids with no specific limitation provided the linker does not interfere with the function of the antigen-binding regions. The peptide linker, for example, may include Gly, Asn, and/or Ser residues, and further include neutral amino acids such as Thr and Ala. Amino acid sequences suitable for the peptide linker are known in the art. Furthermore, the length of the linker may be variably determined within such a limit that does not affect the functions of the fusion protein. For example, the peptide linker may include a total of about 1 to about 100, or about 2 to about 50, or about 5 to about 25 amino acids selected from the group consisting of Gly, Asn, Ser, Thr, and Ala. In one embodiment, the peptide linker may be represented by SEQ ID NO: 131: (GGGGS)n (n, which is a repeating number of (GGGGS, SEQ ID NO: 130), is an integer from about 1 to about 10, e.g., an integer from about 2 to about 5).

In an embodiment, the anti-EGFR antibody or antigen-binding fragment thereof may be cetuximab (Erbitux), panitumumab, an anti-EGFR antibody comprising a heavy chain variable region comprising the amino acid sequence of SEQ ID NO: 109, a light chain variable region comprising the amino acid sequence of SEQ ID NO: 111, or a combination thereof, an anti-EGFR antibody comprising a heavy chain variable region comprising the amino acid sequence of SEQ ID NO: 113, a light chain variable region comprising the amino acid sequence of SEQ ID NO: 114, or a combination thereof, or an antigen-binding fragment of any anti-EGFR antibody listed the above.

For example, the anti-EGFR antibody or antigen-binding fragment nay be cetuximab (Erbitux), panitumumab, an antibody comprising a heavy chain variable region comprising the amino acid sequence of SEQ ID NO: 109 or SEQ ID NO: 113 and a light chain variable region comprising the amino acid sequence of SEQ ID NO: 111 or SEQ ID NO: 114, or antigen-binding fragment thereof (e.g., scFv, scFv-Fc, etc.).

Alternatively, the anti-EGFR antibody or antigen-binding fragment thereof may comprise or consist essentially of:

at least one heavy chain complementarity determining region selected from the group consisting of CDR-H1 comprising the amino acid sequence of SEQ ID NO: 115, CDR-H2 comprising the amino acid sequence of SEQ ID NO: 116, and CDR-H3 comprising the amino acid sequence of SEQ ID NO: 117, or a heavy chain variable region comprising the at least one heavy chain complementarity determining region;

at least one light chain complementarity determining region selected from the group consisting of CDR-L1 comprising the amino acid sequence of SEQ ID NO: 118, CDR-L2 comprising the amino acid sequence of SEQ ID NO: 119, and CDR-L3 comprising the amino acid sequence of SEQ ID NO: 120, or a light chain variable region comprising the at least one light chain complementarity determining region;

a combination of the at least one heavy chain complementarity determining region and the at least one light chain complementarity determining region; or a combination of the heavy chain variable region and the light chain variable region.

The amino acid sequences of SEQ ID NOS: 115 to 120 are summarized in Table 1:

TABLE 1

Amino acid sequence of CDRs of an anti-EGFR antibody

| heavy chain CDR | | light chain CDR | |
|---|---|---|---|
| CDR-H1 | NYDMS (SEQ ID NO: 115) | CDR-L1 | TGSSSNIGNNDVS (SEQ ID NO: 118) |
| CDR-H2 | GISHSSGSKYYADSVKG (SEQ ID NO: 116) | CDR-L2 | DDNKRPS (SEQ ID NO: 119) |
| CDR-H3 | KDATPRPLKPFDY (SEQ ID NO: 117) | CDR-L3 | GSWDASLNA (SEQ ID NO: 120) |

For example, the anti-EGFR antibody or antigen-binding fragment thereof may comprise or consisting essentially of a heavy chain variable region comprising the amino acid sequence of SEQ ID NO: 121 or SEQ ID NO: 122, a light chain variable region comprising the amino acid sequence of SEQ ID NO: 123 or SEQ ID NO: 124, or a combination thereof.

In embodiment, the anti-EGFR antibody or antigen-binding fragment thereof may be an anti-EGFR antibody, an anti-EGFR scFv, or an anti-EGFR scFv-Fc, which comprises a heavy chain variable region comprising the amino acid sequence of SEQ ID NO: 121 or SEQ ID NO: 122 and a light chain variable region comprising the amino acid sequence of SEQ ID NO: 123 or SEQ ID NO: 124.

<SEQ ID NO: 121: Anti-EGFR Antibody Heavy Chain Variable Region>
EVQLLESGGGLVQPGGSLRLSCAASGFTFSNYDM-SWVRQAPGKGLEWVSGISHSSGSKYYADSVKGR-FTISRDNSKNTLYLQMNSLRAEDTAVYYCAKDAT-PRPLKPFDYWGQGTLVTVSS (In SEQ ID NO: 121 above, the underlined bold letters are CDR-H1, CDR-H2, and CDR-H3 in sequence)

<SEQ ID NO: 123: Anti-EGFR Antibody Light Chain Variable Region>
QSVLTQPPSASGTPGQRVTISCTGSSSNIGNND-VSWYQQLPGTAPKLLIYDDNKRPSGVPDRFSGSKS-GTSASLAISGLRSEDEADYYCGSWDASLNAYVF-GGGTKLTVLG (In SEQ ID NO: 123 above, the underlined bold letters are CDR-L1, CDR-L2, and CDR-L3 in sequence)

In an embodiment, the anti-EGFR antibody or antigen-binding fragment thereof may be an anti-EGFR antibody, an anti-EGFR scFv, or an anti-EGFR scFv-Fc, which comprises a heavy chain variable region comprising the amino acid sequence of SEQ ID NO: 109, SEQ ID NO: 113, SEQ ID NO: 121, or SEQ ID NO: 122, and a light chain variable region comprising the amino acid sequence of SEQ ID NO: 111, SEQ ID NO: 114, SEQ ID NO: 123, or SEQ ID NO: 124.

In the anti-EGFR scFv or anti-EGFR scFv-Fc, the heavy chain variable region and the light chain variable region are may be coupled to each other through a linker, for example, a peptide linker, or through no linker (directly). The peptide linker may be a polypeptide, for example, consisting of about 1 to about 100 or about 2 to about 50 amino acids, and the amino acids may be any amino acids with no specific limitation. The peptide linker, for example, may include Gly, Asn, and/or Ser residues, and further include neutral amino acids such as Thr and Ala. Amino acid sequences suitable for the peptide linker are known in the art. Furthermore, the length of the linker may be variably determined within such a limit that does not affect the functions of the fusion protein. For example, the peptide linker may include a total of about 1 to about 100, or about 2 to about 50, or about 5 to about 25 amino acids selected from the group consisting of Gly, Asn, Ser, Thr, and Ala. In one embodiment, the peptide linker may be represented by SEQ ID NO 131: (GGGGS)n (n, which is a repeating number of (GGGGS, SEQ ID NO: 130), is an integer from about 1 to about 10, e.g., an integer from about 2 to about 5).

The anti-EGFR DARPin may be any DARPin that binds EGFR.

The term "designed ankyrin repeat protein (DARPin)" refers to an antibody mimetic protein having high specificity and high binding affinity to a target protein, which is prepared via genetic engineering. DARPins are originated from natural ankyrin protein, and have a structure where at least 2 or at least 3 ankyrin repeat motifs, for example, 3, 4 or 5 ankyrin repeat motifs are repeated. For example, the DARPins comprising 3, 4 or 5 ankyrin repeat motifs may have a molecular weight of about 10 kDa, about 14 kDa, and about 18 kDa, respectively. DARPin includes a core part which carries out structural function and a target binding part outside of the core which binds to a target. The core part includes conserved amino acid sequence and the target binding part includes different amino acid sequence depending on the target.

For example, the anti-EGFR DARPin may be selected from the group consisting of 4 species as follows:

anti-EGFR DARPin-01 (SEQ ID NO: 125):
DLGKKLLEAARAGQDDEVRILMANGADVNADDTWGWTPLHLAAYQGHLEI

VEVLLKNGADVNAYDYIGWTPLHLAADGHLEIVEVLLKNGADVNASDYIG

DTPLHLAAHNGHLEIVEVLLKHGADVNAQDKFGKTAFDISIDNGNEDLAE

ILQ anti-EGFR DARPin-67 (SEQ ID NO: 126):
DLGKKLLEAARAGQDDEVRILMANGADVNATDNDGNTPLHLSAWIGHLEI

VEVLLKHGADVNADDLLGMTPLHLAADTGHLEIVEVLLKYGADVNARDTR

GKTPLHLAARDGHLEIVEVLLKHDADVNAQDKFGKTAFDISIDNGNEDLA

EILQ anti-EGFR DARPin-68 (SEQ ID NO: 127):
DLGKKLLEAARAGQDDEVRILMANGADVNAFDYWGMTPLHLAADNGHLEI

VEVLLKHGADVNASDNFGFTPLHLAAFYGHLEIVEVLLKHGADVNAFDMW

GNTPLHLAAQNGHLEIVEVLLKNGADVNAQDKFGKTAFDISIDNGNEDLA

EILQ anti-EGFR DARPin-69 (SEQ ID NO: 128):
DLGKKLLEAARAGQDDEVRILMANGADVNADDNAGRTPLHLAANFGHLEI

VEVLLKNGADVNAKGHHCNTPLHLAAWAGHLEIVEVLLKYGADVNADDDE

GYTPLHLAADIGDLEIVEVLLKYGADVNAWDMYGRTPLHLAASAGHLEIV

EVLLKYGADVNAQDKFGKTAFDISIDNGNEDLAEILQ

In the bispecific anti-c-Met/anti-EGFR antibody, the anti-EGFR DARPin, which is used as an EGFR binding region, may comprise or consist essentially of about 1 to about 10 units, e.g., about 1 to about 5 units, or about 1 to about 3 units. That is, the anti-EGFR DARPin may comprise or consist essentially of only one unit, or a repeated from wherein about 2 to about 10 unit, about 2 to about 5 unit, about 2 units or about 3 units are repeated. Each unit may be independently selected from the group consisting of the amino sequences of SEQ ID NO: 125 to SEQ ID NO: 127.

The anti c-Met antibody may include any antibody that is capable of recognizing c-Met as an antigen or any antigen-binding fragment thereof. For example, the anti-c-Met antibody may be any antibody specifically binding to c-Met thereby inducing intracellular internalization and degradation of c-Met, or any antigen-binding fragment thereof. The anti-c-Met antibody may recognize a specific region of c-Met, e.g., a specific region in the SEMA domain, as an epitope.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may comprise the amino acid sequence of SEQ ID NO: 79, and is an extracellular domain that functions to bind HGF. A specific region of the SEMA domain, that is, a region comprising the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third beta propellers within the epitopes of the SEMA domain. The region acts as an epitope for the specific anti-c-Met antibody of the present invention.

The term "epitope" as used herein, refers to an antigenic determinant, a part of an antigen recognized by an antibody. In one embodiment, the epitope may be a region including 5 or more contiguous amino acid residues within the SEMA domain (SEQ ID NO: 79) of c-Met protein, for instance, about 5 to about 19 contiguous amino acid residues within the amino acid sequence of SEQ ID NO: 71. For example, the epitope may be a polypeptide including about 5 to about 19 contiguous amino acids selected from among partial combinations of the amino acid sequence of SEQ ID NO: 71, wherein the polypeptide comprises the amino sequence of SEQ ID NO: 73 (EEPSQ), which serves as an essential element for the epitope. For example, the epitope may be a polypeptide comprising, consisting essentially of, or consisting of the amino acid sequence of SEQ ID NO: 71, SEQ ID NO: 72, or SEQ ID NO: 73. As used herein, the phrase "contiguous amino acids" may refer to contiguous amino acid residues on the primary, secondary, or tertiary structure of a protein, wherein the contiguous amino acid residues on the secondary or tertiary structure of a protein may be consecutive or non-consecutive on the primary structure (amino acid sequence) of a protein.

The epitope comprising the amino acid sequence of SEQ ID NO: 72 corresponds to the outermost part of the loop between the second and third beta propellers within the SEMA domain of a c-Met protein. The epitope comprising the amino acid sequence of SEQ ID NO: 73 is a site to which the antibody or antigen-binding fragment according to one embodiment most specifically binds.

Thus, the anti-c-Met antibody may specifically bind to an epitope which includes 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope comprising the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

(i) at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, the amino acid sequence of SEQ ID NO: 2, or an amino acid sequence comprising 8-19 consecutive amino acids within the amino acid sequence of SEQ ID NO: 2 comprising amino acid residues from the $3^{rd}$ to $10^{th}$ positions of the amino acid sequence of SEQ ID NO: 2; and (c) a CDR-H3 comprising the amino acid sequence of SEQ ID NO: 6, the amino acid sequence of SEQ ID NO: 85, or an amino acid sequence comprising 6-13 consecutive amino acids within the amino acid sequence of SEQ ID NO: 85 comprising amino acid residues from the $1^{st}$ to $6^{th}$ positions of the amino acid sequence of SEQ ID NO: 85, or a heavy chain variable region comprising the at least one heavy chain complementarity determining region;

(ii) at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, the amino acid sequence of SEQ ID NO: 15, the amino acid sequence of SEQ ID NO: 86, or an amino acid sequence comprising 9-17 consecutive amino acids within the amino acid sequence of SEQ ID NO: 89 comprising amino acid residues from the $1^{st}$ to $9^{th}$ positions of the amino acid sequence of SEQ ID NO: 89, or a light chain variable region including the at least one light chain complementarity determining region;

(iii) a combination of the at least one heavy chain complementarity determining region and the at least one light chain complementarity determining region; or (iv) a combination of the heavy chain variable region and the light chain variable region.

Herein, the amino acid sequences of SEQ ID NOS: 4 to 9 are respectively represented by Formulas I to VI, below:

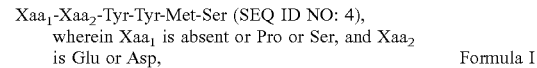

Xaa$_1$-Xaa$_2$-Tyr-Tyr-Met-Ser (SEQ ID NO: 4), wherein Xaa$_1$ is absent or Pro or Ser, and Xaa$_2$ is Glu or Asp,    Formula I

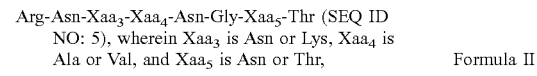

Arg-Asn-Xaa$_3$-Xaa$_4$-Asn-Gly-Xaa$_5$-Thr (SEQ ID NO: 5), wherein Xaa$_3$ is Asn or Lys, Xaa$_4$ is Ala or Val, and Xaa$_5$ is Asn or Thr,    Formula II

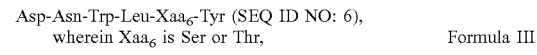

Asp-Asn-Trp-Leu-Xaa$_6$-Tyr (SEQ ID NO: 6), wherein Xaa$_6$ is Ser or Thr,    Formula III

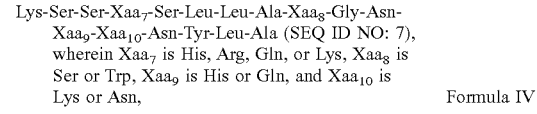

Lys-Ser-Ser-Xaa$_7$-Ser-Leu-Leu-Ala-Xaa$_8$-Gly-Asn-Xaa$_9$-Xaa$_{10}$-Asn-Tyr-Leu-Ala (SEQ ID NO: 7), wherein Xaa$_7$ is His, Arg, Gln, or Lys, Xaa$_8$ is Ser or Trp, Xaa$_9$ is His or Gln, and Xaa$_{10}$ is Lys or Asn,    Formula IV

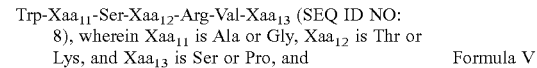

Trp-Xaa$_{11}$-Ser-Xaa$_{12}$-Arg-Val-Xaa$_{13}$ (SEQ ID NO: 8), wherein Xaa$_{11}$ is Ala or Gly, Xaa$_{12}$ is Thr or Lys, and Xaa$_{13}$ is Ser or Pro, and    Formula V Xaa$_{14}$-Gln-Ser-Tyr-Ser-Xaa$_{15}$-Pro-Xaa$_{16}$-Thr (SEQ ID NO: 9), wherein Xaa$_{14}$ is Gly, Ala, or Gln, Xaa$_{15}$ is Arg, His, Ser, Ala, Gly, or Lys, and Xaa$_{16}$ is Leu, Tyr, Phe, or Met.      Formula VI In one embodiment, the CDR-H1 may include an amino acid sequence selected from the group consisting of SEQ ID NO: 1, SEQ ID NO: 22, SEQ ID NO: 23, and SEQ ID NO: 24. The CDR-H2 may include an amino acid sequence selected from the group consisting of SEQ ID NO: 2, SEQ ID NO: 25, and SEQ ID NO: 26. The CDR-H3 may include an amino acid sequence selected from the group consisting of SEQ ID NO: 3, SEQ ID NO: 27, SEQ ID NO: 28, and SEQ ID NO: 85.

The CDR-L1 may comprise an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106. The CDR-L2 may comprise an amino acid sequence selected from the group consisting of SEQ ID NO: 11, SEQ ID NO: 34, SEQ ID NO: 35, and SEQ ID NO: 36. The CDR-L3 may comprise an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In another embodiment, the anti-c-Met antibody or an antigen-binding fragment thereof may comprise or consisting essentially of:

a heavy variable region comprising or consisting essentially of a polypeptide (CDR-H1) comprising an amino acid sequence selected from the group consisting of SEQ ID NO: 1, SEQ ID NO: 22, SEQ ID NO: 23, and SEQ ID NO: 24, a polypeptide (CDR-H2) comprising an amino acid sequence selected from the group consisting of SEQ ID NO: 2, SEQ ID NO: 25, and SEQ ID NO: 26, and a polypeptide (CDR-H3) comprising an amino acid sequence selected from the group consisting of SEQ ID NO: 3, SEQ ID NO: 27, SEQ ID NO: 28, and SEQ ID NO: 85; and a light variable region comprising or consisting essentially of a polypeptide (CDR-L1) comprising an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106, a polypeptide (CDR-L2) comprising an amino acid sequence selected from the group consisting of SEQ ID NO: 11, SEQ ID NO: 34, SEQ ID NO: 35, and SEQ ID NO: 36, and a polypeptide (CDR-L3) comprising an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In an embodiment, the anti-c-Met antibody or an antigen-binding fragment thereof may comprise or consist essentially of a heavy variable region comprising the amino acid sequence of SEQ ID NO: 17, SEQ ID NO: 74, SEQ ID NO: 87, SEQ ID NO: 90, SEQ ID NO: 91, SEQ ID NO: 92, SEQ ID NO: 93, or SEQ ID NO: 94, and a light variable region comprising the amino acid sequence of SEQ ID NO: 18, SEQ ID NO: 19, SEQ ID NO: 20, SEQ ID NO: 21, SEQ ID NO: 75, SEQ ID NO: 88, SEQ ID NO: 95, SEQ ID NO: 96, SEQ ID NO: 97, SEQ ID NO: 98, SEQ ID NO: 99, or SEQ ID NO: 107.

In one embodiment, the anti-c-Met antibody may be a monoclonal antibody. The monoclonal antibody may be produced by the hybridoma cell line deposited with the Korean Cell Line Research Foundation, an international depository authority located at Yungun-Dong, Jongno-Gu, Seoul, Korea, on Oct. 6, 2009, under Accession No. KCLRF-BP-00220, which binds specifically to the extracellular region of c-Met protein (see Korean Patent Publication No. 2011-0047698, the entire disclosure of which is incorporated herein by reference). The anti-c-Met antibody may include all the antibodies defined in Korean Patent Publication No. 2011-0047698.

By way of further example, the anti-c-Met antibody may comprise or consist essentially of:

(a) a heavy chain comprising an amino acid sequence selected from the group consisting of the amino acid sequence of SEQ ID NO: 62 (wherein the amino acid sequence from amino acid residues from the 1$^{st}$ to 17$^{th}$ positions is a signal peptide), the amino acid sequence from the 18$^{th}$ to 462$^{nd}$ positions of SEQ ID NO: 62, the amino acid sequence of SEQ ID NO: 64 (wherein the amino acid sequence from the 1$^{st}$ to 17$^{th}$ positions is a signal peptide), the amino acid sequence from the 18$^{th}$ to 461$^{st}$ positions of SEQ ID NO: 64, the amino acid sequence of SEQ ID NO: 66 (wherein the amino acid sequence from the 1$^{st}$ to 17$^{th}$ positions is a signal peptide), and the amino acid sequence from the 18$^{th}$ to 460$^{th}$ positions of SEQ ID NO: 66; and (b) a light chain comprising an amino acid sequence selected from the group consisting of the amino acid sequence of SEQ ID NO: 68 (wherein the amino acid sequence from the 1$^{st}$ to 20$^{th}$ positions is a signal peptide), the amino acid sequence from the 21$^{st}$ to 240$^{th}$ positions of SEQ ID NO: 68, the amino acid sequence of SEQ ID NO: 70 (wherein the amino acid sequence from the 1$^{st}$ to 20$^{th}$ positions is a signal peptide), the amino acid sequence from the 21$^{st}$ to 240$^{th}$ positions of SEQ ID NO: 70, and the amino acid sequence of SEQ ID NO: 108.

For example, the anti-c-Met antibody may be selected from the group consisting of:

(i) an antibody comprising (a) a heavy chain comprising the amino acid sequence of SEQ ID NO: 62 or the amino acid sequence from the 18$^{th}$ to 462$^{nd}$ positions of SEQ ID NO: 62 and (b) a light chain comprising the amino acid sequence of SEQ ID NO: 68 or the amino acid sequence from the 21$^{st}$ to 240$^{th}$ positions of SEQ ID NO: 68;

(ii) an antibody comprising (a) a heavy chain comprising the amino acid sequence of SEQ ID NO: 64 or the amino acid sequence from the 18$^{th}$ to 461$^{st}$ positions of SEQ ID NO: 64 and (b) a light chain including the amino acid sequence of SEQ ID NO: 68 or the amino acid sequence from the 21$^{st}$ to 240$^{th}$ positions of SEQ ID NO: 68;

(iii) an antibody comprising (a) a heavy chain comprising the amino acid sequence of SEQ ID NO: 66 or the amino acid sequence from the 18$^{th}$ to 460$^{th}$ positions of SEQ ID NO: 66 and (b) a light chain comprising the amino acid sequence of SEQ ID NO: 68 or the amino acid sequence from the 21$^{st}$ to 240$^{th}$ positions of SEQ ID NO: 68;

(iv) an antibody comprising (a) a heavy chain comprising the amino acid sequence of SEQ ID NO: 62 or the amino acid sequence from the 18$^{th}$ to 462$^{nd}$ positions of SEQ ID NO: 62 and (b) a light chain including the amino acid sequence of SEQ ID NO: 70 or the amino acid sequence from the 21$^{st}$ to 240$^{th}$ positions of SEQ ID NO: 70;

(v) an antibody comprising a heavy chain comprising (a) the amino acid sequence of SEQ ID NO: 64 or the amino acid sequence from the 18$^{th}$ to 461$^{st}$ positions of SEQ ID NO: 64 and (b) a light chain comprising the amino acid sequence of SEQ ID NO: 70 or the amino acid sequence from the 21$^{st}$ to 240$^{th}$ positions of SEQ ID NO: 70;

(v) an antibody comprising (a) a heavy chain comprising the amino acid sequence of SEQ ID NO: 66 or the amino acid sequence from the 18$^{th}$ to 460$^{th}$ positions of SEQ ID NO: 66 and (b) a light chain comprising the amino acid sequence of SEQ ID NO: 70 or the amino acid sequence from the 21$^{st}$ to 240$^{th}$ positions of SEQ ID NO: 70;

(vi) an antibody comprising (a) a heavy chain comprising the amino acid sequence of SEQ ID NO: 62 or the amino acid sequence from the 18$^{th}$ to 462$^{nd}$ positions of SEQ ID NO: 62 and (b) a light chain comprising the amino acid sequence of SEQ ID NO: 108;

(vii) an antibody comprising (a) a heavy chain comprising the amino acid sequence of SEQ ID NO: 64 or the amino acid sequence from the 18$^{th}$ to 461$^{st}$ positions of SEQ ID NO: 64 and (b) a light chain comprising the amino acid sequence of SEQ ID NO: 108; and (viii) an antibody comprising (a) a heavy chain comprising the amino acid sequence of SEQ ID NO: 66 or the amino acid sequence from the 18$^{th}$ to 460$^{th}$ positions of SEQ ID NO: 66 and (b) a light chain comprising the amino acid sequence of SEQ ID NO: 108.

In one embodiment, the anti-c-Met antibody may comprise or consist essentially of a heavy chain comprising the amino acid sequence from the 18$^{th}$ to 460$^{th}$ positions of SEQ ID NO: 66 and a light chain comprising the amino acid sequence from the 21$^{st}$ to 240$^{th}$ positions of SEQ ID NO: 68.

The polypeptide comprising the amino acid sequence of SEQ ID NO: 70 is a light chain including human kappa (κ) constant region, and the polypeptide comprising the amino acid sequence of SEQ ID NO: 68 is a polypeptide obtained by replacing histidine at position 62 (corresponding to position 36 of SEQ ID NO: 68 according to kabat numbering) of the polypeptide comprising the amino acid sequence of SEQ ID NO: 70 with tyrosine. The production yield of the antibodies may be increased by the replacement. The polypeptide comprising the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) of SEQ ID NO: 108 with tryptophan. By such replacement, antibodies and antibody fragments including such sequences exhibit increased activities, such as c-Met biding affinity, c-Met degradation activity, Akt phosphorylation inhibition, and the like.

Animal-derived antibodies produced by immunizing non-immune animals with a desired antigen generally invoke immunogenicity when injected into humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic.

An intact antibody includes two full-length light chains and two full-length heavy chains, in which each light chain is linked to a heavy chain by disulfide bonds. The antibody includes a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDRs may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin may be replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one (e.g., two, three, four, five, six, seven, eight, nine, or ten) amino acid residues of the amino acid sequence of the hinge region so that it exhibits enhanced antigen-binding efficiency. For example, the antibody may include a hinge region including the amino acid sequence of SEQ ID NO: 100 (U7-HC6), 101 (U6-HC7), 102 (U3-HC9), 103 (U6-HC8), or 104 (U8-HC5), or a hinge region including the amino acid sequence of SEQ ID NO: 105 (non-modified human hinge). Preferably, the hinge region includes the amino acid sequence of SEQ ID NO: 100 or 101.

In the anti-c-Met antibody or anti-EGFR antibody, the portion of the light chain and the heavy chain portion excluding the CDRs, the light chain variable region, and the heavy chain variable region refers to the light chain constant region and the heavy chain constant region. The heavy chain constant region, the light chain constant region, and/or the region other than the CDR region, the heavy chain variable region, or the light chain variable region, may be originated from any subtype of immunoglobulin (e.g., IgA, IgD, IgE, IgG (IgG1, IgG2, IgG3, IgG4), IgM, etc.).

The term "antigen-binding fragment" used herein refers to fragments of an intact immunoglobulin including portions of a polypeptide including antigen-binding regions having the ability to specifically bind to the antigen. For example, the antigen-binding fragment may be selected from the group consisting of scFv, (scFv)$_2$, Fab, Fab', and F(ab')$_2$, but not be limited thereto.

Among the antigen-binding fragments, Fab that includes light chain and heavy chain variable regions, a light chain constant region, and a first heavy chain constant region $C_{H1}$, includes one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be a polypeptide comprising about 1 to about 100, about 2 to about 50, or about 5 to about 25 amino acids, wherein the amino acids may be selected from any amino acids without limitation.

The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The bispecific anti-c-Met/anti-EGFR antibody can inhibit the activities of c-Met and EGFR due to the intracellular internalization and degradation activity of an anti-c-Met antibody, and may radically prevent the functions of c-Met and EGFR by degrading them and reducing the total amount thereof. Therefore, the bispecific anti-c-Met/anti-EGFR antibody can exhibit effective therapeutic efficacy even when it is applied to a subject having resistance to the existing EGFR targeting drug, for example, an anti-EGFR antibody.

In embodiments comprising a mixture where a pharmaceutically effective amount of bispecific anti-c-Met/anti-EGFR antibody and a pharmaceutically effective amount of a c-Src inhibitor are administered to a subject, the combined pharmaceutical composition comprising a first pharmaceutical composition containing a pharmaceutically effective amount of bispecific anti-c-Met/anti-EGFR antibody as an active ingredient, and the second pharmaceutical composition containing a pharmaceutically effective amount of a c-Src inhibitor as an active ingredient, may be administered along with a pharmaceutically acceptable carrier, diluent, and/or excipient.

The pharmaceutically acceptable carrier to be included in the mixture or the pharmaceutical composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, preservative, and the like.

The pharmaceutical composition, the mixture, or each active ingredient may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

The term "the pharmaceutically effective amount" as used in this specification refers to an amount of which each active ingredient can exert pharmaceutically significant effects.

For one-time administration, a pharmaceutically effective amount of a bispecific anti-c-Met/anti-EGFR antibody and a pharmaceutically effective amount of the c-Src inhibitor may be prescribed in a variety of ways, depending on many factors including formulation methods, administration manners, ages of subjects, body weight, gender, pathologic conditions, diets, administration time, administration interval, administration route, excretion speed, and reaction sensitivity. For example, the effective amount of the c-Src inhibitor for one-time administration may be, but not limited to, ranges of about 0.001 to about 100 mg/kg, or about 0.02 to about 10 mg/kg for one-time administration and the effective amount of the bispecific anti-c-Met/anti-EGFR antibody for one-time administration may be, but not limited to, ranges of about 0.001 to about 100 mg/kg, or about 0.02 to about 10 mg/kg for their one-time administration.

The effective amount for one-time administration may be formulated into a single formulation in a unit dosage form or formulated in suitably divided dosage forms, or it may be manufactured to be contained in a multiple dosage container. For the kit, the effective amount of a bispecific anti-c-Met/anti-EGFR antibody and the effective amount of the c-Src inhibitor for one-time administration (single dose) may be contained in a package container as a base unit.

The administration interval between the administrations is defined as a period between the first administration and the following administration. The administration interval may be, but is not limited to, 24 hours to 30 days (e.g., 10 hours, 15 hours, 20 hours, 1 day, 2 days, 3 days, 4 days, 5 days, 6, days, 7 days, 10 days, 14 days, 21 days, or 28 days) and particularly 7 to 14 days or so. For the combined therapy, the first pharmaceutical composition containing a pharmaceutically effective amount of bispecific anti-c-Met/anti-EGFR antibody as an active ingredient, and the second pharmaceutical composition containing a pharmaceutically effective amount of a c-Src inhibitor as an active ingredient may be co-administered, and the co-administration may be conducted in a given time interval (e.g., several minutes, several hours or several days, or several weeks) to be determined by a type of diseases, a subject's conditions, etc. For example, the first pharmaceutical composition and the second pharmaceutical composition may be simultaneously administered (administration interval within 1 minute) or sequentially administered (administration interval of 1 minute or over), and in case of sequential administration, the administration interval between the first pharmaceutical composition and the second pharmaceutical composition may be 1 to 60 minutes, particularly, 1 minute to 10 minutes, and their administration order may be reversed.

The combined mixture or the pharmaceutical compositions may be a solution in oil or an aqueous medium, a suspension, a syrup, an emulsifying solution form, or they may be formulated into a form of an extract, elixirs, powders, granules, a tablet or a capsule, and they may further include a dispersing agent or a stabilizing agent for their formulation.

In particular, the pharmaceutical composition containing the anti-c-Met antibody or antigen binding fragments thereof may be formulated into an immunoliposome since it contains an antibody or an antigen binding fragment. A liposome containing an antibody may be prepared using any methods well known in the pertinent field. The immunoliposome may be a lipid composition including phosphatidylcholine, cholesterol, and polyethyleneglycol-derived phosphatidylethanolamine, and may be prepared by a reverse phase evaporation method. For example, Fab' fragments of an antibody may be conjugated to the liposome through a disulfide-exchange reaction. A chemical drug, such as doxorubicin, may further be included in the liposome.

Another embodiment provides a method of combination therapy (co-administration). In particular, provided is a method of prevention and/or treatment of a cancer comprising (or consisting essentially of) co-administering a bispecific anti-c-Met/anti-EGFR antibody and a c-Src inhibitor, to a subject in need of prevention and/or treatment of the cancer. The bispecific anti-c-Met/anti-EGFR antibody and the c-Src inhibitor may be administered in amounts that are pharmaceutically effective when combined, which amounts may be determined by a skilled medical practitioner or medical researcher. The method may further include a step of identifying a subject who is in need of the prevention and/or treatment of a cancer, prior to the co-administration step. The step of identifying may be conducted in any manner and/or by methods known in the relevant field for identifying whether or not a subject needs the prevention and/or treatment of cancer. For example, the step of identifying may include diagnosing a subject as a cancer subject having a cancer, or identifying a subject who is diagnosed as a cancer subject.

In one embodiment, the co-administration may be conducted by administering a mixed formulation of a bispecific anti-c-Met/anti-EGFR antibody and a Src inhibitor, as described herein. In another embodiment, the co-administration may be conducted by a first step of administering a bispecific anti-c-Met/anti-EGFR antibody, and a second step of administering a c-Src inhibitor, wherein the first and the second administration steps may be conducted simultaneously or sequentially. In circumstances of the sequential administration, the first step and the second step may be performed in any order. The bispecific anti-c-Met/anti-EGFR antibody and Src inhibitor may be administered in amounts that are pharmaceutically effective when combined, which amount may be determined by the skilled medical practitioner or medical researcher.

The subject may be an animal selected from mammals including primates such as humans and monkeys and rodents such as mice and rats, a cell or a tissue separated from the animal, or a culture of the cell or the tissue.

Another embodiment provides a use of a bispecific anti-c-Met/anti-EGFR antibody and a c-Src inhibitor for combined therapy for treatment and/or prevention of a cancer.

The pharmaceutical composition or method of combination therapy can be applied to treatment and/or prevention of cancer. The cancer may be associated with overexpression and/or abnormal activation of c-Met and/or FGFR. The cancer may be a solid cancer or a blood cancer. In addition, the cancer may have resistance to a tyrosine kinase inhibitor, for example, an anti-c-Met antibody, an anti-EGFR antibody, or a bispecific anti-c-Met/anti-EGFR antibody, and/or be induced by mutation (e.g., K-Ras or EGFR T790M mutation). For example, the cancer may be at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head and neck cancers, brain cancer, osteosarcoma, and the like, but not be limited thereto. The cancer may include a metastatic cancer as well as a primary cancer. For example, the cancer may be a tyrosine kinase inhibitor resistant cancer, a colorectal cancer induced by K-Ras mutation, or a non-small cell lung cancer induced by EGFR T790M mutation.

The prevention and/or treatment effects of the cancers may include effects of not only suppressing the growth of the cancer cells but also suppressing migration, invasion, and/or metastasis of cancers. Therefore, the cancers suitable for treatment with the combined therapy include both primary cancers and metastatic cancers.

EXAMPLES

Hereafter, the present invention will be described in detail by examples.

The following examples are intended merely to illustrate the invention and are not construed to restrict the invention.

Reference Example 1

Construction of Anti-c-Met Antibody 1.1. Production of "AbF46", a Mouse Antibody to c-Met
1.1.1. Immunization of Mice
To obtain immunized mice necessary for the development of a hybridoma cell line, each of five BALB/c mice (Japan SLC, Inc.), 4 to 6 weeks old, was intraperitoneally injected with a mixture of 100 µg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1 \sim 2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, under Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Reference Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen), and a vector from the pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 μl (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) search revealed that VH3-71 has an identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have an identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 2, below.

TABLE 2

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wild type. Most libraries were lower in affinity for c-Met, compared to the wild-type. The affinity for c-Met was retained in some mutants.

1.6. Selection of Antibody with Improved Affinity from Libraries

After affinity maturation of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library constructed | CDR Sequence |
| --- | --- | --- |
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 µl of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as L3-1Y.

Example 1

Preparation of Anti-EGFR scFv

An anti-EGFR scFv specifically binding to EGFR was prepared by inserting $(GGGGS)_3$ peptide linker (SEQ ID NO: 132) between a heavy chain variable region and a light chain variable region.

In particular, using an automatic gene synthesis (Bioneer Inc.), a $(GGGGS)_3$ linker peptide (SEQ ID NO: 132) coding DNA fragment was inserted between a DNA fragment (SEQ ID NO: 110) encoding a humanized anti-EGFR antibody heavy chain variable region (SEQ ID NO: 109) and a DNA fragment (SEQ ID NO: 112) encoding a humanized anti- EGFR antibody light chain variable region (SEQ ID NO: 111), to prepare a scFv (hereinafter, "ME01 scFv") of an anti-EGFR antibody.

A modified anti-EGFR scFv (heavy chain variable region: SEQ ID NO: 113; and light chain variable region: SEQ ID NO: 114; hereinafter, "ME03S scFv") was prepared as described above, with the exception that in the heavy chain variable region (SEQ ID NO: 109), the amino acid, F, at $51^{st}$ position was substituted with I, the amino acid G at $44^{th}$ position with C, and the amino acid Q at $62^{nd}$ position with S, and in the light chain variable region (SEQ ID NO: 111), the amino acid R at $46^{th}$ position was substituted with L, the amino acid F at $83^{rd}$ position with E, and the G at $100^{th}$ position with C. The amino acid location (position) within the antibody complies with kabat numbering system.

In addition, using an automatic gene synthesis (Bioneer Inc.), a DNA fragment encoding a scFv (hereinafter, "ME22S scFv") of an anti-EGFR antibody was prepared by inserting $(GGGGS)_3$ linker peptide (SEQ ID NO: 132) coding DNA fragment between a DNA fragment encoding the anti-EGFR antibody heavy chain variable region (SEQ ID NO: 122) wherein the amino acid G at $44^{th}$ position of the heavy chain variable region (SEQ ID NO: 121) is substituted with C and a DNA fragment encoding the anti-EGFR antibody light chain variable region (SEQ ID NO: 124) wherein the amino acid of G at $100^{th}$ position of the heavy chain variable region (SEQ ID NO: 123) is substituted with C. The amino acid location (position) within the antibody complies with kabat numbering system.

Example 2

Preparation of a Bispecific Anti-c-Met/Anti-EGFR Antibody

The anti-EGFR scFv (ME-01 scFv, ME-03S scFv, ME22S scFv) prepared in Example 1 was fused at the C-terminus of the Fc of the anti-c-Met antibody L3-1Y prepared in Reference Example 1 to prepare a bispecific anti-c-Met/anti-EGFR antibody. The fusion procedures are as follows.

In detail, a DNA fragment having the nucleotide sequence of SEQ ID NO: 66 corresponding to the heavy chain of the anti-c-Met antibody L3-1Y prepared in Reference Example 1 was inserted into a vector of the pcDNA™3.3-TOPO TA Cloning Kit (Cat no. 8300-01) which is included in OptiCHO™ Antibody Express Kit (Cat no. 12762-019) by Invitrogen Inc., and a DNA fragment having the nucleotide sequence of SEQ ID NO: 68 corresponding to the light chain of the anti-c-Met antibody L3-1Y was inserted into a vector of the pOptiVEC™-TOPO TA Cloning Kit. Thereafter, the anti-EGFR scFv coding DNA fragment prepared in Example 1 was fused at the C-terminus of the Fc of L3-1Y which was inserted into pcDNA™3.3, using the coding DNA sequence of a linker peptide having 10 amino acid lengths consisting of $(G_4S)_2$, to construct vectors for the expression of bispecific antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/mL, and after 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with IgG elution buffer (Thermo Scientific, 21004). The buffer was replaced by a PBS buffer to finally obtain purified bispecific anti c-Met/anti-EGFR antibodies.

The prepared bispecific anti-c-Met/anti-EGFR antibodies were named as ME01, ME03S, and ME22S, respectively.

In addition, each of 4 anti-EGFR DARPins (e.g., SEQ ID NO: 205) was fused to C-terminus of anti-c-Met antibody L3-1Y prepared in Reference Example 1, to prepared 4 anti-c-Met antibody/anti-EGFR DARPin conjugates (bispecific anti-c-Met/anti-EGFR antibody). The heavy chain of L3-1Y antibody and the anti-EGFR DARPpin were linked to each other through 'GGGGSGGGGS' (G4S)2 linker (SEQ ID NO 133), to be in the form of 'L3-1Y heavy chain-(G4S) 2-anti-EGFR DARPins'.

```
anti-EGFR DARPin-01 (SEQ ID NO: 205):
DLGKKLLEAARAGQDDEVRILMANGADVNADDTWGWTPLHLAAYQGHLEI

VEVLLKNGADVNAYDYIGWTPLHLAADGHLEIVEVLLKNGADVNASDYIG

DTPLHLAAHNGHLEIVEVLLKHGADVNAQDKFGKTAFDISIDNGNEDLAE

ILQ
```

The prepared bispecific anti-c-Met/anti-EGFR antibody was named as ME-19. The antibody has affinity to EGFR (R&D Systems) of about 0.35 nM when measured by Biacore T100(GE).

Example 3

Cell Proliferation Inhibition Effect on K-Ras Mutant Colorectal Cancer Cell Lines) (Lovo Cell Line)

The effect of co-administration of a bispecific anti-c-Met/anti-EGFR antibody, ME-19 or ME22S, which is prepared in Example 2, and a c-Src inhibitor, dasatinib or saracatinib, was examined in a K-Ras mutated colorectal cancer cell line (Lovo cell line).

The Lovo cell line was obtained from ATCC (ATCC CCL-229). The Lovo cell line comprises K-Ras mutation (K-Ras overexpression) (see http://www.atcc.org/products/all/CCL-229.aspx#85786B46AA23451B94BC5D45200673F7). The cells were stored in RPMI1640 medium (GIBCO) containing 10% (v/v) FBS under the conditions of 5% $CO_2$ and 37° C., until being used in the following experiments. A cell proliferation assay was performed as follows.

RPMI1640 medium (GIBCO) containing 10% FBS was added to 96-well plate. Lovo cells (ATCC, CCL-229) were seeded on the plate at the amount of 5,000 cells/well, and incubated overnight at 37° C. The next day (after 24 hours), the incubated cells were treated with 5 µg/ml of L3-1Y antibody (c-Met mAb; Reference Example 1), 5 µg/ml of erbitux (EGFR mAb; Merck Serono, Germany), 5 µg/ml of L3-1Y antibody+5 µg/ml of erbitux, 5 µg/ml of ME19 or 5 µg/ml of ME22S (c-Met/EGFR bsAb; Example 2), 30 nM dasatinib (c-Src inhibitor; S1021, Selleckchem, US), 30 nM dasatinib+5 µg/ml of L3-1Y antibody, 30 nM dasatinib+5 µg/ml of erbitux, 30 nM dasatinib+5 µg/ml of L3-1Y antibody+5 µg/ml of erbitux, and 30 nM dasatinib+5 µg/m of ME19 or 5 µg/m of ME22S 1, respectively. At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well.

At 72 hours after the treatment, 10 µL of Cell Counting Kit-8 solution (Dojindo Molecular Technologies, Gaithersburg, Md.) was added to each well, and left at room temperature for 2 hours. The number of the cells was counted by measuring the luminescence intensity, and the luminescence intensity was recorded using Envision 2104 Multi-label Reader (Perkin Elmer). The significance of the obtained data were verified through T-test (SigmaPlot 12.3; Systat Software Inc., Chicago, Ill.; *: P-value<0.001; : P-value<0.01; *: P-value<0.05).

Figure 2:
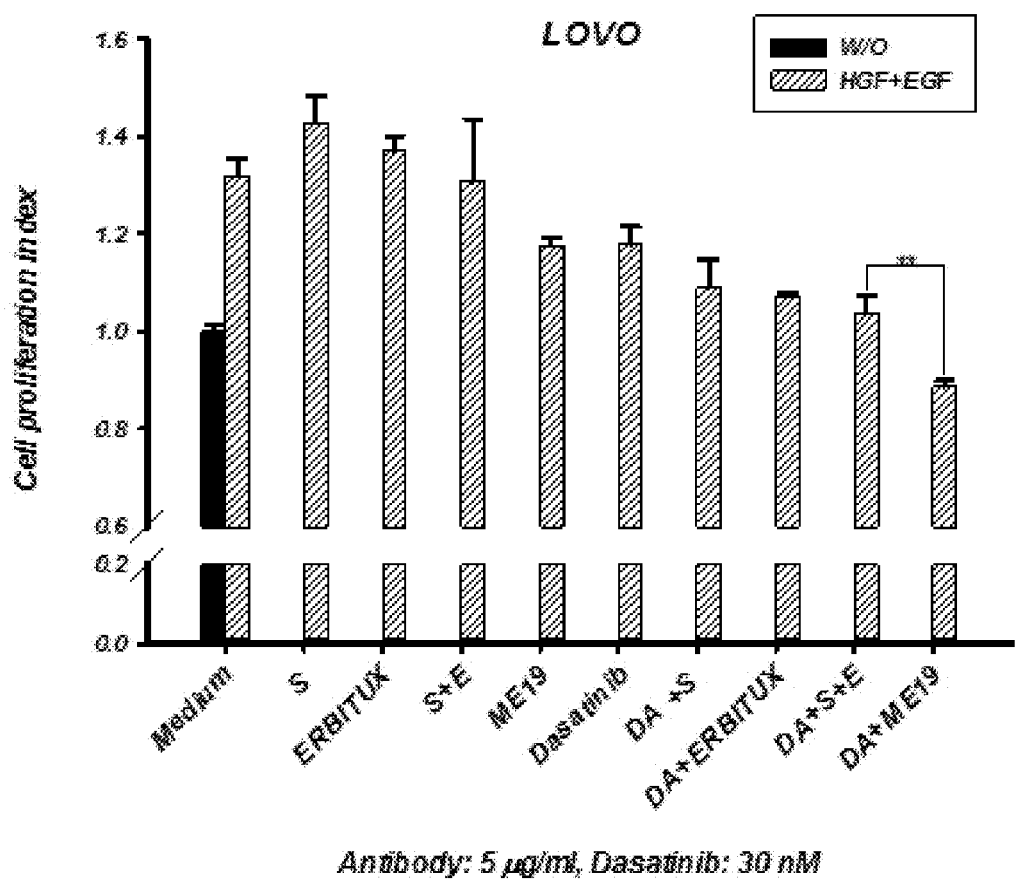
FIG. 2 is a graph showing cell proliferation degree of K-Ras mutated colorectal cancer cell line (Lovo cell line) when treated with a c-Src inhibitor and bispecific anti-c-Met/anti-EGFR antibody ME19 or other agents.
Figure 3:
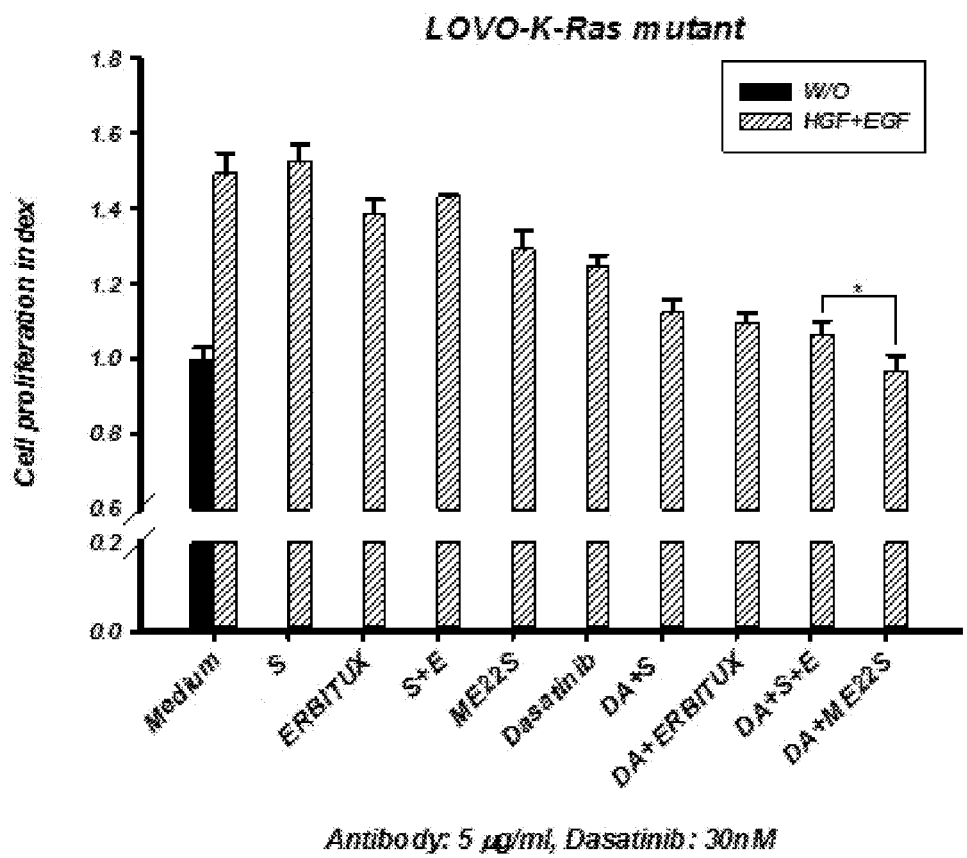
FIG. 3 is a graph showing cell proliferation degree of K-Ras mutated colorectal cancer cell line (Lovo cell line) when treated with a c-Src inhibitor and bispecific anti-c-Met/anti-EGFR antibody ME22 or other agents.

The obtained results are demonstrated in FIG. 2 (ME19) and FIG. 3 (ME22S). FIG. 2 and FIG. 3 reveal that in the K-Ras mutated Lovo cells treated with the combination of bispecific anti-c-Met/anti-EGFR antibody ME19 or ME22S and c-Src inhibitor dasatinib ("dasatinib" or "DA" in FIG. 3), considerable inhibitory effect on the cell proliferation can be achieved, compared to those treated with the drugs alone. On the contrary, it is confirmed that the treatment with L3-1Y antibody ("S" in FIG. 3) and erbitux ("ERBITUX" or "E" in FIG. 3) alone or in combination leads to increased cell proliferation. These results indicate that by co-treatment of a bispecific anti-c-Met/anti-EGFR antibody and a c-Src inhibitor, a considerable anticancer effect on K-Ras mutated cancer cells can be obtained. In addition, even when compared to the case of co-treatment of a c-Src inhibitor (DA), an anti-c-Met antibody(S) and anti-EGFR antibody (E) (instead of a bispecific anti-c-Met/anti-EGFR antibody), the co-treatment of a bispecific anti-c-Met/anti-EGFR antibody (ME-19 or ME22S) and c-Src inhibitor dasatinib (DA) can achieve a considerable inhibition effect on cancer cell proliferation, indicating that the combination therapy using a bispecific anti-c-Met/anti-EGFR antibody and a c-Src inhibitor can lead to excellent anticancer effect compared to the case of co-treatment of three drugs which target the three targets respectively.

In addition, the cell proliferation inhibition effect was examined according to the amounts of a bispecific anti-c-Met/anti-EGFR antibody or dasatinib or saracatinib treated.

To examine the cell proliferation inhibition effect depending on the amount of a bispecific anti-c-Met/anti-EGFR antibody, the experiment was carried out by varying the amount of the treated bispecific anti-c-Met/anti-EGFR antibody with fixing the amount of dasatini as 30 nM. In detail, RPMI1640 medium (GIBCO) containing 10% FBS was added to 96-well plate. Lovo cells (ATCC, CCL-229) were seeded on the plate at the amount of 5,000 cells/well, and incubated overnight at 37° C. The next day (after 24 hours), the incubated cells were treated with various concentrations of ME19 or ME22S (ME-19: 10, 1, 0.1, or 0.01 µg/ml, ME22S: 1, 0.1, or 0.01 µg/ml) alone or together with 30 nM dasatinib (c-Src inhibitor; S1021, Selleckchem, US). At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well.

At 72 hours after the treatment, 10 µL of Cell Counting Kit-8 solution (Dojindo Molecular Technologies, Gaithersburg, Md.) was added to each well, and left at room temperature for 2 hours. The number of the cells was counted by measuring the luminescence intensity, and the luminescence intensity was recorded using Envision 2104 Multi-label Reader (Perkin Elmer). The significance of the obtained data were verified through T-test (SigmaPlot 12.3; Systat Software Inc., Chicago, Ill.; *: P-value<0.001; : P-value<0.01; *: P-value<0.05).

Figure 4:
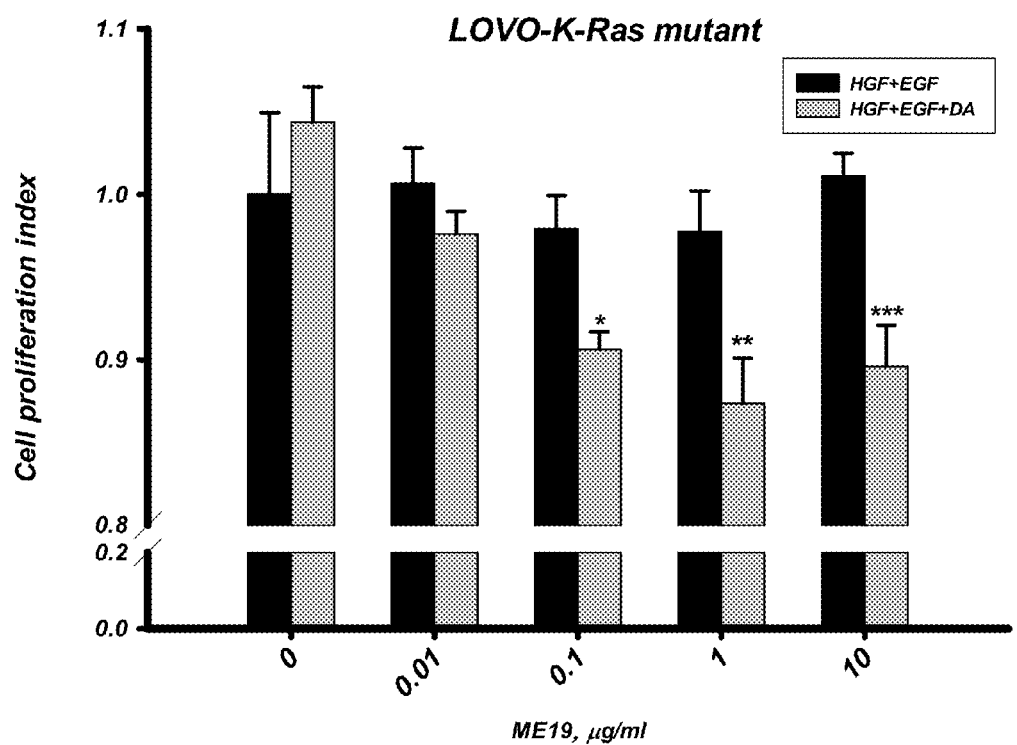
FIG. 4 is a graph showing cell proliferation degree of Lovo cell line when treated with a c-Src inhibitor and bispecific anti-c-Met/anti-EGFR antibody ME19 at various concentrations of antibody.
Figure 5:
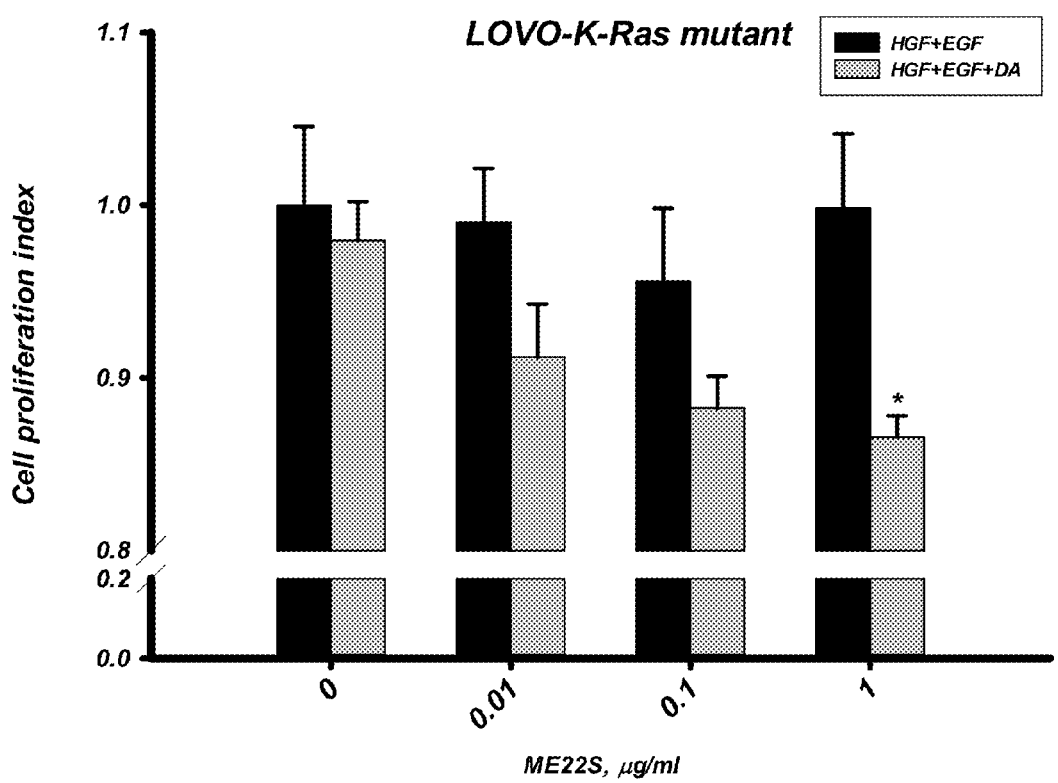
FIG. 5 is a graph showing cell proliferation degree of Lovo cell line when treated with a c-Src inhibitor and bispecific anti-c-Met/anti-EGFR antibody ME22, at various concentrations of antibody.

The obtained results are demonstrated in FIG. 4 (ME19) and FIG. 5 (ME22S). As shown in FIG. 4 and FIG. 5, compared to the treatment of a bispecific anti-c-Met/anti-EGFR antibody alone, the co-treatment of a bispecific anti-c-Met/anti-EGFR antibody and a c-Src inhibitor exhibits more synergistic therapeutic effect, and the synergistic therapeutic effect by the co-treatment (e.g., a difference between the co-treatment and the single treatment) is dose-dependent for the antibody.

In addition, to examine the cell proliferation inhibition effect depending on the amount of dasatinib or saracatinib, the experiment was carried out by varying the amount of the treated c-Src inhibitor, dasatinib or saracatinib [0 (control), 10, 100, or 1000 nM] with fixing the concentration of bispecific anti-c-Met/anti-EGFR antibody ME22S as 5 µg/ml. This experiment was conducted referring to the experiment of the cell proliferation test depending on the amount of the antibody as described above, except the amount of the treated antibody and the c-Src inhibitor. In detail, RPMI1640 medium (GIBCO) containing 10% FBS was added to 96-well plate. Lovo cells (ATCC, CCL-229) were seeded on the plate at the amount of 5,000 cells/well, and incubated overnight at 37° C. On the next day (after 24 hours), the incubated cells were treated with various concentrations [0 (control), 10, 100, or 1000 nM] of a c-Src inhibitor, dasatinib (S1021, Selleckchem, US) or saracatinib (S1006, Selleckchem, US) alone or together with 5 µg/ml of bispecific anti-c-Met/anti-EGFR antibody ME22S. At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well.

At 72 hours after the treatment, 10 µL of Cell Counting Kit-8 solution (Dojindo Molecular Technologies, Gaithersburg, Md.) was added to each well, and left at room temperature for 2 hours. The number of the cells was counted by measuring the luminescence intensity, and the luminescence intensity was recorded using Envision 2104 Multi-label Reader (Perkin Elmer). The significance of the obtained data were verified through T-test (SigmaPlot 12.3; Systat Software Inc., Chicago, Ill.; *: P-value<0.001; : P-value<0.01; *: P-value<0.05).

Figure 6:
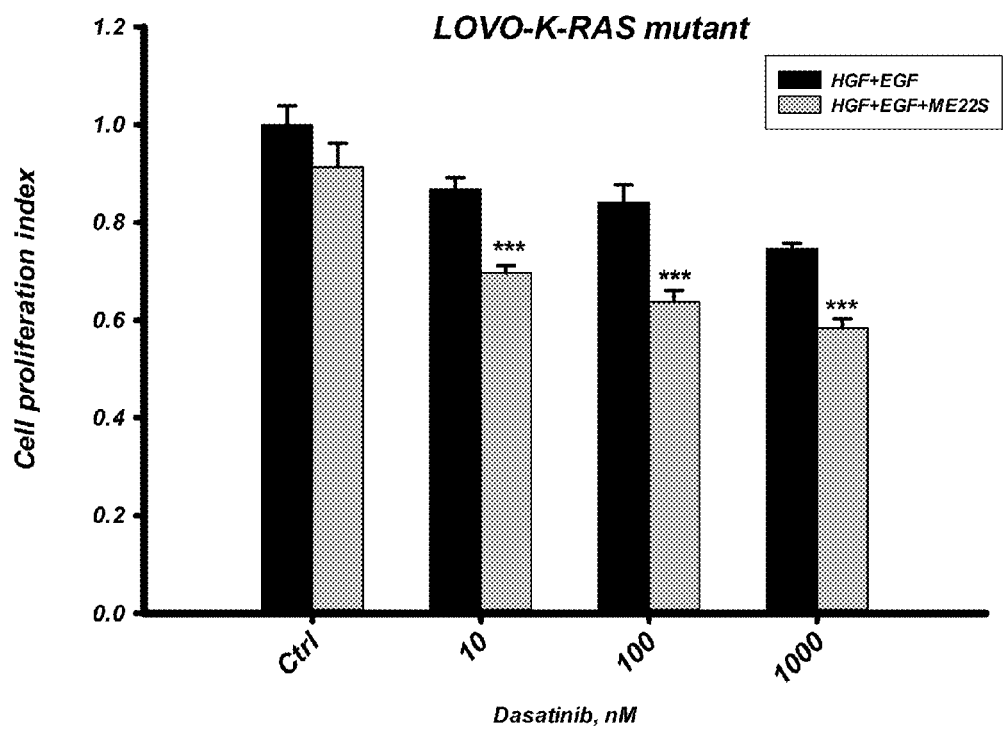
FIG. 6 is a graph showing cell proliferation degree of Lovo cell line when treated with a bispecific anti-c-Met/anti-EGFR antibody and c-Src inhibitor dasatinib, at various concentrations of c-Src inhibitor.
Figure 7:
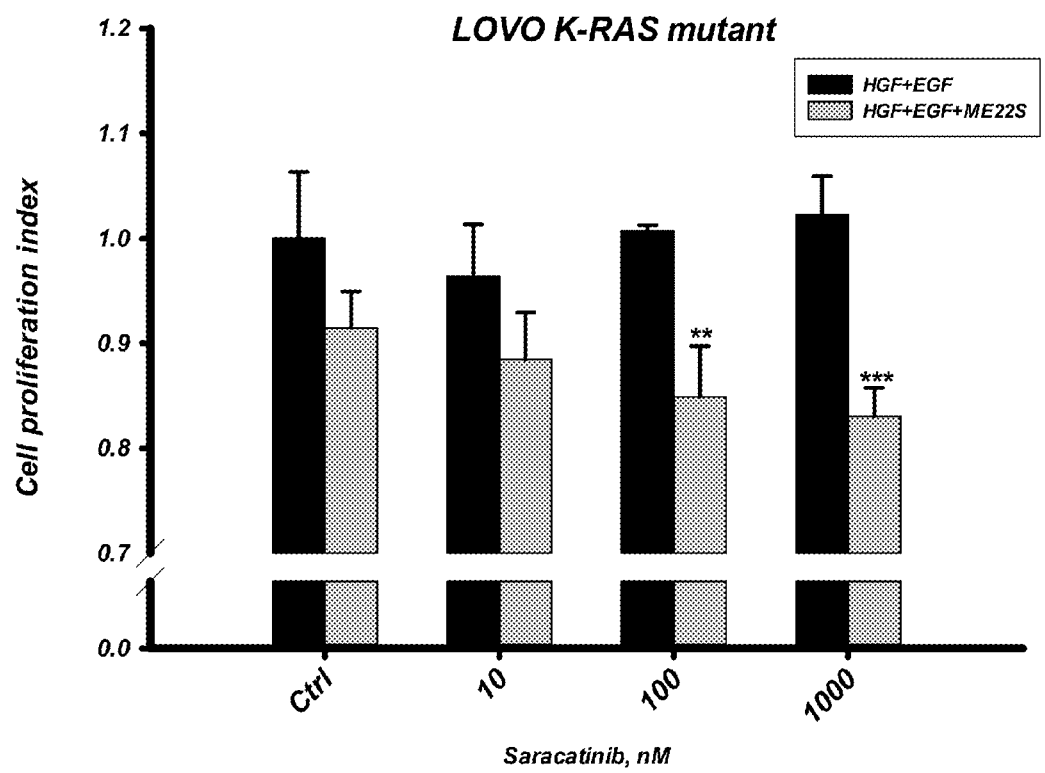
FIG. 7 is a graph showing cell proliferation degree of Lovo cell line when treated with a bispecific anti-c-Met/anti-EGFR antibody and c-Src inhibitor saracatinib, at various concentrations of c-Src inhibitor.

The obtained results are demonstrated in FIG. 6 (dasatinib) and FIG. 7 (saracatinib). As shown in FIG. 6 and FIG. 7, compared to the treatment of a c-Src inhibitor alone, the co-treatment of a c-Src inhibitor and a bispecific anti-c-Met/anti-EGFR antibody exhibits more synergistic therapeutic effect, and the synergistic therapeutic effect by the co-treatment (e.g., a difference between the co-treatment and the single treatment) is generally dose-dependent for the c-Src inhibitor.

Example 4

Cell Proliferation Inhibition Effect on EGFR T790M Mutant Non-Small Cell Lung Cancer Cell Lines (H820 Cell Line)

The effect by co-treatment of bispecific anti-c-Met/anti-EGFR antibody ME-19 prepared in Example 2 and a c-Src inhibitor dasatinib was examined in EGFR T790M mutated non-small cell lung cancer cell line (H820 cell line).

The H820 cell line was obtained from ATCC. The H820 cells comprise EGFR T790M mutation. The cells were stored in RPMI1640 medium (GIBCO) containing 10%(v/v) FBS under the conditions of 5% $CO_2$ and 37° C., until being used in the following experiments. A cell proliferation assay was performed as follows.

RPMI1640 medium (GIBCO) containing 10% FBS was added to 96-well plate. H820 cells (ATCC) were seeded on the plate at the amount of 5,000 cells/well, and incubated overnight at 37° C. On the next day (after 24 hours), the incubated cells were treated with 5 µg/ml of L3-1Y antibody (c-Met mAb; Reference Example 1), 5 µg/ml of erbitux (EGFR mAb; Merck Serono, Germany), 5 µg/ml of L3-1Y antibody+5 µg/ml of erbitux, 5 µg/ml of ME19 or 5 µg/ml of ME22S (c-Met/EGFR bsAb; Example 2), 5 nM or 30 nM dasatinib (c-Src inhibitor; S1021, Selleckchem, US), 5 nM or 30 nM dasatinib+5 µg/ml of L3-1Y antibody, 5 nM or 30 nM dasatinib+5 µg/ml of erbitux, 5 nM or 30 nM dasatinib+5 µg/ml of L3-1Y antibody+5 µg/ml of erbitux, and 5 nM or 30 nM dasatinib+5 µg/m of ME19 or 5 µg/m of ME22S 1, respectively. At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well. In addition, further experiment was carried out referring to the experiment described above, except i) that the concentration of ME19 or ME22S was fixed to 0 or 5 µg/ml, and the concentration of dasatinib or saracatinib was varied (dasatinib: 0, 1, 10, 100, or 1000 nM; saracatinib: 0, 10, 100, 1000, or 10000 nM), or ii) that the concentration of dasatinib was fixed to 0 or 30 nM, and the concentration of ME19 was varied (0, 0.01, 0.1, 1 or 10 µg/ml). At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well.

At 72 hours after the treatment, 10 µL of Cell Counting Kit-8 solution (Dojindo Molecular Technologies, Gaithersburg, Md.) was added to each well, and left at room temperature for 2 hours. The number of the cells was counted by measuring the luminescence intensity, and the luminescence intensity was recorded using Envision 2104 Multi-label Reader (Perkin Elmer). The significance of the obtained data were verified through T-test (SigmaPlot 12.3; Systat Software Inc., Chicago, Ill.; *: P-value<0.001; : P-value<0.01; *: P-value<0.05).

Figure 8:
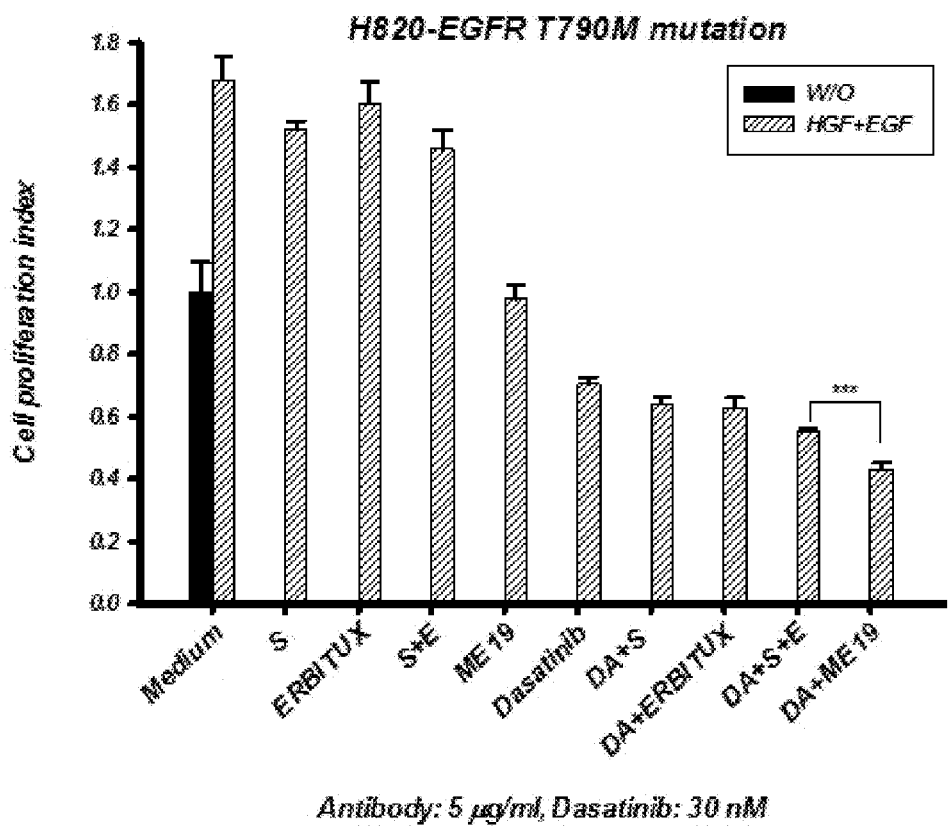
FIG. 8 is a graph showing cell proliferation degree of EGFR T790M mutated non-small cell lung cancer cell line (H820 cell line) when treated with a bispecific anti-c-Met/anti-EGFR antibody and c-Src inhibitor dasatinib or other agents.
Figure 9:
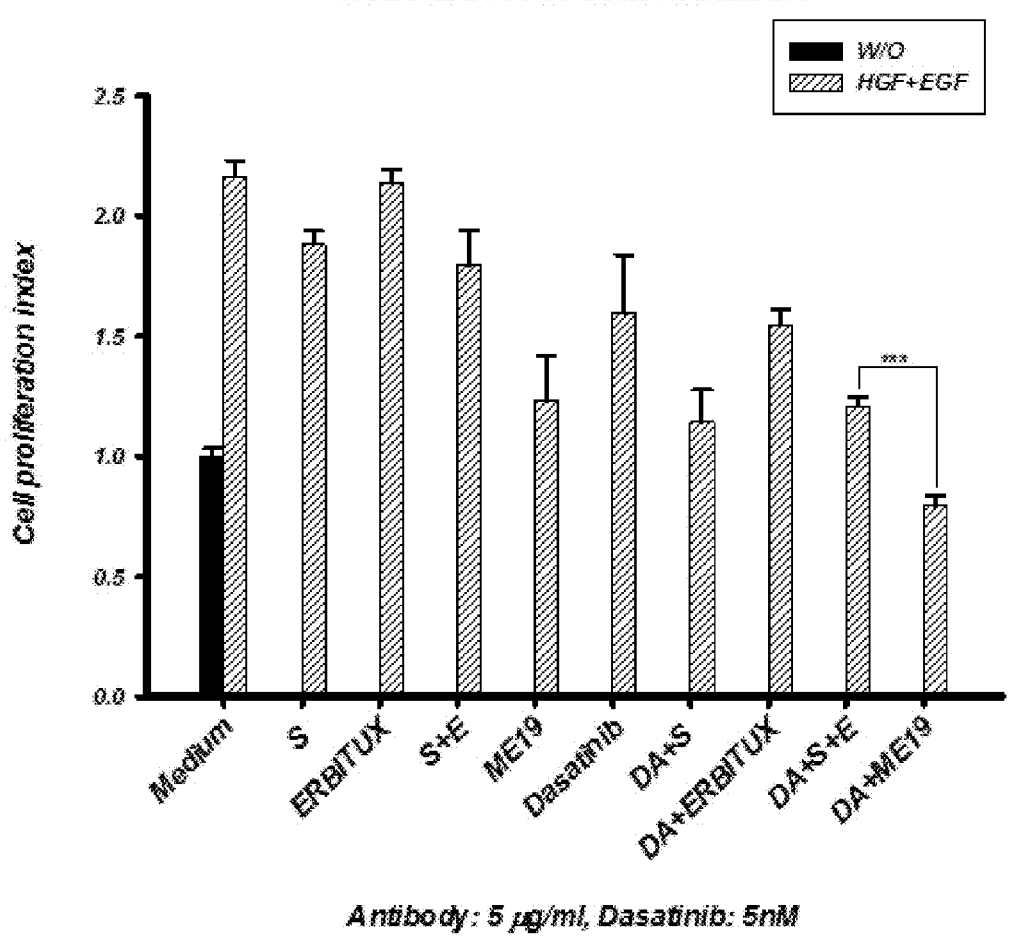
FIG. 9 is a graph showing cell proliferation degree of EGFR T790M mutated non-small cell lung cancer cell line (H820 cell line) when treated with a bispecific anti-c-Met/anti-EGFR antibody and c-Src inhibitor dasatinib or other agents.
Figure 10:
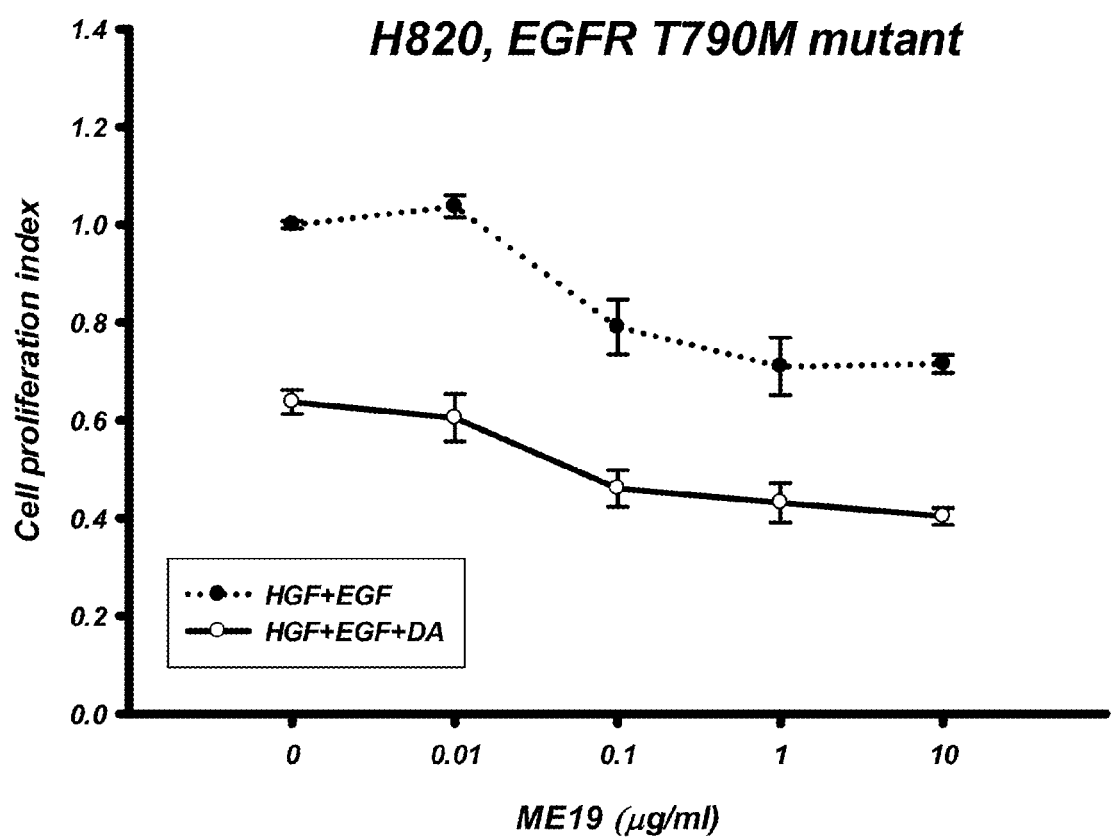
FIG. 10 is a graph showing cell proliferation degree of EGFR T790M mutated non-small cell lung cancer cell line (H820 cell line) when treated with a bispecific anti-c-Met/anti-EGFR antibody and a c-Src inhibitor at a variety of concentrations of bispecific anti-c-Met/anti-EGFR antibody ME19.
Figure 11:
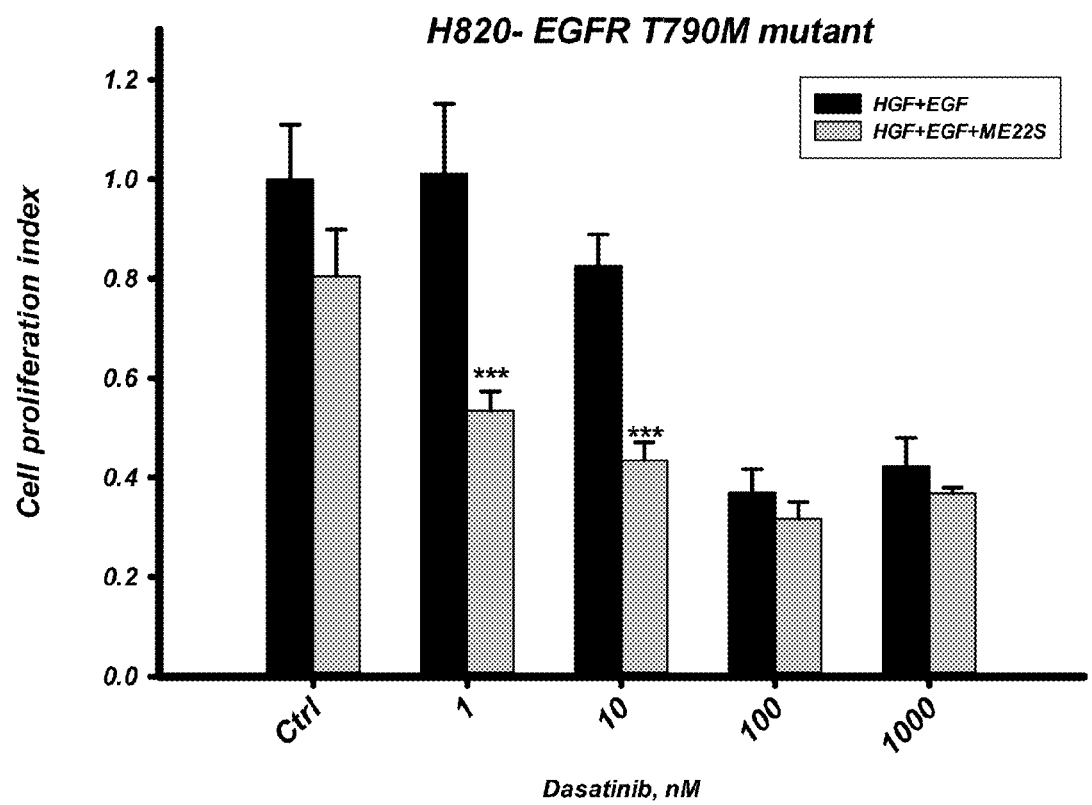
FIG. 11 is a graph showing cell proliferation degree of EGFR T790M mutated non-small cell lung cancer cell line (H820 cell line) when treated with a bispecific anti-c-Met/anti-EGFR antibody and a c-Src inhibitor at a fixed concentration of bispecific anti-c-Met/anti-EGFR antibody ME22 and a variety concentrations of dasatinib.
Figure 12:
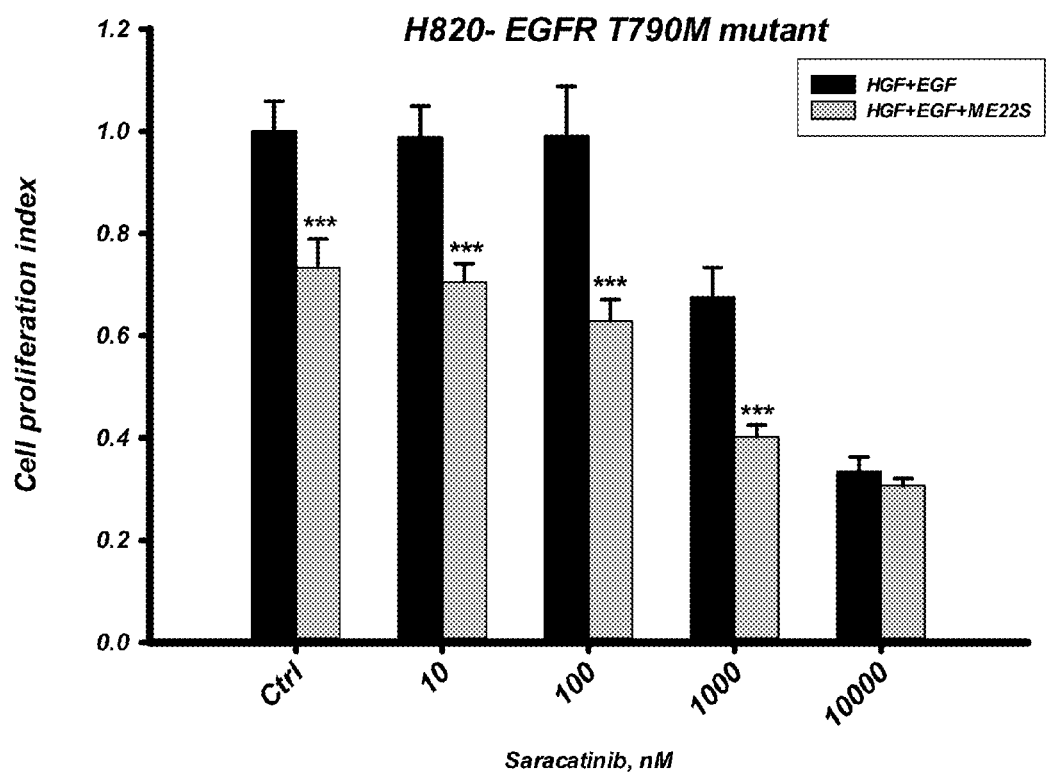
FIG. 12 is a graph showing cell proliferation degree of EGFR T790M mutated non-small cell lung cancer cell line (H820 cell line) when treated with a bispecific anti-c-Met/anti-EGFR antibody and a c-Src inhibitor at a fixed concentration of bispecific anti-c-Met/anti-EGFR antibody ME22 and a variety concentrations of saracatinib.

The obtained results are demonstrated in FIG. 8 (ME19 5 µg/ml, dasatinib 30 nM), FIG. 9 (ME19 5 µg/ml, dasatinib 5 nM), FIG. 10 (ME19 0, 0.01, 0.1, 1 or 10 µg/ml, dasatinib 0 or 30 nM), FIG. 11 (ME22 0 or 5 µg/ml, dasatinib 0, 1, 10, 100, or 1000 nM) and FIG. 12 (ME22 0 or 5 µg/ml, saracatinib 0, 10, 100, 1000, or 10000 nM).

FIG. 8 and FIG. 9 reveal that in the EGFR T790M mutated H820 cells treated with the combination of a bispecific anti-c-Met/anti-EGFR antibody and c-Src inhibitor dasatinib ("dasatinib" or "DA"), considerable inhibitory effect on the cell proliferation can be achieved, compared to those treated with the drugs alone. On the contrary, it is confirmed that the treatment with L3-1Y antibody ("S") and erbitux ("ERBITUX" or "E") alone or in combination leads to increased cell proliferation. These results indicate that by co-treatment of a bispecific anti-c-Met/anti-EGFR antibody and a c-Src inhibitor, a considerable anticancer effect on EGFR T790M mutated cancer cells can be obtained. In addition, even when compared to the case of co-treatment of a c-Src inhibitor (DA), an anti-c-Met antibody(S) and anti-EGFR antibody (E) (instead of a bispecific anti-c-Met/anti-EGFR antibody), the co-treatment of a bispecific anti-c-Met/anti-EGFR antibody and c-Src inhibitor dasatinib (DA) can achieve a considerable inhibition effect on cancer cell proliferation, indicating that the combination therapy using a bispecific anti-c-Met/anti-EGFR antibody and a c-Src inhibitor can lead to excellent anticancer effect compared to the case of co-treatment of three drugs which target the three targets respectively.

In addition, FIG. 10 to FIG. 12 demonstrate the degree of cell proliferation measured by varying the concentration of one of a bispecific anti-c-Met/anti-EGFR antibody and a c-Src inhibitor starting from 0 (with no treatment) and fixing the concentration of the other. FIG. 10 shows the results from the cases that bispecific anti-c-Met/anti-EGFR antibody is treated at various concentration together with 0 or 30 nM of a c-Src inhibitor, wherein the case of co-treatment of the bispecific anti-c-Met/anti-EGFR antibody and the c-Src inhibitor can lead to more considerable inhibition effect on the cell proliferation, compared to the case that the bispecific anti-c-Met/anti-EGFR antibody is treated alone (the case that concentration of a c-Src inhibitor is 0) or the c-Src inhibitor is treated alone (the case that concentration of ME19 is 0), and the inhibition effect on the cell proliferation is generally dose-dependent for the bispecific anti-c-Met/anti-EGFR antibody. FIG. 11 and FIG. 12 show the results from the cases that the c-Src inhibitor is treated at various concentration together with 0 or 5 µg/ml of the bispecific anti-c-Met/anti-EGFR antibody, wherein the case of co-treatment of the bispecific anti-c-Met/anti-EGFR antibody and the c-Src inhibitor can lead to more considerable inhibition effect on the cell proliferation, compared to the case that the bispecific anti-c-Met/anti-EGFR antibody is treated alone (the case that concentration of a c-Src inhibitor is 0; Ctrl) or the c-Src inhibitor is treated alone (the case that concentration of ME19 is 0), and the inhibition effect on the cell proliferation is generally dose-dependent for the c-Src inhibitor.

Example 5

Cell Proliferation Inhibition Effect on K-Ras Mutant Colorectal Cancer Cell Lines (HCT-116 Cell Line)

The effect of co-administration of a bispecific anti-c-Met/anti-EGFR antibody, ME-19 or ME22S, which is prepared in Example 2, and a c-Src inhibitor, dasatinib or saracatinib, was examined in a K-Ras mutated colorectal cancer cell line (HCT-116 cell line).

The HCT-116 cell line was obtained from ATCC (ATCC CCL-247). The HCT-116 cell line comprises K-Ras mutation (see www.atcc.org/products/all/CCL-247.aspx). The cells were stored in RPMI1640 medium (GIBCO) containing 10%(v/v) FBS under the conditions of 5% $CO_2$ and 37° C., until being used in the following experiments. A cell proliferation assay was performed as follows.

RPMI1640 medium (GIBCO) containing 10% FBS was added to 96-well plate. Lovo cells (ATCC, CCL-229) were seeded on the plate at the amount of 5,000 cells/well, and incubated overnight at 37° C. On the next day (after 24 hours), the incubated cells were treated with 5 µg/ml of L3-1Y antibody (c-Met mAb; Reference Example 1), 5 µg/ml of erbitux (EGFR mAb; Merck Serono, Germany), 5 µg/ml of L3-1Y antibody+5 µg/ml of erbitux, 5 µg/ml of ME19, 5 nM dasatinib (c-Src inhibitor; S1021, Selleckchem, US), 5 nM dasatinib+5 µg/ml of L3-1Y antibody, 5 nM dasatinib+5 µg/ml of erbitux, 5 nM dasatinib+5 µg/ml of L3-1Y antibody+5 µg/ml of erbitux, and 5 nM dasatinib+5 µg/m of ME19, respectively. At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well.

At 72 hours after the treatment, 10 µL of Cell Counting Kit-8 solution (Dojindo Molecular Technologies, Gaithersburg, Md.) was added to each well, and left at room temperature for 2 hours. The number of the cells was counted by measuring the luminescence intensity, and the luminescence intensity was recorded using Envision 2104 Multi-label Reader (Perkin Elmer). The significance of the obtained data were verified through T-test (SigmaPlot 12.3; Systat Software Inc., Chicago, Ill.; *: P-value<0.001; : P-value<0.01; *: P-value<0.05).

Figure 13:
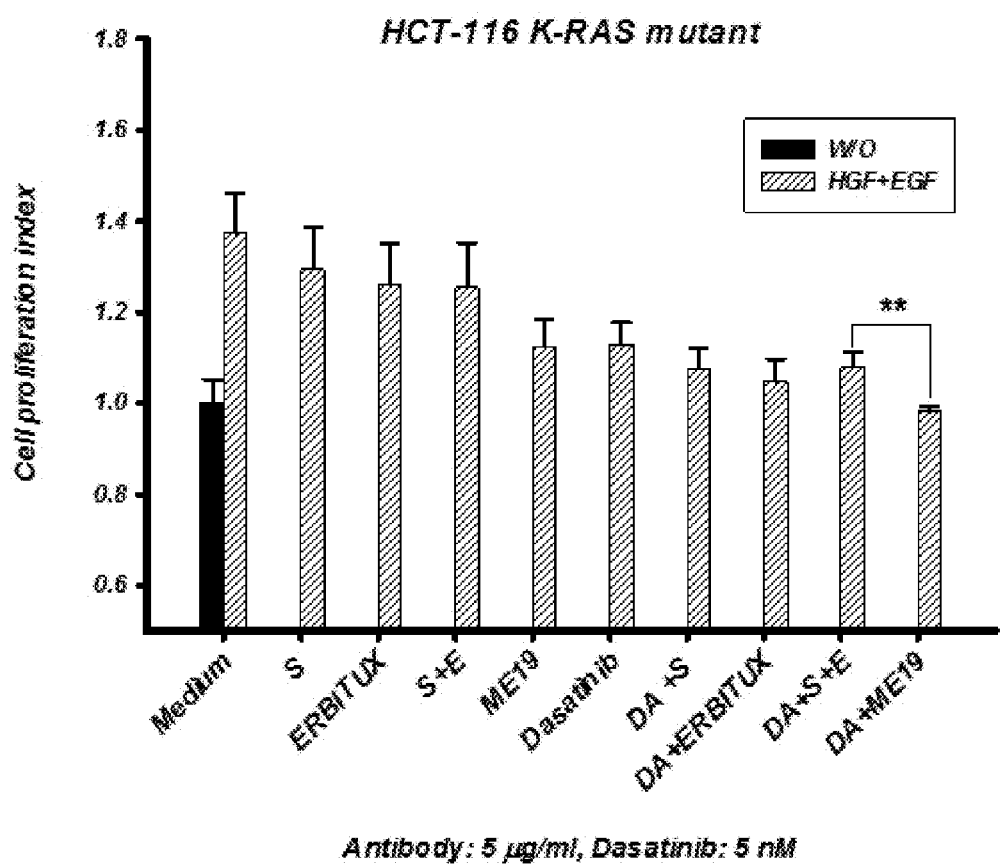
FIG. 13 is a graph showing cell proliferation degree of K-Ras mutated colorectal cancer cell line (HCT-116 cell line) when it is treated with bispecific anti-c-Met/anti-EGFR antibody ME19 and a c-Src inhibitor in addition to other therapeutics (e.g., erbitux, individually).

The obtained results are demonstrated in FIG. 13. As shown in FIG. 13, in K-Ras mutated HCT-116 cells which are co-treated with bispecific anti-c-Met/anti-EGFR antibody ME19 and c-Src inhibitor dasatinib ("DA"), more considerable cell proliferation inhibition effect can be obtained, compared to those treated with each of the drugs. These results indicate that the co-administration of a bispecific anti-c-Met/anti-EGFR antibody and a c-Src inhibitor can lead to an excellent anticancer effect on K-Ras mutated cancer cells. In addition, even when compared to the case of co-treatment of a c-Src inhibitor (DA), an anti-c-Met antibody(S) and anti-EGFR antibody (E) (instead of a bispecific anti-c-Met/anti-EGFR antibody), the co-treatment of a bispecific anti-c-Met/anti-EGFR antibody and c-Src inhibitor dasatinib (DA) can achieve a considerable inhibition effect on cancer cell proliferation, indicating that the combination therapy using a bispecific anti-c-Met/anti-EGFR antibody and a c-Src inhibitor can lead to more excellent anticancer effect compared to the case of co-treatment of three drugs which target the three targets respectively.

In addition, the cell proliferation inhibition effect was examined according to the amounts of dasatinib or saracatinib treated.

In detail, RPMI1640 medium (GIBCO) containing 10% FBS was added to 96-well plate. HCT-116 cells (ATCC, CCL-247) were seeded on the plate at the amount of 5,000 cells/well, and incubated overnight at 37° C. On the next day (after 24 hours), the incubated cells were treated with various concentrations (dasatinib: 0 (control), 10, 100, 1000 nM, saracatinib: 0 (control), 10, 100, 1000, 10000 nM) of c-Src inhibitor dasatinib (S1021, Selleckchem, US) or saracatinib (S1006, Selleckchem, US) alone or together with 5 µg/ml of bispecific anti-c-Met/anti-EGFR antibody ME22S. At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well.

At 72 hours after the treatment, 10 µL of Cell Counting Kit-8 solution (Dojindo Molecular Technologies, Gaithersburg, Md.) was added to each well, and left at room temperature for 2 hours. The number of the cells was counted by measuring the luminescence intensity, and the luminescence intensity was recorded using Envision 2104 Multi-label Reader (Perkin Elmer). The significance of the obtained data were verified through T-test (SigmaPlot 12.3; Systat Software Inc., Chicago, Ill.; *: P-value<0.001; : P-value<0.01; *: P-value<0.05).

Figure 14:
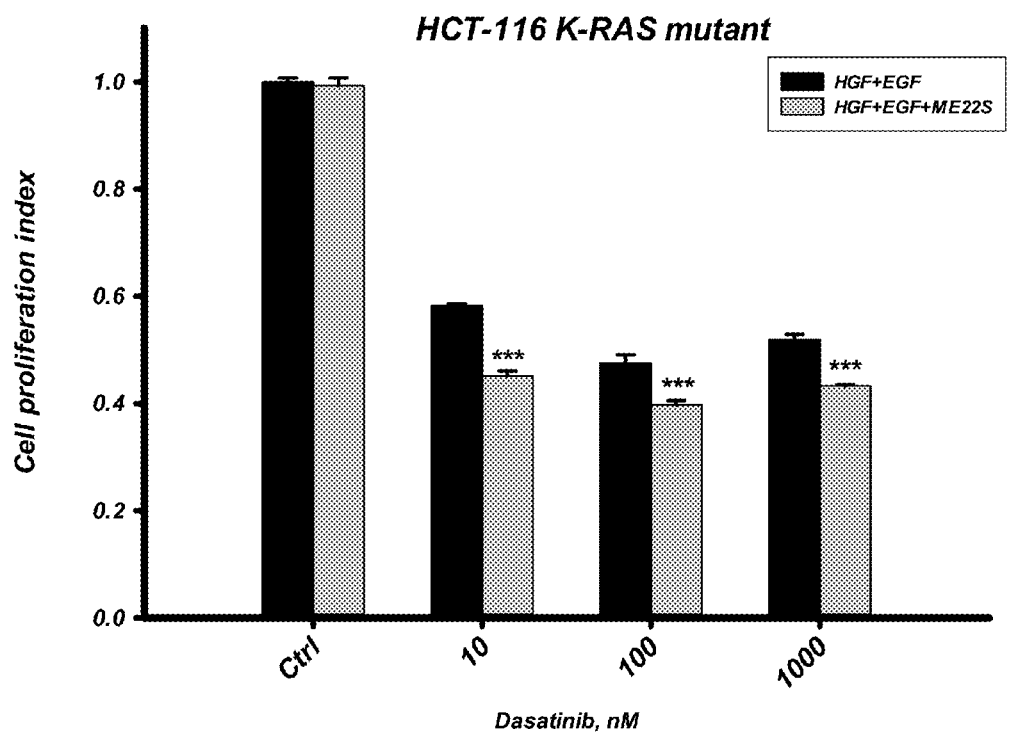
FIG. 14 is a graph showing cell proliferation degree of HCT-116 cell line when treated with bispecific anti-c-Met/anti-EGFR antibody and c-Src inhibitor dasatinib, according to the concentration of the treated c-Src inhibitor.
Figure 15:
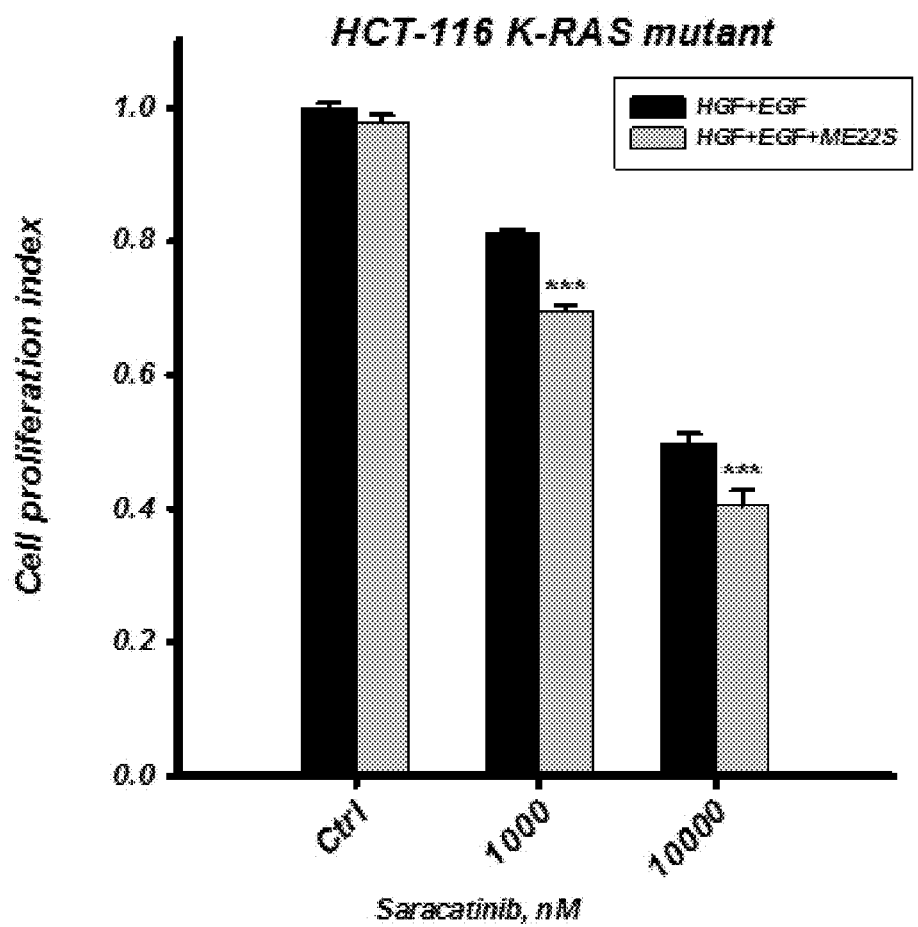
FIG. 15 is a graph showing cell proliferation degree of HCT-116 cell line when treated with bispecific anti-c-Met/anti-EGFR antibody and c-Src inhibitor saracatinib, according to the concentration of the treated c-Src inhibitor.

The obtained results are demonstrated in FIG. 14 (dasatinib) and FIG. 15 (saracatinib). As shown in FIG. 14 and FIG. 15, compared to the treatment of a c-Src inhibitor alone, the co-treatment of a bispecific anti-c-Met/anti-EGFR antibody and a c-Src inhibitor exhibits significantly synergistic therapeutic effect, and the synergistic therapeutic effect by the co-treatment (e.g., a difference between the co-treatment and the single treatment) is generally dose-dependent for the c-Src inhibitor.

In addition, RPMI1640 medium (GIBCO) containing 1% FBS was added to 96-well plate. HCT-116 cells (ATCC) were seeded on the plate at the amount of 5,000 cells/well, and incubated overnight at 37° C. On the next day (after 24 hours), the incubated cells were co-treated with a bispecific anti-c-Met/anti-EGFR antibody (5 µg/ml of ME19 or 5 µg/ml of M22S) and a c-Src inhibitor (0, 10, 100 or 1000 nM of dasatinib). At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well. 72 hours after, the cells were observed using an inverted microscopy (Model: Nikon ECLIPSE Ti-U; object lens: 10x).

Figure 16:
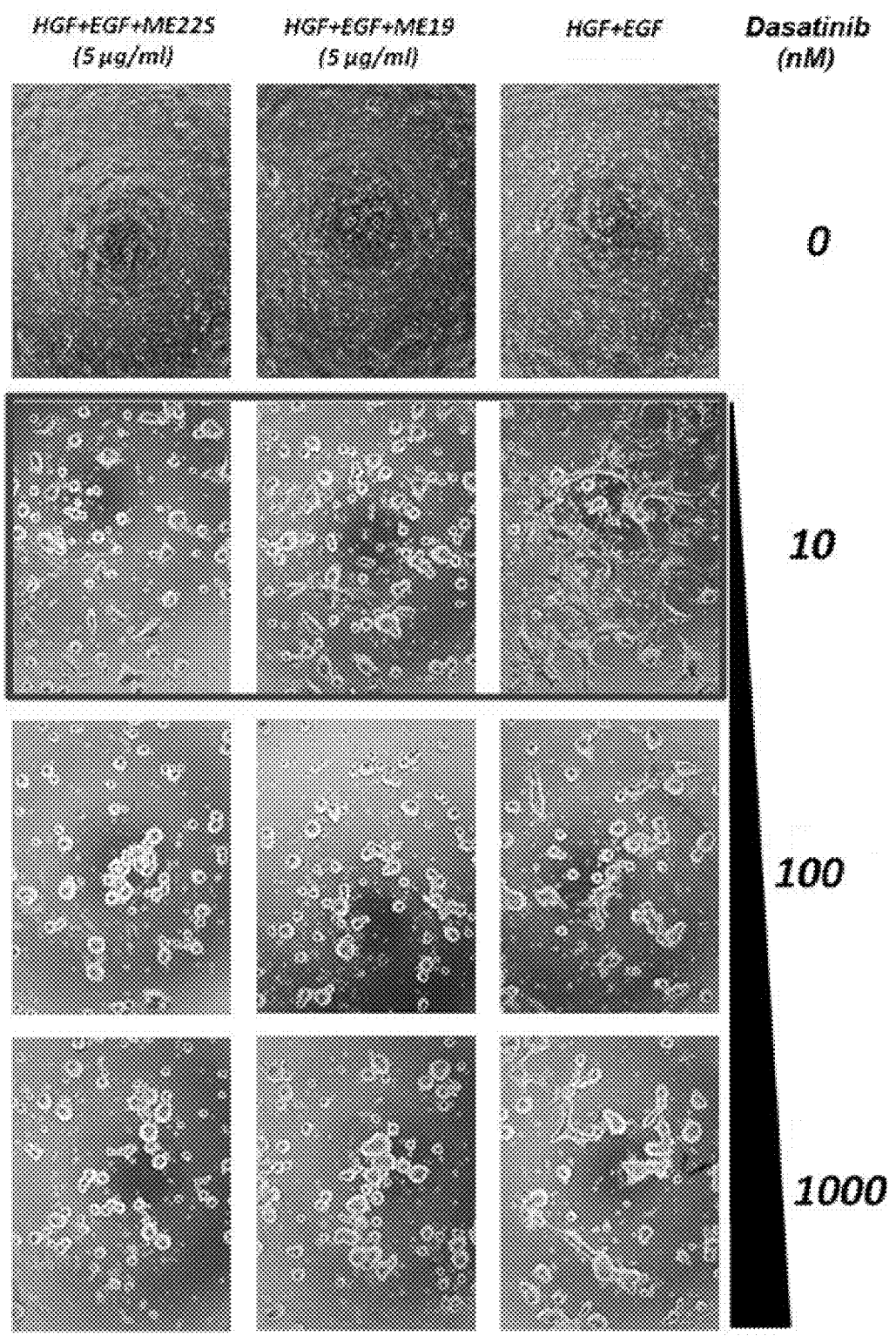
FIG. 16 is a series of inverted microscope images displaying the physical characteristics of an HCT-116 cell line when treated with a bispecific anti-c-Met/anti-EGFR antibody and c-Src inhibitor dasatinib.

The obtained results are demonstrated in FIG. 16. As shown in FIG. 16, when the c-Src inhibitor and the bispecific anti-c-Met/anti-EGFR antibody are co-administered, the shape of the cell is more regular and normalized, compared to the case that each of the c-Src inhibitor and the bispecific anti-c-Met/anti-EGFR antibody is treated alone.

Example 6

Cell Proliferation Inhibition Effect on EGFR T790M Mutant Non-Small Cell Lung Cancer Cell Line The effect by co-treatment of bispecific anti-c-Met/anti-EGFR antibody ME-19 prepared in Example 2 and a c-Src inhibitor dasatinib, saracatinib, or bosutinib, was examined in EGFR T790M mutated non-small cell lung cancer cell line (H1975).

The H1975 cell line was obtained from ATCC (ATCC CRL-5908). The H1975 cells comprise EGFR T790M mutation (see http://www.atcc.org/products/all/CRL-5908.aspx x). The cells were stored in RPMI1640 medium (GIBCO) containing 10%(v/v) FBS under the conditions of 5% $CO_2$ and 37° C., until being used in the following experiments. A cell proliferation assay was performed as follows.

The cell proliferation inhibition effect was examined according to the amounts of dasatinib, saracatinib, or bosutinib treated.

In detail, RPMI1640 medium (GIBCO) containing 10% FBS was added to 96-well plate. H1975 cells (ATCC, CCL-5908) were seeded on the plate at the amount of 5,000 cells/well, and incubated overnight at 37° C. On the next day (after 24 hours), the incubated cells were treated with various concentrations (0 (control), 10, 100, 1000 nM) of a c-Src inhibitor dasatinib (S1021, Selleckchem, US), saracatinib (S1006, Selleckchem, US), or bosutinib (S1014, Selleckchem, US) alone or together with 5 µg/ml of bispecific anti-c-Met/anti-EGFR antibody ME22S. At this time, the cells were treated with 100 ng/ml of HGF (#294-HG/CF, R&D SYSTEMS, Minneapolis, Minn.) and 100 ng/ml of EGF (#236-EG, R&D SYSTEMS, Minneapolis, Minn.) as well.

At 72 hours after the treatment, 10 μL of Cell Counting Kit-8 solution (Dojindo Molecular Technologies, Gaithersburg, Md.) was added to each well, and left at room temperature for 2 hours. The number of the cells was counted by measuring the luminescence intensity, and the luminescence intensity was recorded using Envision 2104 Multi-label Reader (Perkin Elmer). The significance of the obtained data were verified through T-test (SigmaPlot 12.3; Systat Software Inc., Chicago, Ill.; *: P-value<0.001; : P-value<0.01; *: P-value<0.05).

Figure 17:
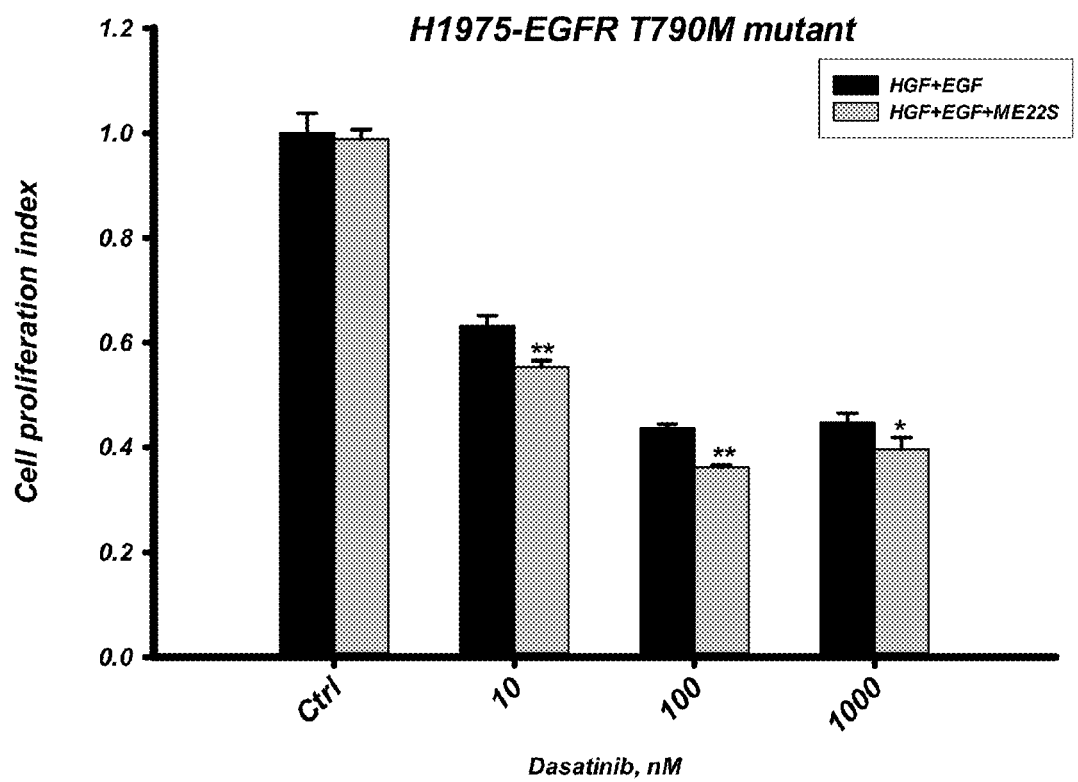
FIG. 17 is a graph showing cell proliferation degree of EGFR T790M mutated H1975 cell line when treated with a bispecific anti-c-Met/anti-EGFR antibody and c-Src inhibitor dasatinib, according to the concentration of the treated c-Src inhibitor.
Figure 18:
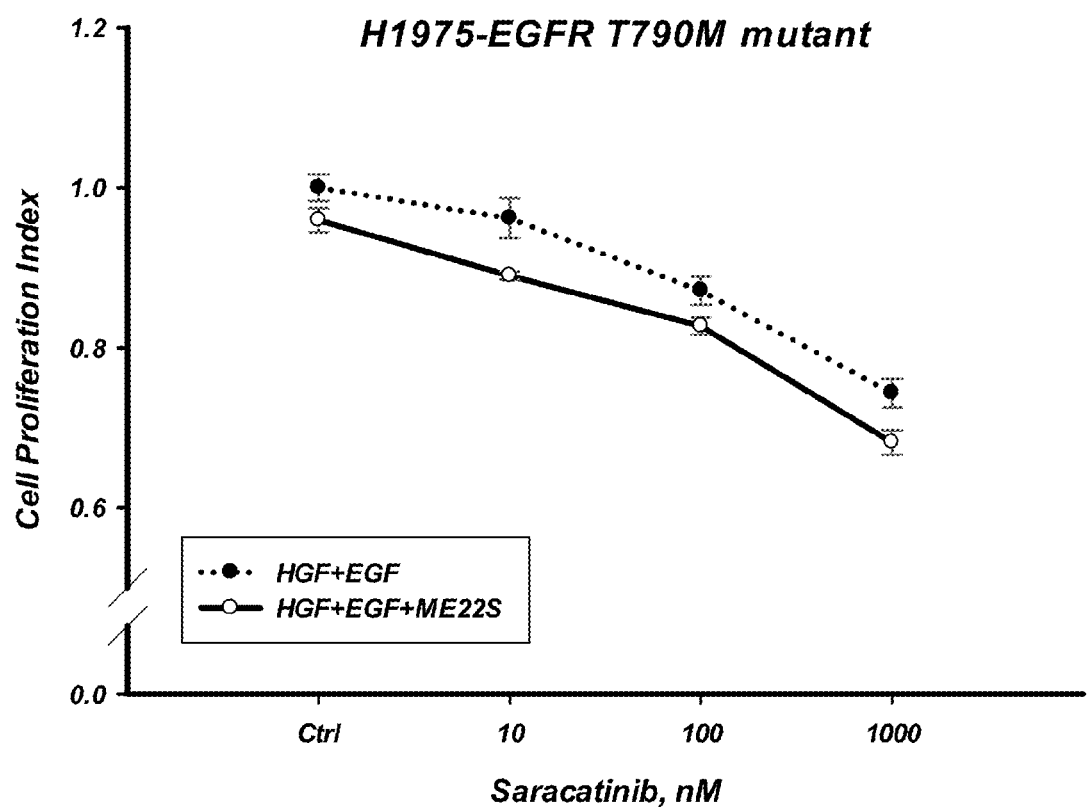
FIG. 18 is a graph showing cell proliferation degree of EGFR T790M mutated H1975 cell line when treated with a bispecific anti-c-Met/anti-EGFR antibody and c-Src inhibitor saracatinib, according to the concentration of the treated c-Src inhibitor.
Figure 19:
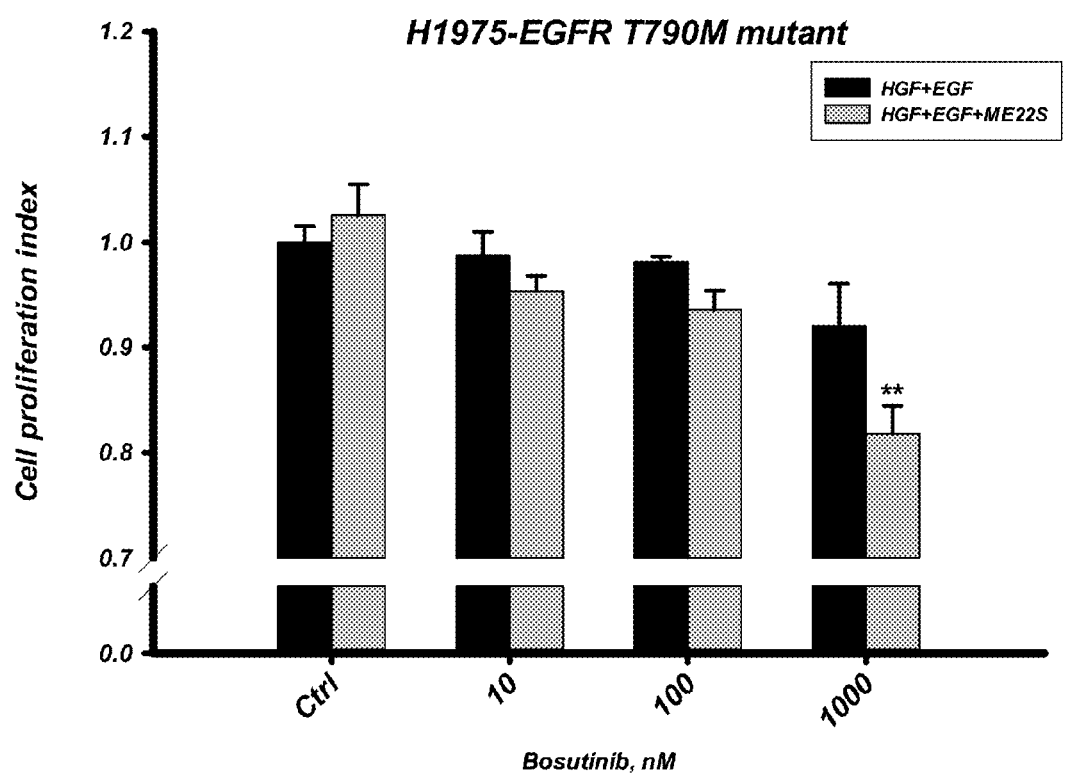
FIG. 19 is a graph showing cell proliferation degree of EGFR T790M mutated H1975 cell line when treated with a bispecific anti-c-Met/anti-EGFR antibody and c-Src inhibitor bosutinib, according to the concentration of the treated c-Src inhibitor.

The obtained results are demonstrated in FIG. 17 (dasatinib), FIG. 18 (saracatinib), and FIG. 19 (bosutinib). As shown in FIGS. 17 to 19, compared to the treatment of a c-Src inhibitor alone, the co-treatment of a bispecific anti-c-Met/anti-EGFR antibody and a c-Src inhibitor exhibits significantly synergistic therapeutic effect, and the synergistic therapeutic effect by the co-treatment (e.g., a difference between the co-treatment and the single treatment) is generally dose-dependent for the c-Src inhibitor.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a cancer comprising co-administering to a subject in need thereof a bispecific anti-c-Met/anti-EGFR antibody and a c-Src inhibitor to a subject, wherein the bispecific anti-c-Met/anti-EGFR antibody comprises an EGFR binding region and an anti-c-Met antibody or antigen-binding fragment thereof, and
wherein the anti c-Met antibody or the antigen-binding fragment thereof comprises a heavy chain variable region comprising a CDR-H1 comprising SEQ ID NO: 1, a CDR-H2 comprising SEQ ID NO: 2, and a CDR-H3 comprising SEQ ID NO: 3, and a light chain variable region comprising a CDR-L1 comprising SEQ ID NO: 10, a CDR-L2 comprising SEQ ID NO: 11, and a CDR-L3 comprising SEQ ID NO: 13,
and wherein the cancer to be treated is colon cancer, lung cancer, colon cancer comprising a K-Ras mutation, or lung cancer comprising an EGFR T790M mutation.

2. The method of claim 1, wherein the bispecific anti-c-Met/anti-EGFR antibody and the Src inhibitor are co-administered by administering a composition comprising the bispecific anti-c-Met/anti-EGFR antibody and the c-Src inhibitor, or administering a first composition comprising the bispecific anti-c-Met/anti-EGFR antibody and a second composition comprising the c-Src inhibitor, wherein the first composition and second composition are administered simultaneously or sequentially in any order.

3. The method of claim 1, wherein the anti-c-Met antibody or antigen-binding fragment thereof comprises:
a heavy chain variable region comprising SEQ ID NO: 17; and
a light chain variable region comprising SEQ ID NO: 129 or SEQ ID NO: 18.

4. The method of claim 1, wherein the anti-c-Met antibody comprises:
a heavy chain comprising SEQ ID NO: 62, the 18th to 462nd positions of SEQ ID NO: 62, SEQ ID NO: 64, the 18th to 461st positions of SEQ ID NO: 64, SEQ ID NO: 66, or the 18th to 460th positions of SEQ ID NO: 66; and
a light chain comprising SEQ ID NO: 68, the 21st to 240th positions of SEQ ID NO: 68, SEQ ID NO: 70, the 21st to 240th positions of SEQ ID NO: 70, or SEQ ID NO: 108.

5. The method of claim 1, wherein the EGFR binding region comprises an anti-EGFR antibody, antigen-binding fragment thereof, or an anti-EGFR DARPin.

6. The method of claim 5, wherein the anti-EGFR antibody or antigen-binding fragment thereof is selected from the group consisting of:
(1) cetuximab or antigen binding fragment thereof;
(2) panitumumab or antigen binding fragment thereof;
(3) an anti-EGFR antibody comprising a heavy chain variable region comprising SEQ ID NO: 109, and a light chain variable region comprising SEQ ID NO: 111;
(4) an anti-EGFR antibody comprising a heavy chain variable region comprising SEQ ID NO: 113, and a light chain variable region comprising SEQ ID NO: 114; and
(5) an anti-EGFR antibody comprising a CDR-H1 comprising SEQ ID NO: 115, a CDR-H2 comprising SEQ ID NO: 116, and a CDR-H3 comprising SEQ ID NO: 117, a CDR-L1 comprising SEQ ID NO: 118, a CDR-L2 comprising SEQ ID NO: 119, and a CDR-L3 comprising SEQ ID NO: 120.

7. The method of claim 6, wherein the anti-EGFR antibody or antigen-binding fragment thereof is an anti-EGFR antibody, an anti-EGFR scFv, or an anti-EGFR scFv-Fc comprising a heavy chain variable region comprising SEQ ID NO: 109, SEQ ID NO: 113, SEQ ID NO: 121, or SEQ ID NO: 122; and a light chain variable region comprising SEQ ID NO: 111, SEQ ID NO: 114, SEQ ID NO: 123, or SEQ ID NO: 124.

8. The method of claim 5, wherein the EGFR binding region comprises an anti-EGFR DARPin, and the anti-EGFR DARPin comprises 1 to 10 units, wherein each unit is independently selected from the group consisting of SEQ ID NOs: 125 to 127.

9. The method of claim 1, wherein the c-Src inhibitor is at least one selected from the group consisting of dasatinib, saracatinib, bosutinib, 1-Naphthyl PP1 (CAS 221243-82-9), A 419259 trihydrochloride (CAS 364042-47-7), AG 538 (CAS 133550-18-2), AGL 2263 ((E)-2-(3,4-dihydroxybenzoyl)-3-(2-oxo-3H-1,3-benzoxazol-5-yl)prop-2-enenitrile), Bcr-abl Inhibitor II (CAS 607702-99-8), bosutinib (CAS 380843-75-4), altenusin (CAS 31186-12-6), herbimycin A(CAS 70563-58-5), PD 166285 (CAS 212391-63-4), PKC-412 (CAS 120685-11-2), PDGFR Tyrosine Kinase Inhibitor IV (CAS 627518-40-5), Calphostin C (CAS 121263-19-2), PP 1 (CAS 172889-26-8), PP 2 (CAS 172889-27-9), Src Kinase Inhibitor I (CAS 179248-59-0), EGF/FGF/PDGF Receptor Tyrosine Kinase Inhibitor (CAS 1135256-66-4), staurosporine (CAS 62996-74-1), lavendustin A (CAS 125697-92-9), Indirubin-3'-(2,3-dihydroxypropyl)oximether, luteolin (CAS 491-70-3), SU6656 (CAS 330161-87-0), TX-1918 (CAS 503473-32-3), geldanamycin (CAS 0562-34-6), MNS (CAS 1485-00-3), TX-1123 (CAS 157397-06-3), GW5074 (CAS 220904-83-6), Erlotinib HCl (CAS 183319-69-9), NVP-BHG712 (CAS 940310-85-0), GW2580 (CAS 870483-87-7), AEE788 (CAS 497839-62-0), TAK-901 (CAS 934541-31-8), Midostaurin (CAS 120685-11-2), and PD173074 (CAS 219580-11-7), or any combination thereof.

10. A pharmaceutical composition comprising a bispecific anti-c-Met/anti-EGFR antibody of claim 1 and a carrier.

\* \* \* \* \*